(12) United States Patent
Jadhav et al.

(10) Patent No.: US 8,426,581 B2
(45) Date of Patent: Apr. 23, 2013

(54) RNA INTERFERENCE MEDIATED INHIBITION OF THE FCεR1α GENE

(75) Inventors: Vasant Jadhav, Harleysville, PA (US); Victoria Pickering, Pacifica, CA (US); Walter Strapps, San Mateo, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/256,095

(22) PCT Filed: Mar. 25, 2010

(86) PCT No.: PCT/US2010/028687
§ 371 (c)(1),
(2), (4) Date: Sep. 12, 2011

(87) PCT Pub. No.: WO2010/111503
PCT Pub. Date: Sep. 30, 2010

(65) Prior Publication Data
US 2012/0004280 A1    Jan. 5, 2012

Related U.S. Application Data

(60) Provisional application No. 61/164,275, filed on Mar. 27, 2009.

(51) Int. Cl.
*C07H 21/04* (2006.01)
*C12N 15/11* (2006.01)

(52) U.S. Cl.
USPC ........................................ 536/24.5; 514/44 A

(58) Field of Classification Search ................ 536/24.5; 514/44 A
See application file for complete search history.

(56) References Cited

U.S. PATENT DOCUMENTS

2005/0159380 A1* 7/2005 Guerciolini et al. ............ 514/44
2007/0185049 A1* 8/2007 Jadhav et al. ................... 514/44

* cited by examiner

*Primary Examiner* — Jon E Angell
(74) *Attorney, Agent, or Firm* — Peter Haeberli; David A. Muthard

(57) ABSTRACT

The present invention relates to compounds, compositions, and methods for the study, diagnosis, and treatment of traits, diseases and conditions that respond to the modulation of FCεR1α gene expression and/or activity, and/or modulate a FCεR1α gene expression pathway. Specifically, the invention relates to doublestranded nucleic acid molecules including small nucleic acid molecules, such as short interfering nucleic acid (siNA), short interfering RNA (siRNA), double-stranded RNA (dsRNA), micro-RNA (miRNA), and short hairpin RNA (shRNA) molecules that are capable of mediating or that mediate RNA interference (RNAi) against FCεR1α gene expression.

4 Claims, 12 Drawing Sheets

Figure 4C

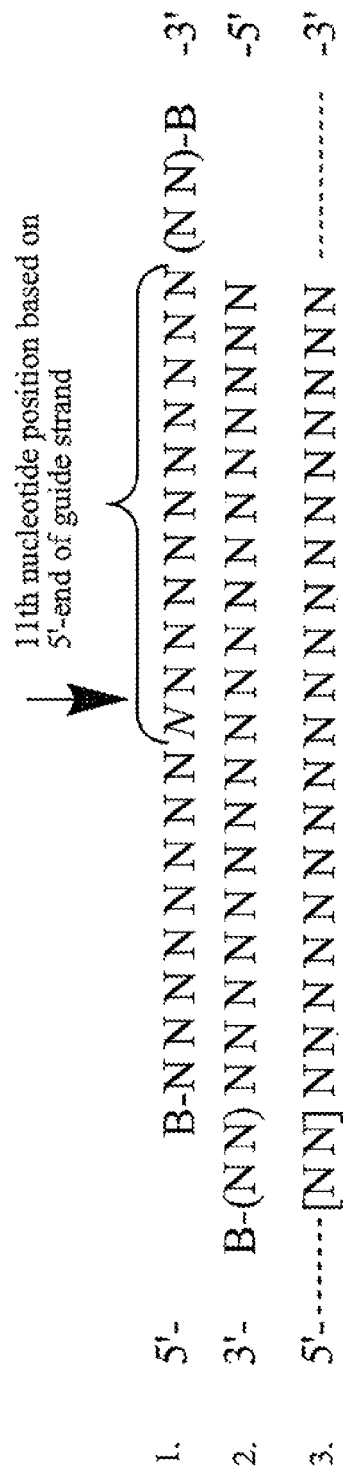

1. = sense strand (passenger strand)
2. = antisense strand (guide strand)
3. = target polynucleotide sequence The guide strand is complementary to the target sequence and the passenger strand is complementary to the guide strand. Overhang nucleotides (NN) in the guide strand can be complementary to nucleotides [NN] in target sequence. Overhang nucleotides (NN) in the passenger strand can comprise nucleotides [NN] in target sequence. Position N of the passenger strand can comprise a ribonucleotide. For the representative 19 base pair 21 mer duplex shown, position N is 9 nucleotides in from the 3' end of the passenger strand. However, in duplexes of differing length, the position N is determined based on the 5'-end of the guide strand by counting 11 nucleotides in from the 5'-terminus of the guide strand and picking the corresponding base paired nucleotide in the passenger strand. Cleavage by Ago2 takes place between positions 10 and 11 as indicated by the arrow.
Representative 2 nucleotide overhangs are shown, but can vary for example from 0 to about 4 nucleotides.
B = terminal cap which can be present or absent
This generalized motif can be applied to all Stab 00-34 chemistries herein.

Figure 6: Modification Strategy

Figure 7: Phosphorylated siNA constructs

Figure 8: 5'-phosphate modifications

*Figure 9: Cholesterol Conjugate Approach*

RNA INTERFERENCE MEDIATED INHIBITION OF THE FCεR1α GENE

This application claims the benefit of U.S. Provisional Application No. 61/164,275, filed Mar. 27, 2009. The above listed application is hereby incorporated by reference herein in its entirety, including the drawings.

SEQUENCE LISTING

The sequence listing submitted via EFS, in compliance with 37 CFR §1.52(e)(5), is incorporated herein by reference. The sequence listing text file submitted via EFS contains the file "SequenceListing80WPCT", created on Mar. 19, 2010, which is 102,148 bytes in size.

BACKGROUND OF THE INVENTION

A central feature of allergic reactions is the aggregation of the high-affinity IgE Receptor, (also known as FCεR1), to initiate a change in the behavior of the cell expressing the receptor. The high affinity Fc epsilon receptor is associated with the activation of mast cells and basophils and the triggering of allergic reactions and anaphylactic shock. Moreover, knockout mice for the FCεR1 alpha chain (FCεR1α) are unable to mount IgE-mediated anaphylaxis (Dombrowicz et al., 1993, Cell 75, 969-976).

FCεR1 is not only expressed on so-called effector cells of allergic reaction, i.e. mast cells and basophils, but there is clear evidence that Langerhans cells, monocytes (or a subset of monocytes), and cells derived from monocytes, such as dendritic cells, also express this receptor (e.g., Wang, B., et al., 1992 J. Exp. Med. 175, 1353-1365, and Maurer, D., S. et al., 1996, J. Immunol. 157, 607-616). Moreover, expression levels of FCεR1 on these cell types correlates with atopic status (Maurer, D. S, et al., 1994, J. Exp. Med. 179, 745-750.

The high affinity IgE binding receptor expressed on mast cells and basophils is a tetrameric receptor comprised of the IgE-binding α chain, the membrane-tetra-spanning β chain, and a disulfide-linked homodimer of the γ chains. FCεR1 expressed on other cells of the immune system e.g., dendritic cells is a trimeric receptor comprised of a single αchain and the γ chain homodimer. The alpha chain of FCεR1 binds IgE molecules with high affinity (K D of about 10-9 to 10-10 moles/liter (M)) at a stoichiometry of 1:1, whereas the β and γ chains of FCεR1α are signal transduction modules. Loss of FCεR1α chain of this receptor prevents surface expression of the receptor complex and ablates IgE binding.

Crosslinking of IgE molecules bound to FCεR1 by an allergen activates a signaling cascade in mast, basophil and other immune cells that results in the release of chemical mediators responsible for numerous adverse events. That is, activation of the FCεR1 signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens), hay fever, allergic conjunctivitis, allergic rhinitis, allergic asthma, atopic dermatitis, eczema, urticaria. It also leads to the synthesis and release of other mediators, including leukotrienes, prostaglandins and platelet-activating factors (PAFs), that play important roles in inflammatory reactions. The resulting smooth muscle contraction and acute bronchoconstriction constitutes the so-called early phase response of an asthmatic reaction. Additional mediators that are synthesized and released upon crosslinking FCεR1 receptors include cytokines and chemokines such as IL-4, IL-5, IL-6, TNF-α, IL-13 and MIP1-α) and nitric oxide. These mediators contribute to delayed bronchoconstriction and an increase in airway hyperreactivity the so-called late phase response in an asthmatic reaction. Pathologically, the late-phase response is characterized by cellular inflammation of the airway, increased bronchovascular permeability, and increased mucus secretion. Accordingly, in mice lacking the FCεR1α chain, airways hyper-responsiveness is ablated and inflammation reduced following aeroallergen sensitization and challenge (Taube, C et al., 2004, J. Immunol 172, 6398-6406).

Furthermore, this cytokine and chemokine mileu further enhances allergic sensitization by promoting naïve T cell differentiation into Th2 cells via IL4-R signaling. IL4 also promotes class-switching to IgE in B cells and there is mounting evidence that in addition to Th2 cells, basophils are a primary source of IL-4 and IL-13 (see e.g., Gauchat, J. F. et al., 1993, Nature, 365, 340-343). Basophils secrete quantities similar to T cells, and because the frequency of basophils (with their panspecific IgE) is much greater than that of antigen-specific Th2 cells, potentially basophils may generate most of the IL-4 present in tissues via allergen-activated FCεR1 (see e.g., Devouassoux, G. et al., 1999, J. Allergy Clin. Immunol. 104, 811-819). Hence, significant reductions in IL-4 and IL-13 secretion from basophils could have long-term consequences for the synthesis of IgE.

An important advancement in the treatment of allergic rhinitis and asthma in recent years has been the development of monoclonal antibodies specifically targeting IgE. Studies in allergic rhinitics with the anti-IgE humanised monoclonal antibody (omalizumab, Xolair™) have demonstrated significant reduction in nasal symptoms and improvement in quality of life (Owen, C., 2007, Pharmacology and Therapeutics 113, 121-133). More recently it has been demonstrated that omalizumab is particularly effective in patients with both asthma and rhinitis (Vignola et al., 2004, Allergy 59, 709-717) and also in poorly controlled asthmatics despite high-dose inhaled corticosteroid therapy and particularly those at the more severe end of the spectrum. In these patients, the most significant benefit is in the reduction in exacerbation rate and airway inflammation (Nowak., 2006 Resp. Med. 100, 1907-1917). Ex vivo studies have shown that one of the mechanisms by which anti-IgE may mediate its clinical benefit is by down-regulating the expression and function FCεR1 on surface of circulating basophils, tissue-resident mast cells (Beck et al., 2004, J Allergy Clin Immunol. 114, 527-30) and dendritic cells. There remains, however, a need for other therapeutics to treat disease associated with aggregation of the high-affinity IgE Receptor.

Alteration of gene expression, specifically FCεR1α gene expression, through RNA interference (hereinafter "RNAi") is a one approach for meeting this need. RNAi is induced by short double-stranded RNA ("dsRNA") molecules. The short dsRNA molecules, called "short interfering RNA" or "siRNA" or "RNAi inhibitors" silence the expression of messenger RNAs ("mRNAs") that share sequence homology to the siRNA. This can occur via cleavage of the mRNA mediated by an endonuclease complex containing a siRNA, commonly referred to as an RNA-induced silencing complex (RISC). Cleavage of the target RNA typically takes place in the middle of the region complementary to the guide sequence of the siRNA duplex (Elbashir et al., 2001, Genes Dev., 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237).

SUMMARY OF THE INVENTION

The present invention provides compounds, compositions, and methods useful for modulating the expression of FCεR1α genes, specifically those FCεR1α genes associated with the development or maintenance of inflammatory and/or respiratory diseases and conditions by RNA interference (RNAi) using small nucleic acid molecules.

In particular, the instant invention features small nucleic acid molecules, i.e., short interfering nucleic acid (siNA) molecules including, but not limited to, short interfering RNA (siRNA), double-stranded RNA (dsRNA), micro-RNA (miRNA), short hairpin RNA (shRNA) and circular RNA molecules and methods used to modulate the expression of FCεR1α genes and/or other genes involved in pathways of FCεR1α gene expression and/or activity.

In one aspect, the present invention provides a double-stranded short interfering nucleic acid (siNA) molecule comprising a first strand and a second strand having complementary to each other, wherein at least one strand comprises at least 15 nucleotides of:

```
5'-CUUGCAAUAUACAUAGAAA-3';      (SEQ ID NO: 2)
5'-UUUCUAUGUAUAUUGCAAG-3';      (SEQ ID NO: 131)
5'-CCAUGGAAUAGAAUAUUUA-3';      (SEQ ID NO: 3)
5'-UAAAUAUUCUAUUCCAUGG-3';      (SEQ ID NO: 132)
5'-CCCUCAACAUUACUGUAAU-3';      (SEQ ID NO: 5)
5'-AUUACAGUAAUGUUGAGGG-3';      (SEQ ID NO: 133)
5'-UCAGCACCAACAAGUUAAU-3';      (SEQ ID NO: 8)
5'-AUUAACUUGUUGGUGCUGA-3';      (SEQ ID NO: 134)
5'-ACAGGAUUAUUUAUCUCAA-3';      (SEQ ID NO: 9)
5'-UUGAGAUAAAUAAUCCUGU-3'       (SEQ ID NO: 135)
5'-UGGUGGUGAUUCUGUUUGC-3';      (SEQ ID NO: 17)
or
5'-GCAAACAGAAUCACCACCA-3';      (SEQ ID NO: 136)
``` and wherein one or more of the nucleotides are optionally chemically modified.

In some embodiments of the invention, all of the nucleotides are unmodified. In other embodiments, one or more (e.g., 1, 2, 3, 4, 5, 6, 7, 8, 9, 10, 11, 12, 13, 14, 15, 16, 17, 18, 19. 20 or 21 modified nucleotides) of the nucleotide positions in one or both strands of an siNA molecule are modified. Modifications include nucleic acid sugar modifications, base modifications, backbone (internucleotide linkage) modifications, non-nucleotide modifications, and/or any combination thereof. In certain instances, purine and pyrimidine nucleotides are differentially modified. For example, purine and pyrimidine nucleotides can be differentially modified at the 2'-sugar position (i.e., at least one purine has a different modification from at least one pyrimidine in the same or different strand at the 2'-sugar position). In other instances, at least one modified nucleotide is a 2'-deoxy-2'-fluoro nucleotide, a 2'-deoxy nucleotide, or a 2'-O-alkyl nucleotide In certain embodiments, the siNA molecule has 3' overhangs of one, two, three, or four nucleotide(s) on one or both of the strands. In other embodiments, the siNA lacks overhangs (i.e., has blunt ends). Preferably, the siNA molecule has 3' overhangs of two nucleotides on both the sense and anti-sense strands. The overhangs can be modified or unmodified. Examples of modified nucleotides in the overhangs include, but are not limited to, 2'-O-alkyl nucleotides, 2'-deoxy-2'-fluoro nucleotides, or 2'-deoxy nucleotides. The overhang nucleotides in the antisense strand can comprise nucleotides that are complementary to nucleotides in the FCεR1α target sequence. Likewise, the overhangs in the sense stand can comprise nucleotides that are in the FCεR1α target sequence. In certain instances, the siNA molecules of the invention have two 3' overhang nucleotides on the antisense stand that are 2'-O-alkyl nucleotides and two 3' overhang nucleotides on the sense stand that are 2'-deoxy nucleotides.

In some embodiments, the siNA molecule has caps (also referred to herein as "terminal caps" The cap can be present at the 5'-terminus (5'-cap) or at the 3'-terminus (3'-cap) or can be present on both termini, such as at the 5' and 3' termini of the sense (guide) strand of the siNA.

In certain embodiments, double-stranded short interfering nucleic acid (siNA) molecules are provided, wherein the molecule has a sense strand and an antisense strand and comprises formula (A):

(A)

wherein, the upper strand is the sense strand and the lower strand is the antisense strand of the double-stranded nucleic acid molecule; wherein the antisense strand comprises at least 15 nucleotides of SEQ ID NO: 131, SEQ ID NO: 132, SEQ ID NO: 133, SEQ ID NO: 134, SEQ ID NO: 135, or SEQ ID NO: 136, and the sense strand comprises a sequence having complementarity to the antisense strand;

each N is independently a nucleotide which is unmodified or chemically modified;

each B is a terminal cap that is present or absent;

(N) represents overhanging nucleotides, each of which is independently unmodified chemically modified;

[N] represents nucleotides that are ribonucleotides;

X1 and X2 are independently integers from 0 to 4;

X3 is an integer from 17 to 36;

X4 is an integer from 11 to 35; and

X5 is an integer from 1 to 6, provided that the sum of X4 and X5 is 17-36;

In one embodiment, the invention features a double-stranded short interfering nucleic acid (siNA) of formula (A); wherein (a) one or more pyrimidine nucleotides in $N_{X4}$ positions are independently 2'-deoxy-2'-fluoro nucleotides, 2'-O-alkyl nucleotides, 2'-deoxy nucleotides, ribonucleotides, or any combination thereof;

(b) one or more purine nucleotides in $N_{X4}$ positions are independently 2'-deoxy-2'-fluoro nucleotides, 2'-O-alkyl nucleotides, 2'-deoxy nucleotides, ribonucleotides, or any combination thereof;

(c) one or more pyrimidine nucleotides in $N_{X3}$ positions are independently 2'-deoxy-2'-fluoro nucleotides, 2'-O-alkyl nucleotides, 2'-deoxy nucleotides, ribonucleotides, or any combination thereof; and (d) one or more purine nucleotides in $N_{X3}$ positions are independently 2'-deoxy-2'-fluoro nucleotides, 2'-O-alkyl nucleotides, 2'-deoxy nucleotides, ribonucleotides, or any combination thereof.

In one embodiment, the invention features a double-stranded short interfering nucleic acid (siNA) of formula (A); wherein (a) each pyrimidine nucleotide in $N_{X4}$ positions is independently a 2'-deoxy-2'-fluoro nucleotide, 2'-O-alkyl nucleotide, 2'-deoxy nucleotide, or ribonucleotide;

(b) each purine nucleotide in $N_{X4}$ positions is independently a 2'-deoxy-2'-fluoro nucleotide, 2'-O-alkyl nucleotide, 2'-deoxy nucleotide, or ribonucleotide;

(c) each pyrimidine nucleotide in $N_{X3}$ positions is independently a 2'-deoxy-2'-fluoro nucleotide, 2'-O-alkyl nucleotide, 2'-deoxy nucleotide, or ribonucleotide; and (d) each purine nucleotides in $N_{X3}$ positions is independently a 2'-deoxy-2'-fluoro nucleotide, 2'-O-alkyl nucleotide, 2'-deoxy nucleotide, or ribonucleotide.

In one embodiment, the invention features a double-stranded short interfering nucleic acid (siNA) of formula (A); wherein (a) each pyrimidine nucleotide in $N_{X4}$ positions is independently a 2'-deoxy-2'-fluoro nucleotide;

(b) each purine nucleotide in $N_{X4}$ positions is independently a 2'-O-alkyl nucleotide;

(c) each pyrimidine nucleotide in $N_{X3}$ positions is independently a 2'-deoxy-2'-fluoro nucleotide; and (d) each purine nucleotide in $N_{X3}$ positions is independently a 2'-deoxy nucleotide.

In one embodiment, the invention features a double-stranded short interfering nucleic acid (siNA) of formula (A); wherein (a) each pyrimidine nucleotide in $N_{X4}$ positions is independently a 2'-deoxy-2'-fluoro nucleotide;

(b) each purine nucleotide in $N_{X4}$ positions is independently a 2'-O-alkyl nucleotide;

(c) each pyrimidine nucleotide in $N_{X3}$ positions is independently a 2'-deoxy-2'-fluoro nucleotide; and (d) each purine nucleotide in $N_{X3}$ positions is independently a ribonucleotide.

In one embodiment, the invention features a double-stranded short interfering nucleic acid (siNA) of formula (A); wherein (a) each pyrimidine nucleotide in $N_{X4}$ positions is independently a 2'-deoxy-2'-fluoro nucleotide;

(b) each purine nucleotide in $N_{X4}$ positions is independently a ribonucleotide;

(c) each pyrimidine nucleotide in $N_{X3}$ positions is independently a 2'-deoxy-2'-fluoro nucleotide; and (d) each purine nucleotide in $N_{X3}$ positions is independently a ribonucleotide.

In yet another embodiment, the invention provides a double stranded short interfering nucleic acid (siNA) molecule wherein the siNA is:

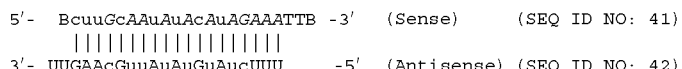

```
5'-  BcuuGcAAuAuAcAuAGAAATTB  -3'    (Sense)     (SEQ ID NO: 41)
     ||||||||||||||||||||
3'-  UUGAAcGuuAuAuGuAucUUU    -5'    (Antisense) (SEQ ID NO: 42)
``` wherein:

each B is an inverted abasic cap moiety;

c is 2'-deoxy-2'fluorocytidine;

u is 2'-deoxy-2'fluorouridine;

A is 2'-deoxyadenosine;

G is 2'-deoxyguanosine;

T is thymidine;

U is uridine;

<u>A</u> is 2'-O-methyl-adenosine;

<u>G</u> is 2'-O-methyl-guanosine;

<u>U</u> is 2'-O-methyl-uridine; and the internucleotide linkages are chemically modified or unmodified.

In yet another embodiment, the invention provides a double stranded short interfering nucleic acid (siNA) molecule wherein the siNA is:

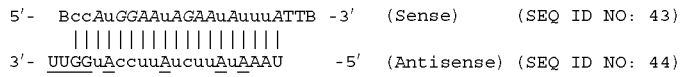

```
5'-  BccAuGGAAuAGAAuAuuuATTB  -3'    (Sense)     (SEQ ID NO: 43)
     ||||||||||||||||||||
3'-  UUGGuAccuuAucuuAuAAAU    -5'    (Antisense) (SEQ ID NO: 44)
``` wherein:

each B is an inverted abasic cap;

c is 2'-deoxy-2'fluorocytidine;

u is 2'-deoxy-2'fluorouridine;

A is 2'-deoxyadenosine;

G is 2'-deoxyguanosine;

T is thymidine;

A is adenosine;

U is uridine;

<u>A</u> is 2'-O-methyl-adenosine;

<u>G</u> is 2'-O-methyl-guanosine;

<u>U</u> is 2'-O-methyl-uridine; and the internucleotide linkages are chemically modified or unmodified.

In yet another embodiment, the invention provides a double stranded short interfering nucleic acid (siNA) molecule wherein the siNA is:

```
5'   BcccucAAcAuuAcuGuAAuTTB   3'  (Sense)     (SEQ ID NO: 47)
        |||||||||||||||||||
3'   UUGGGAGuuGuAAuGAcAUUA     5'  (Antisense) (SEQ ID NO: 48)
``` wherein:
  each B is an inverted abasic cap moiety;
  c is 2'-deoxy-2'fluorocytidine;
  u is 2'-deoxy-2'fluorouridine;
  A is 2'-deoxyadenosine;
  G is 2'-deoxyguanosine;
  T is thymidine;
  A is adenosine;
  U is uridine;
  A is 2'-O-methyl-adenosine;
  G is 2'-O-methyl-guanosine;
  U is 2'-O-methyl-uridine; and
  the internucleotide linkages are chemically modified or unmodified.

In yet another embodiment, the invention provides a double stranded short interfering nucleic acid (siNA) molecule wherein the siNA is:

```
5'-  BucAGcAccAAcAAGuuAAuTTB  -3'  (Sense)     (SEQ ID NO: 53)
        |||||||||||||||||||
  3'   UUAGucGuGGuuGuucAAUUA  -5'  (Antisense) (SEQ ID NO: 54)
``` wherein:
  each B is an inverted abasic cap moiety;
  c is 2'-deoxy-2'fluorocytidine;
  u is 2'-deoxy-2'fluorouridine;
  A is 2'-deoxyadenosine;
  G is 2'-deoxyguanosine;
  T is thymidine;
  A is adenosine;
  U is uridine;
  A is 2'-O-methyl-adenosine;
  G is 2'-O-methyl-guanosine;
  U is 2'-O-methyl-uridine; and
  the internucleotide linkages are chemically modified or unmodified.

In yet another embodiment, the invention provides a double stranded short interfering nucleic acid (siNA) molecule wherein the siNA is:

```
5'-  BAcAGGAuuAuuuAucucAATTB  -3'  (Sense)     (SEQ ID NO: 55)
        |||||||||||||||||||
  3'   UUuGuccuAAuAAAuAGAGUU  -5'  (Antisense) (SEQ ID NO: 56)
``` wherein:
  each B is an inverted abasic cap moiety;
  c is 2'-deoxy-2'fluorocytidine;
  u is 2'-deoxy-2'fluorouridine;
  A is 2'-deoxyadenosine;
  G is 2'-deoxyguanosine;
  T is thymidine;
  G is guanosine;
  U is uridine;
  A is 2'-O-methyl-adenosine;
  G is 2'-O-methyl-guanosine;
  U is 2'-O-methyl-uridine; and
  the internucleotide linkages are chemically modified or unmodified.

In yet another embodiment, the invention provides a double stranded short interfering nucleic acid (siNA) molecule wherein the siNA is:

```
5'-  BuGGuGGuGAuucuGuuuGcTTB  -3'  (Sense)     (SEQ ID NO: 71)
        |||||||||||||||||||
  3'   UUAccAccAcuAAGAcAAACG  -5'  (Antisense) (SEQ ID NO: 72)
``` wherein:
  each B is an inverted abasic cap moiety;
  c is 2'-deoxy-2'fluorocytidine;
  u is 2'-deoxy-2'fluorouridine;
  A is 2'-deoxyadenosine;
  G is 2'-deoxyguanosine;
  T is thymidine;
  G is guanosine;
  A is adenosine;
  C is cytidine;
  A is 2'-O-methyl-adenosine;

G is 2'-O-methyl-guanosine;

$\overline{U}$ is 2'-O-methyl-uridine; and the internucleotide linkages are chemically modified or unmodified.

The present invention further provides pharmaceutical compositions comprising the double-stranded nucleic acids molecules described herein and optionally a pharmaceutically acceptable carrier.

The administration of the pharmaceutical composition may be carried out by known methods, wherein the nucleic acid is introduced into a desired target cell in vitro or in vivo.

Commonly used techniques for introduction of the nucleic acid molecules of the invention into cells, tissues, and organisms include the use of various carrier systems, reagents and vectors. Non-limiting examples of such carrier systems suitable for use in the present invention include nucleic-acid-lipid particles, lipid nanoparticles (LNP), liposomes, lipoplexes, micelles, virosomes, virus like particles (VLP), nucleic acid complexes, and mixtures thereof.

The pharmaceutical compositions may be in the form of an aerosol, dispersion, solution (e.g., an injectable solution), a cream, ointment, tablet, powder, suspension or the like. These compositions may be administered in any suitable way, e.g. orally, sublingually, buccally, parenterally, nasally, or topically. In some embodiments, the compositions are aerosolized and delivered via inhalation.

The molecules and pharmaceutical compositions of the present invention have utility over a broad range of therapeutic applications, accordingly another aspect of this invention relates to the use of the compounds and pharmaceutical compositions of the invention in treating a subject. The invention thus provides a method for treating a subject, such as a human, suffering from a condition which is mediated by the action, or by the loss of action, of FCεR1α, wherein the method comprises administering to the subject an effective amount of a double-stranded short interfering nucleic acid (siNA) molecule of the invention. In certain embodiments, the condition is a respiratory disease such as, for example, but not limitation, COPD, cystic fibrosis, asthma, eosinophilic cough, bronchitis, sarcoidosis, pulmonary fibrosis, rhinitis, and sinusitis.

These and other aspects of the invention will be apparent upon reference to the following detailed description and attached figures. To that end, patents, patent applications, and other documents are cited throughout the specification to describe and more specifically set forth various aspects of this invention. Each of these references cited herein is hereby incorporated by reference in its entirety, including the drawings.

BRIEF DESCRIPTION OF THE DRAWINGS

FIG. 2A: The sense strand comprises 21 nucleotides wherein the two terminal 3'-nucleotides are optionally base paired and wherein all nucleotides present are ribonucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety wherein the two terminal 3'-nucleotides are optionally complementary to the target RNA sequence, and wherein all nucleotides present are ribonucleotides except for (N N) nucleotides, which can comprise ribonucleotides, deoxynucleotides, universal bases, or other chemical modifications described herein. A modified internucleotide linkage, such as a phosphorothioate, phosphorodithioate, phosphonoacetate, thiophosphonoacetate or other modified internucleotide linkage as described herein, shown as "s", optionally connects the (N N) nucleotides in the antisense strand.

FIG. 2B: The sense strand comprises 21 nucleotides wherein the two terminal 3'-nucleotides are optionally base paired and wherein all pyrimidine nucleotides that can be present are 2'deoxy-2'-fluoro modified nucleotides and all purine nucleotides that can be present are 2'-O-methyl modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that can be present are 2'-deoxy-2'-fluoro modified nucleotides and all purine nucleotides that can be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the sense and antisense strand.

FIG. 2C: The sense strand comprises 21 nucleotides having 5'- and 3'-terminal caps wherein the two terminal 3'-nucleotides are optionally base paired and wherein all pyrimidine nucleotides that can be present are 2'-O-methyl or 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that can be present are 2'-deoxy-2'-fluoro modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 2D: The sense strand comprises 21 nucleotides having 5'- and 3'-terminal caps wherein the two terminal 3'-nucleotides are optionally base paired and wherein all pyrimidine nucleotides that can be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that can be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, wherein all pyrimidine nucleotides that can be present are 2'-deoxy-2'-fluoro modified nucleotides and all purine nucleotides that can be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 2E: The sense strand comprises 21 nucleotides having 5'- and 3'-terminal caps wherein the two terminal 3'-nucleotides are optionally base paired and wherein all pyrimidine nucleotides that can be present are 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that can be present are 2'-deoxy-2'-fluoro modified nucleotides and all purine nucleotides that can be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 2F: The sense strand comprises 21 nucleotides having 5'- and 3'-terminal caps wherein the two terminal 3'-nucleotides are optionally base paired and wherein all pyrimidine nucleotides that can be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that can be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, and having one 3'-terminal phosphorothioate internucleotide linkage and wherein all pyrimidine nucleotides that can be present are 2'-deoxy-2'-fluoro modified nucleotides and all purine nucleotides that can be present are 2'-deoxy nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s", optionally connects the (N N) nucleotides in the antisense strand.

FIG. 4A-C shows non-limiting examples of different siNA constructs of the invention.

Figure 4A:
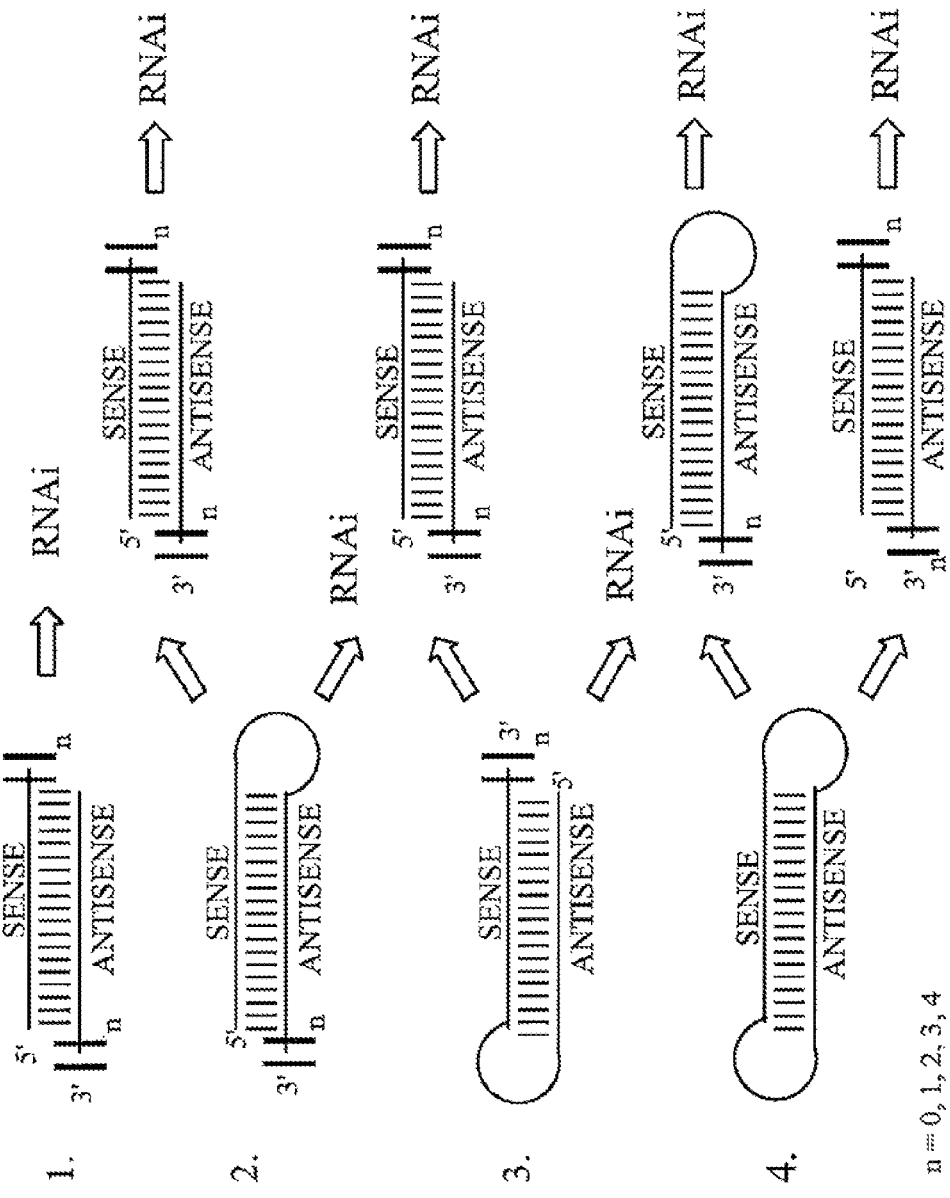

The examples shown in FIG. 4A (constructs 1, 2, and 3) have 19 representative base pairs; however, different embodiments of the invention include any number of base pairs described herein. Bracketed regions represent nucleotide overhangs, for example, comprising about 1, 2, 3, or 4 nucleotides in length, preferably about 2 nucleotides. Constructs 1 and 2 can be used independently for RNAi activity. Construct 2 can comprise a polynucleotide or non-nucleotide linker, which can optionally be designed as a biodegradable linker. In one embodiment, the loop structure shown in construct 2 can comprise a biodegradable linker that results in the formation of construct 1 in vivo and/or in vitro. In another example, construct 3 can be used to generate construct 2 under the same principle wherein a linker is used to generate the active siNA construct 2 in vivo and/or in vitro, which can optionally utilize another biodegradable linker to generate the active siNA construct 1 in vivo and/or in vitro. As such, the stability and/or activity of the siNA constructs can be modulated based on the design of the siNA construct for use in vivo or in vitro and/or in vitro.

Figure 4B:
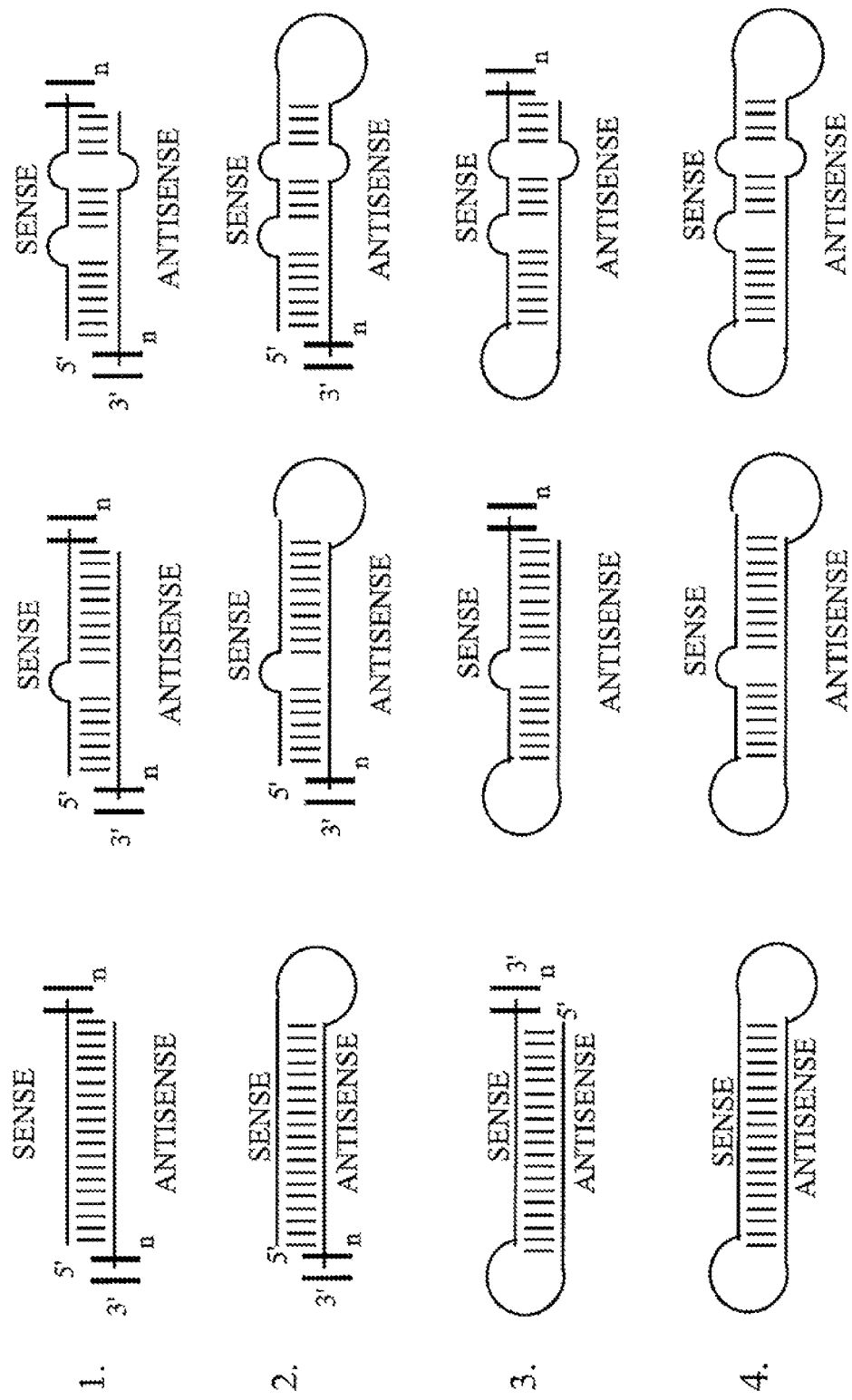

The examples shown in FIG. 4B represent different variations of double-stranded nucleic acid molecule of the invention, such as microRNA, that can include overhangs, bulges, loops, and stem-loops resulting from partial complementarity. Such motifs having bulges, loops, and stem-loops are generally characteristics of miRNA. The bulges, loops, and stem-loops can result from any degree of partial complementarity, such as mismatches or bulges of about 1, 2, 3, 4, 5, 6, 7, 8, 9, 10 or more nucleotides in one or both strands of the double-stranded nucleic acid molecule of the invention.

The example shown in FIG. 4C represents a model double-stranded nucleic acid molecule of the invention comprising a 19 base pair duplex of two 21 nucleotide sequences having dinucleotide 3'-overhangs. The top strand (1) represents the sense strand (passenger strand), the middle strand (2) represents the antisense (guide strand), and the lower strand (3) represents a target polynucleotide sequence. The dinucleotide overhangs (NN) can comprise a sequence derived from the target polynucleotide. For example, the 3'-(NN) sequence in the guide strand can be complementary to the 5'-[NN] sequence of the target polynucleotide. In addition, the 5'-(NN) sequence of the passenger strand can comprise the same sequence as the 5'-[NN] sequence of the target polynucleotide sequence. In other embodiments, the overhangs (NN) are not derived from the target polynucleotide sequence, for example where the 3'-(NN) sequence in the guide strand are not complementary to the 5'-[NN] sequence of the target polynucleotide and the 5'-(NN) sequence of the passenger strand can comprise different sequence from the 5'-[NN] sequence of the target polynucleotide sequence. In additional embodiments, any (NN) nucleotides are chemically modified, e.g., as 2'-O-methyl, 2'-deoxy-2'-fluoro, and/or other modifications herein. Furthermore, the passenger strand can comprise a ribonucleotide position N of the passenger strand. For the representative 19 base pair 21 mer duplex shown, position N can be 9 nucleotides in from the 3' end of the passenger strand. However, in duplexes of differing length, the position N is determined based on the 5'-end of the guide strand by counting 11 nucleotide positions in from the 5'-terminus of the guide strand and picking the corresponding base paired nucleotide in the passenger strand. Cleavage by Ago2 takes place between positions 10 and 11 as indicated by the arrow. In additional embodiments, there are two ribonucleotides, NN, at positions 10 and 11 based on the 5'-end of the guide strand by counting 10 and 11 nucleotide positions in from the 5'-terminus of the guide strand and picking the corresponding base paired nucleotides in the passenger strand.

Figure 5:
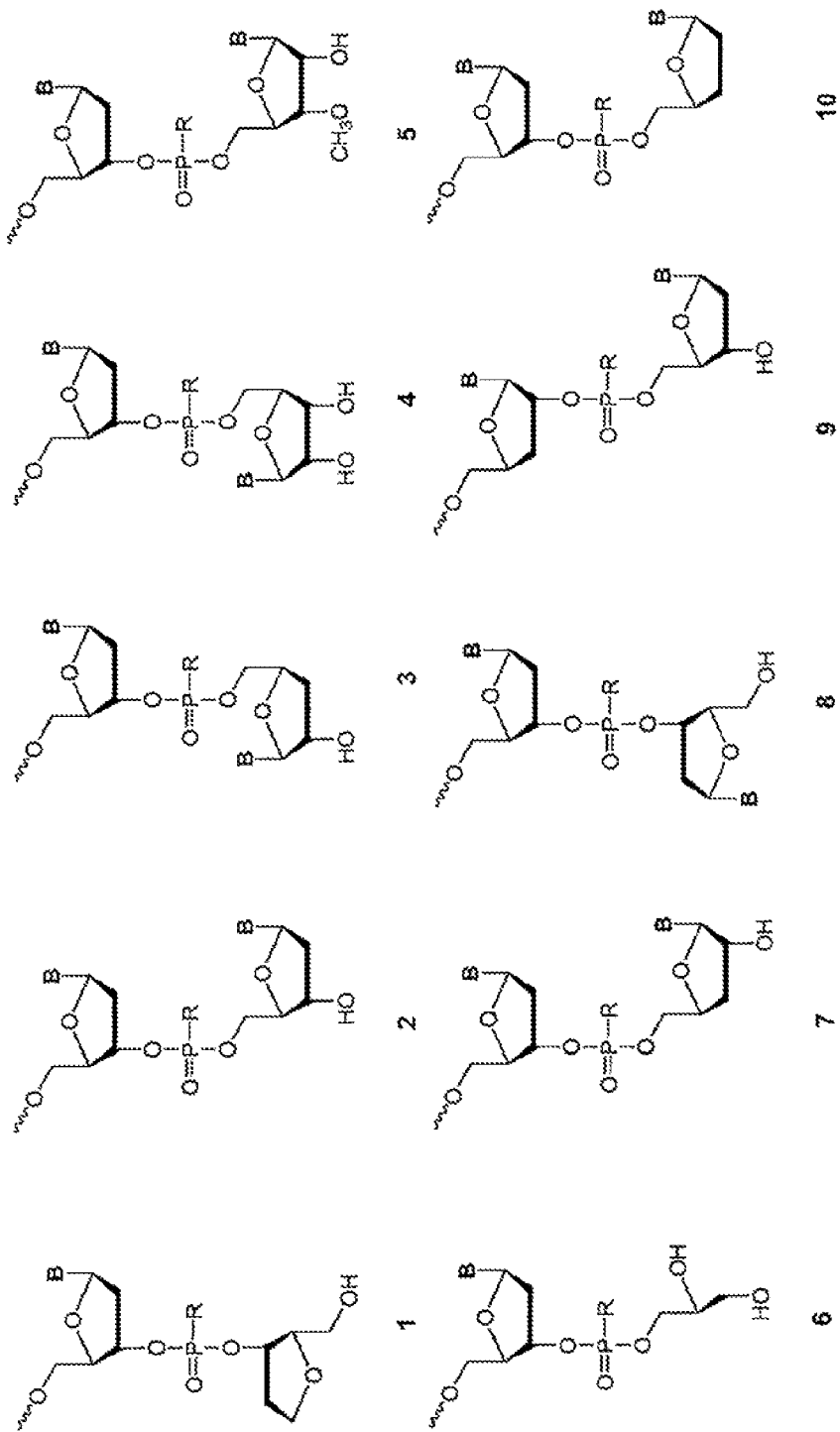

FIG. 5 shows non-limiting examples of different stabilization chemistries (1-10) that can be used, for example, to stabilize the 5' and/or 3'-ends of siNA sequences of the invention, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to modified and unmodified backbone chemistries indicated in the figure, these chemistries can be combined with different sugar and base nucleotide modifications as described herein.

Figure 6:
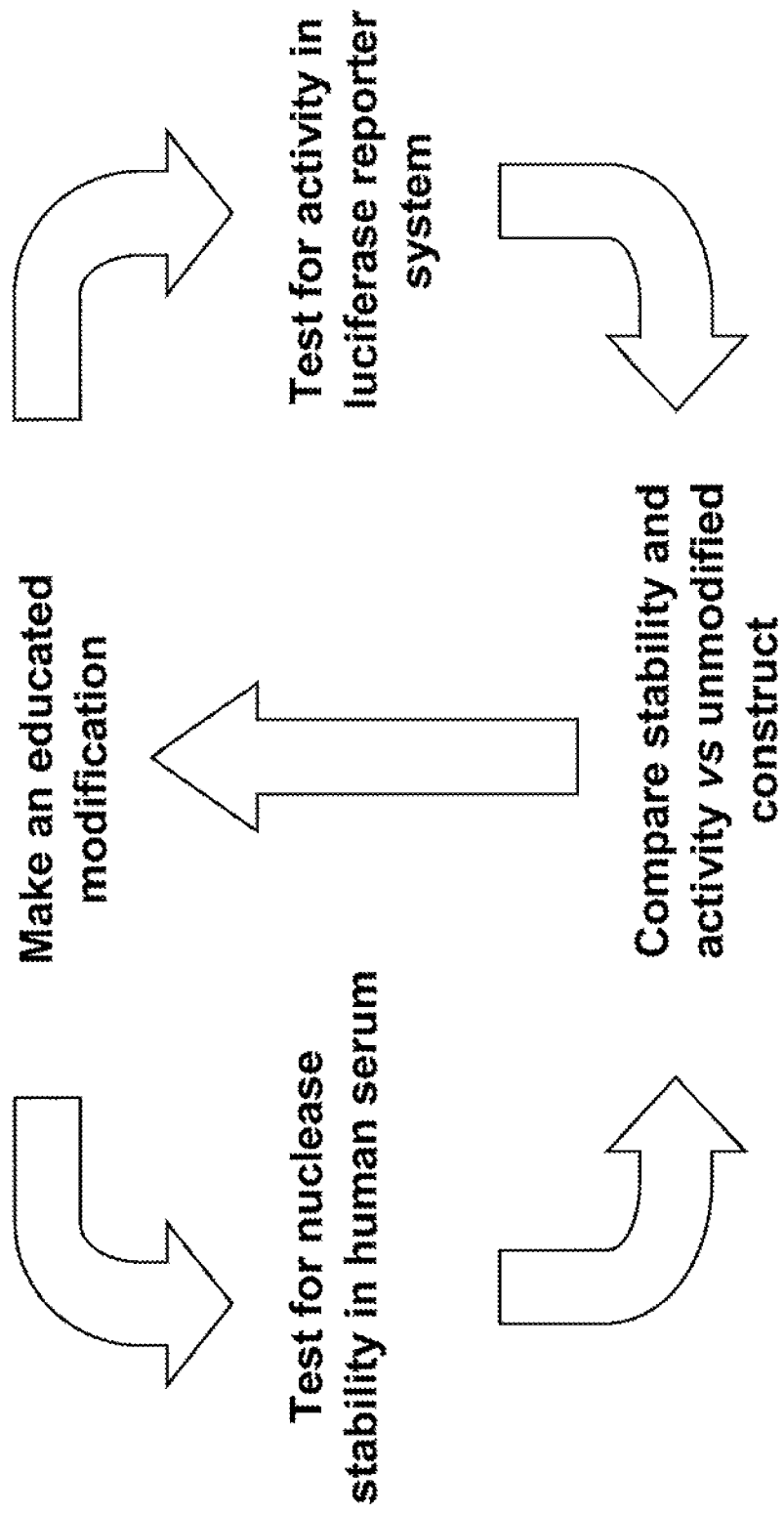

FIG. 6 shows a non-limiting example of a strategy used to identify chemically modified siNA constructs of the invention that are nuclease resistant while preserving the ability to mediate RNAi activity. Chemical modifications are introduced into the siNA construct based on educated design parameters (e.g. introducing 2'-modifications, base modifications, backbone modifications, terminal cap modifications etc). The modified construct is tested in an appropriate system (e.g., human serum for nuclease resistance, shown, or an animal model for PK/delivery parameters). In parallel, the siNA construct is tested for RNAi activity, for example in a cell culture system such as a luciferase reporter assay). Lead siNA constructs are then identified which possess a particular characteristic while maintaining RNAi activity, and can be further modified and assayed once again. This same approach can be used to identify siNA-conjugate molecules with improved pharmacokinetic profiles, delivery, and RNAi activity.

Figure 7:
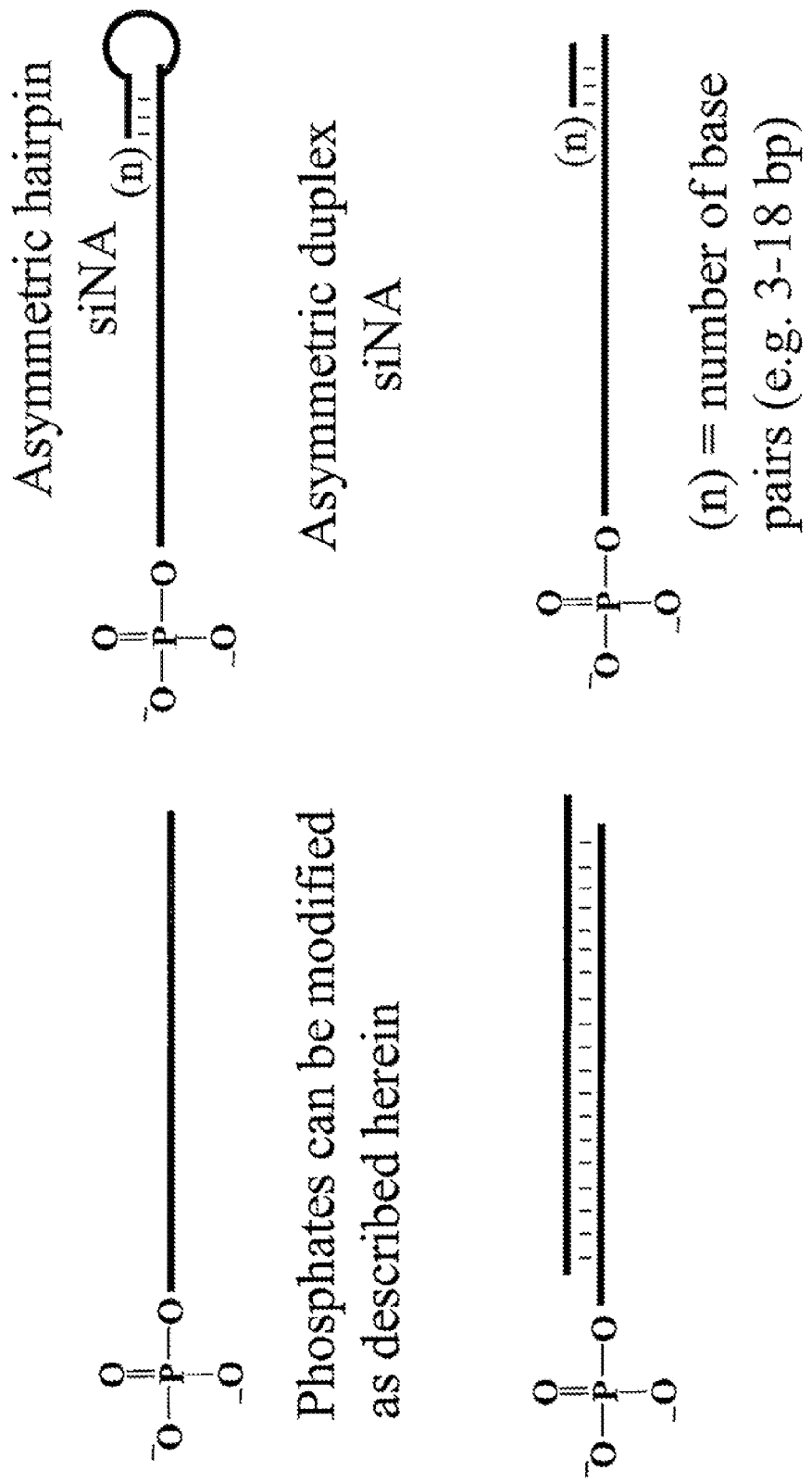

FIG. 7 shows non-limiting examples of phosphorylated siNA molecules of the invention, including linear and duplex constructs and asymmetric derivatives thereof.

Figure 8:
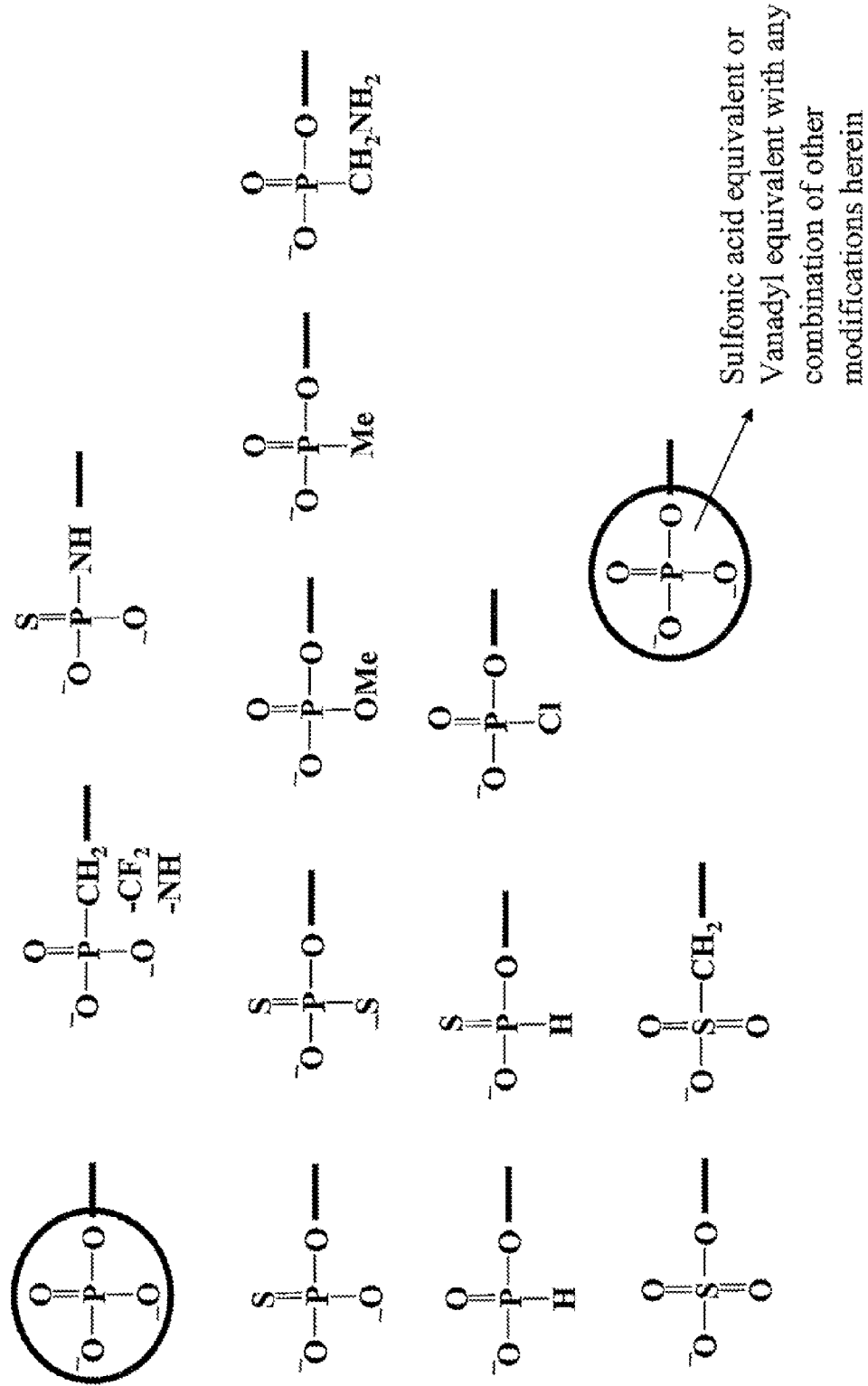

FIG. 8 shows non-limiting examples of chemically modified terminal phosphate groups of the invention.

Figure 9:
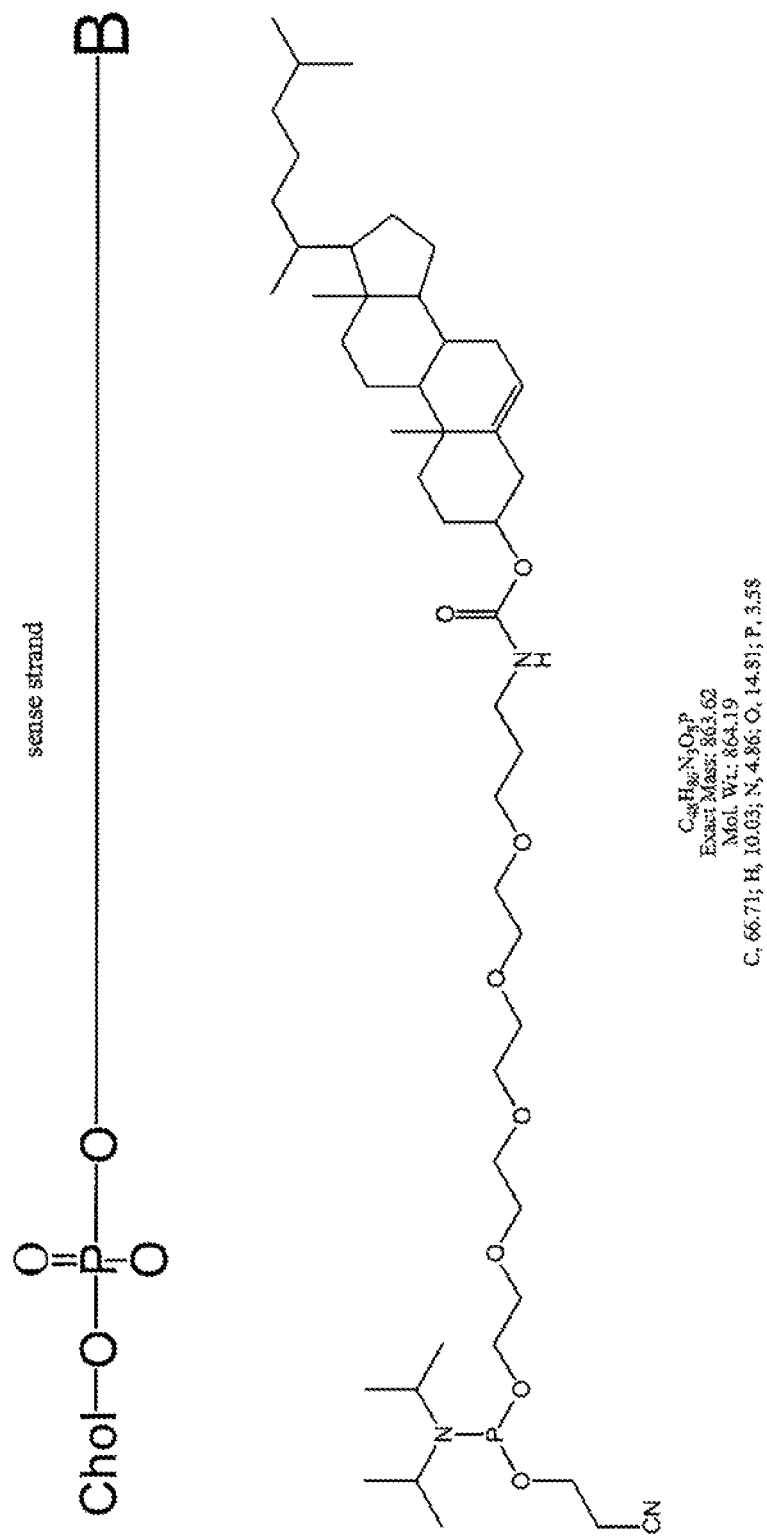

FIG. 9 shows a non-limiting example of a cholesterol linked phosphoramidite that can be used to synthesize cholesterol conjugated siNA molecules of the invention. An example is shown with the cholesterol moiety linked to the 5'-end of the sense strand of an siNA molecule.

Figure 10:
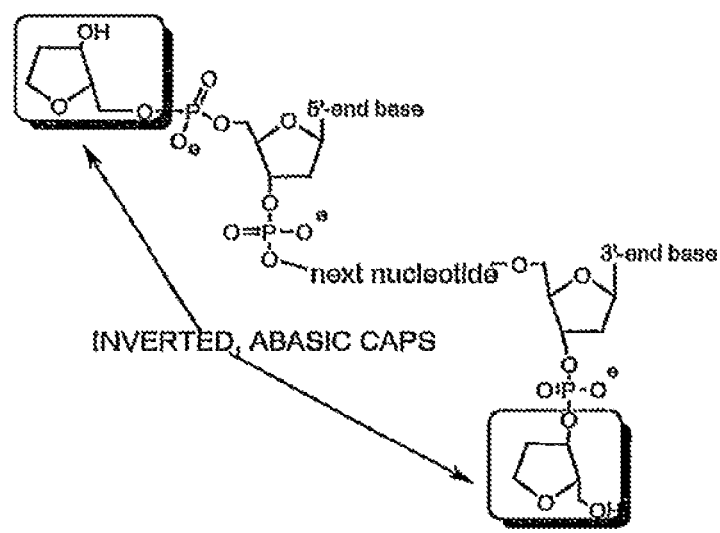

FIG. 10 depicts an embodiment of 5' and 3' inverted abasic cap linked to a nucleic acid strand.

DETAILED DESCRIPTION OF THE INVENTION

A. Terms and Definitions

The following terminology and definitions apply as used in the present application.

The term "abasic" refers to sugar moieties lacking a nucleobase or having a hydrogen atom (H) or other non-nucleobase chemical groups in place of a nucleobase at the 1' position of the sugar moiety, see for example Adamic et al., U.S. Pat. No. 5,998,203. In one embodiment, an abasic moiety of the invention is a ribose, deoxyribose, or dideoxyribose sugar.

The term "acyclic nucleotide" as used herein refers to any nucleotide having an acyclic ribose sugar, for example where any of the ribose carbon/carbon or carbon/oxygen bonds are independently or in combination absent from the nucleotide.

The term "alkyl" refers to a saturated or unsaturated hydrocarbons, including straight-chain, branched-chain, alkenyl, alkynyl groups and cyclic groups, but excludes aromatic groups. Notwithstanding the foregoing, alkyl also refers to non-aromatic heterocyclic groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted the substituted group(s) is preferably, hydroxyl, cyano, C1-C4alkoxy, =O, =S, $NO_2$, SH, $NH_2$, or $NR_1R_2$, where $R_1$ and $R_2$ independently are H or C1-C4 alkyl The term "aryl" refers to an aromatic group that has at least one ring having a conjugated pi electron system and includes carbocyclic aryl, heterocyclic aryl and biaryl groups, all of which can be optionally substituted. The preferred substituent(s) of aryl groups are halogen, trihalomethyl, hydroxyl, SH, OH, cyano, C1-C4alkoxy, C1-C4alkyl, C2-C4alkenyl, C2-C4alkynyl, $NH_2$, and $NR_1R_2$ groups, where $R_1$ and $R_2$ independently are H or C1-C4 alkyl.

The term "alkylaryl" refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and examples of heterocyclic aryl groups having such heteroatoms include furanyl, thienyl, pyridyl, pyrrolyl, N-lower alkyl pyrrolo, pyrimidyl, pyrazinyl, imidazolyl and the like, all optionally substituted. Preferably, the alkyl group is a C1-C4alkyl group.

The term "amide" refers to an —C(O)—NH—R, where R is either alkyl, aryl, alkylaryl or hydrogen.

The phrase "antisense region" refers to a nucleotide sequence of an siNA molecule having complementarity to a target nucleic acid sequence. In addition, the antisense region of an siNA molecule can optionally comprise a nucleic acid sequence having complementarity to a sense region of the siNA molecule. In one embodiment, the antisense region of the siNA molecule is referred to as the antisense strand or guide strand.

The phrase "asymmetric hairpin" refers to a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

The term "biodegradable" refers to degradation in a biological system, for example, enzymatic degradation or chemical degradation.

The term "biodegradable linker" refers to a nucleic acid or non-nucleic acid linker molecule that is designed to connect one molecule to another molecule, for example, a biologically active molecule to an siNA molecule of the invention or the sense and antisense strands of an siNA molecule of the invention, and is biodegradable. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The phrase "biologically active molecule" refers to compounds or molecules that are capable of eliciting or modifying a biological response in a system and/or are capable of modulating the pharmacokinetics and/or pharmacodynamics of other biologically active molecules, Non-limiting examples of biologically active molecules, include siNA molecules alone or in combination with other molecules including, but not limited to therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, polyamines, polyamides, polyethylene glycol, other polyethers, 0.2-5A chimeras, siNA, dsRNA, allozymes, aptamers, decoys and analogs thereof.

The phrase "biological system" refers to material, in a purified or unpurified form, from biological sources including, but not limited to human or animal, wherein the system comprises the components required for RNAi activity. Thus, the phrase includes, for example, a cell, tissue, subject, or organism, or extract thereof. The term also includes reconstituted material from a biological source.

The phrase "blunt end" refers to a termini of a double-stranded siNA molecule having no overhanging nucleotides. The two strands of a double-stranded siNA molecule align with each other without over-hanging nucleotides at the termini.

The term "cap" also referred to herein as "terminal cap," refers to chemical modifications, which can be incorporated at either 5' or 3' terminus of the oligonucleotide of either the sense or the antisense strand (see, for example, Adamic et al., U.S. Pat. No. 5,998,203, incorporated by reference herein). These terminal modifications protect the nucleic acid molecule from exonuclease degradation, and can help in delivery and/or localization within a cell. The cap can be present at the 5'-terminus (5'-cap) or at the 3'-terminal (3'-cap) or can be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein). FIG. 5 shows some non-limiting examples of various caps.

The term "cell" is used in its usual biological sense, and does not refer to an entire multicellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The phrase "chemical modification" refer to any modification of the chemical structure of the nucleotides that differs from nucleotides of native siRNA or RNA. The term "chemical modification" encompasses the addition, substitution, or modification of native siRNA or RNA at the sugar, base, or internucleotide linkage, as described herein or as is otherwise known in the art. See for example, U.S. Ser. No. 12/064,014 for non-limiting examples of chemical modifications that are compatible with the nucleic acid molecules of the present invention.

The term "complementarity" refers to the formation of hydrogen bond(s) between one nucleic acid sequence and another nucleic acid sequence by either traditional Watson-Crick or other non-traditional types of bonding as described herein. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). Perfect complementary means that all the contiguous residues of a nucleic acid sequence will hydrogen bond with the same number of contiguous residues in a second nucleic acid sequence. Partial complementarity can include various mismatches or non-based paired nucleotides (e.g., 1, 2, 3, 4, 5, 6, 7, 8, 9, or more mismatches or non-based paired nucleotides) within the nucleic acid molecule, which can result in bulges, loops, or overhangs that result between the sense strand or sense region and the antisense strand or antisense region of the nucleic acid molecule or between the antisense strand or antisense region of the nucleic acid molecule and a corresponding target nucleic acid molecule.

The term "FCεR1α" refers to the high affinity IgE receptor alpha chain gene, or to the genes that encode FCεR1α proteins, FCεR1α peptides, FCεR1α polypeptides, FCεR1α regulatory polynucleotides (e.g., FCεR1α miRNAs and siRNAs), mutant FCεR1α genes, and splice variants of FCεR1α genes, as well as other genes involved in FCεR1α pathways of gene expression and/or activity. Thus, each of the embodiments described herein with reference to the term "FCεR1α" are applicable to all of the protein, peptide, polypeptide, and/or polynucleotide molecules covered by the term "FCεR1α", as that term is defined herein. Comprehensively, such gene targets are also referred to herein generally as "target" sequences (including Table 7).

The term "gene" or phrase "target gene" refer to a nucleic acid (e.g., DNA or RNA) sequence that comprises partial length or entire length coding sequences necessary for the production of a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Aberrant fRNA or ncRNA activity leading to disease can therefore be modulated by siNA molecules of the invention. siNA molecules targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, Science, 300, 258-260.

The phrase "homologous sequence" refers to a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes, such as a cytokine and its corresponding receptors. A homologous sequence can be a nucleotide sequence that is shared by two or more non-coding polynucleotides, such as noncoding DNA or RNA, regulatory sequences, introns, and sites of transcriptional control or regulation. Homologous sequences can also include sequence regions shared by more than one polynucleotide sequence. Homology does not need to be perfect identity (100%), as partially homologous sequences are also contemplated by and within the scope of the instant invention (e.g., at least 95%, 94%, 93%, 92%, 91%, 90%, 89%, 88%, 87%, 86%, 85%, 84%, 83%, 82%, 81%, 80% etc.). Percent homology is the number of matching nucleotides between two sequences divided by the total length being compared multiplied by 100.

The phrase "improved RNAi activity" refer to an increase in RNAi activity measured in vitro and/or in vivo, where the RNAi activity is a reflection of both the ability of the siNA to mediate RNAi and the stability of the siNAs of the invention. In this invention, the product of these activities can be increased in vitro and/or in vivo compared to an all RNA siRNA or an siNA containing a plurality of ribonucleotides. In some cases, the activity or stability of the siNA molecule can be decreased (i.e., less than ten-fold), but the overall activity of the siNA molecule is enhanced in vitro and/or in vivo.

The terms "inhibit", "down-regulate", or "reduce", refer to the reduction in the expression of the gene, or level of RNA molecules or equivalent RNA molecules encoding one or more proteins or protein subunits, or activity of one or more proteins or protein subunits, below that observed in the absence of the nucleic acid molecules (e.g., siNA) of the invention. Down-regulation can also be associated with post-transcriptional silencing, such as, RNAi mediated cleavage or by alteration in DNA methylation patterns or DNA chromatin structure. Inhibition, down-regulation or reduction with an siNA molecule can be in reference to an inactive molecule, an attenuated molecule, an siNA molecule with a scrambled sequence, or an siNA molecule with mismatches or alternatively, it can be in reference to the system in the absence of the nucleic acid.

The terms "mammalian" or "mammal" refer to any warm blooded vertebrate species, such as a human, mouse, rat, dog, cat, hamster, guinea pig, rabbit, livestock, and the like.

The phrase "metered dose inhaler" or MDI refers to a unit comprising a can, a secured cap covering the can and a formulation metering valve situated in the cap. MDI systems includes a suitable channeling device. Suitable channeling devices comprise for example, a valve actuator and a cylindrical or cone-like passage through which medicament can be delivered from the filled canister via the metering valve to the nose or mouth of a patient such as a mouthpiece actuator.

The term "microRNA" or "miRNA" refers to a small double-stranded RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research, 102, 3-9; He et al., 2004, Nat. Rev. Genet., 5, 522-531; Ying et al., 2004, Gene, 342, 25-28; and Sethupathy et al., 2006, RNA, 12:192-197).

The term "modulate" means that the expression of the gene, or level of a RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

The phrase "modified nucleotide" refers to a nucleotide, which contains a modification in the chemical structure of the base, sugar and/or phosphate of the unmodified (or natural) nucleotide. Non-limiting examples of modified nucleotides are described herein and in U.S. Ser. No. 12/064,014.

The phrase "non-base paired" refers to nucleotides that are not base paired between the sense strand or sense region and the antisense strand or antisense region of an double-stranded siNA molecule; and can include for example, but not limitation, mismatches, overhangs, single stranded loops, etc.

The term "non-nucleotide" refers to any group or compound which can be incorporated into a nucleic acid chain in the place of one or more nucleotide units, such as abasic moieties. The group or compound is "abasic" in that it does not contain a commonly recognized nucleotide base, such as adenosine, guanine, cytosine, uracil or thymine and therefore lacks a nucleobase at the 1'-position.

The term "nucleotide" is used as is recognized in the art. Nucleotides generally comprise a base, a sugar, and a phosphate moiety. The base can be a. natural bases (standard) or modified bases as are well known in the art. Such bases are generally located at the 1' position of a nucleotide sugar moiety. Additionally, the nucleotides can be unmodified or modified at the sugar, phosphate and/or base moiety, (also referred to interchangeably as nucleotide analogs, modified nucleotides, non-natural nucleotides, non-standard nucleotides and other; see, for example, U.S. Ser. No. 12/064,014.

The term "overhang" refers to the terminal portion of the nucleotide sequence that is not base paired between the two strands of a double-stranded nucleic acid molecule (see for example, FIG. 4).

The term "parenteral" refers administered in a manner other than through the digestive tract, and includes epicutaneous, subcutaneous, intravascular (e.g., intravenous), intramuscular, or intrathecal injection or infusion techniques and the like.

The phrase "pathway target" refers to any target involved in pathways of gene expression or activity. For example, any given target can have related pathway targets that can include upstream, downstream, or modifier genes in a biologic pathway. These pathway target genes can provide additive or synergistic effects in the treatment of diseases, conditions, and traits herein.

A "pharmaceutical composition" or "pharmaceutical formulation" refers to a composition or formulation in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, pharmaceutical compositions injected into the blood stream should be soluble. Other factors are known in the art, and include considerations such as toxicity and forms that prevent the composition or formulation from exerting its effect. As used herein, pharmaceutical formulations include formulations for human and veterinary use. Non-limiting examples of agents suitable for formulation with the nucleic acid molecules of the instant invention include: P-glycoprotein inhibitors (such as Pluronic P85); biodegradable polymers, such as poly(DL-lactide-coglycolide) microspheres for sustained release delivery (Emerich, D F et al, 1999, *Cell Transplant*, 8, 47-58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058. A "pharmaceutically acceptable composition" or "pharmaceutically acceptable formulation" refer to a composition or formulation that allows for the effective distribution of the nucleic acid molecules of the instant invention in the physical location most suitable for their desired activity.

The term "phosphorothioate" refers to an internucleotide phosphate linkage comprising one or more sulfur atoms in place of an oxygen atom. Hence, the term phosphorothioate refers to both phosphorothioate and phosphorodithioate internucleotide linkages.

The term "ribonucleotide" refers to a nucleotide with a hydroxyl group at the 2' position of a β-D-ribofuranose moiety.

The term "RNA" refers to a molecule comprising at least one ribofuranoside moiety. The term includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "RNA interference" or term "RNAi" refer to the biological process of inhibiting or down regulating gene expression in a cell, as is generally known in the art, and which is mediated by short interfering nucleic acid molecules, see for example Zamore and Haley, 2005, *Science*, 309, 1519-1524; Vaughn and Martienssen, 2005, *Science*, 309, 1525-1526; Zamore et al., 2000, *Cell*, 101, 25-33; Bass, 2001, *Nature*, 411, 428-429; Elbashir et al., 2001, *Nature*, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-

2237; Hutvagner and Zamore, 2002, *Science,* 297, 2056-60; McManus et al., 2002, *RNA,* 8, 842-850; Reinhart et al., 2002, *Gene & Dev.,* 16, 1616-1626; and Reinhart & Bartel, 2002, *Science,* 297, 1831). Additionally, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at either the post-transcriptional level or the pre-transcriptional level. In a non-limiting example, epigenetic modulation of gene expression by siNA molecules of the invention can result from siNA mediated modification of chromatin structure or methylation patterns to alter gene expression (see, for example, Verdel et al., 2004, *Science,* 303, 672-676; Pal-Bhadra et al., 2004, *Science,* 303, 669-672; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). In another non-limiting example, modulation of gene expression by siNA molecules of the invention can result from siNA mediated cleavage of RNA (either coding or non-coding RNA) via RISC, or via translational inhibition, as is known in the art or modulation can result from transcriptional inhibition (see for example Janowski et al., 2005, *Nature Chemical Biology,* 1, 216-222).

The phrase "RNAi inhibitor" refers to any molecule that can down regulate, reduce or inhibit RNA interference function or activity in a cell or organism. An RNAi inhibitor can down regulate, reduce or inhibit RNAi (e.g., RNAi mediated cleavage of a target polynucleotide, translational inhibition, or transcriptional silencing) by interaction with or interfering the function of any component of the RNAi pathway, including protein components such as RISC, or nucleic acid components such as miRNAs or siRNAs. A RNAi inhibitor can be an siNA molecule, an antisense molecule, an aptamer, or a small molecule that interacts with or interferes with the function of RISC, a miRNA, or an siRNA or any other component of the RNAi pathway in a cell or organism. By inhibiting RNAi (e.g., RNAi mediated cleavage of a target polynucleotide, translational inhibition, or transcriptional silencing), a RNAi inhibitor of the invention can be used to modulate (e.g., up-regulate or down regulate) the expression of a target gene.

The phrase "sense region" refers to nucleotide sequence of an siNA molecule having complementarity to an antisense region of the siNA molecule. In addition, the sense region of an siNA molecule can comprise a nucleic acid sequence having homology with a target nucleic acid sequence. The sense region of the siNA molecule can also refer to as the sense strand or passenger strand.

The phrases "short interfering nucleic acid", "siNA", "short interfering RNA", "siRNA", "short interfering nucleic acid molecule", "short interfering oligonucleotide molecule", or "chemically modified short interfering nucleic acid molecule" refer to any nucleic acid molecule capable of inhibiting or down regulating gene expression or viral replication by mediating RNA interference "RNAi" or gene silencing in a sequence-specific manner. These terms can refer to both individual nucleic acid molecules, a plurality of such nucleic acid molecules, or pools of such nucleic acid molecules. The siNA can be a double-stranded nucleic acid molecule comprising self-complementary sense and anti-sense strands, wherein the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. The siNA can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region comprises a nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to a nucleotide sequence in a target nucleic acid molecule or a portion thereof and the sense region comprises a nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single-stranded polynucleotide having a nucleotide sequence complementary to nucleotide sequence in a target nucleic acid molecule or a portion thereof (for example, where such siNA molecule does not require the presence within the siNA molecule of a nucleotide sequence corresponding to the target nucleic acid sequence or a portion thereof), wherein the single-stranded polynucleotide can further comprise a terminal phosphate group, such as a 5'-phosphate (see for example Martinez et al., 2002, *Cell.,* 110, 563-574 and Schwarz et al., 2002, *Molecular Cell,* 10, 537-568), or 5',3'-diphosphate.

The term "subject" refers to an organism to which the nucleic acid molecules of the invention can be administered. A subject can be a mammal or mammalian cells, including a human or human cells. The term also refers to an organism, which is a donor or recipient of explanted cells or the cells themselves.

The phrase "systemic administration" refers to in vivo systemic absorption or accumulation of drugs in the blood stream followed by distribution throughout the entire body.

The term "target" as it refers to FCεR1α refers to any FCεR1α target protein, peptide, or polypeptide, such as encoded by Genbank Accession Nos. shown in Table 7. The term also refers to nucleic acid sequences or target polynucleotide sequence encoding any target protein, peptide, or polypeptide, such as proteins, peptides, or polypeptides encoded by sequences having Genbank Accession Nos. shown in Table 7. The target of interest can include target polynucleotide sequences, such as target DNA or target RNA. The term "target" is also meant to include other sequences, such as differing isoforms, mutant target genes, splice variants of target polynucleotides, target polymorphisms, and non-coding (e.g., ncRNA, miRNA, stRNA, sRNA) or other regulatory polynucleotide sequences as described herein.

The phrase "target site" refers to a sequence within a target RNA that is "targeted" for cleavage mediated by an siNA construct, which contains sequences within its antisense region that are complementary to the target sequence.

The phrase "therapeutically effective amount" refers to the amount of the compound or pharmaceutical composition that will elicit the biological or medical response of a cell, tissue, system, animal or human that is be sought by the researcher, veterinarian, medical doctor or other clinician.

The phrase "universal base" refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

The phrase "unmodified nucleoside" refers to one of the bases, adenine, cytosine, guanine, thymine, or uracil, joined to the 1' carbon of β-D-ribo-furanose.

The term "up-regulate" refers to an increase in the expression of a gene, or level of RNA molecules or equivalent RNA molecules encoding one or more proteins or protein subunits, or activity of one or more proteins or protein subunits, above that observed in the absence of the nucleic acid molecules (e.g., siNA) of the invention. In certain instances, up-regulation or promotion of gene expression with an siNA molecule is above that level observed in the presence of an inactive or attenuated molecule. In other instances, up-regulation or promotion of gene expression with siNA molecules is above that level observed in the presence of, for example, an siNA molecule with scrambled sequence or with mismatches. In still other instances, up-regulation or promotion of gene expression with a nucleic acid molecule of the instant invention is greater in the presence of the nucleic acid molecule than in its absence. In some instances, up-regulation or promotion of gene expression is associated with inhibition of RNA mediated gene silencing, such as RNAi mediated cleavage or silencing of a coding or non-coding RNA target that down regulates, inhibits, or silences the expression of the gene of interest to be up-regulated. The down regulation of gene expression can, for example, be induced by a coding RNA or its encoded protein, such as through negative feedback or antagonistic effects. The down regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down regulation of targets that down regulate, suppress, or silence a gene of interest can be used to up-regulate expression of the gene of interest toward therapeutic use.

The term "vectors" refers to any nucleic acid- and/or viral-based technique used to deliver a desired nucleic acid.

B. siNAs Molecules of the Invention

The present invention provides compositions and methods comprising siNAs targeted to FCεR1α that can be used to treat diseases, e.g., respiratory or inflammatory, associated with FCεR1α. In particular aspects and embodiments of the invention, the nucleic acid molecules of the invention comprise sequences shown in Table 1a-1b and/or FIGS. 2-3. The siNAs can be provided in several forms. For example, the siNA can be isolated as one or more siNA compounds, or it may be in the form of a transcriptional cassette in a DNA plasmid. The siNA may also be chemically synthesized and can include modifications. The siNAs can be administered alone or co-administered with other siNA molecules or with conventional agents that treat a FCεR1α related disease or condition.

The siNA molecules of the invention can be used to mediate gene silencing, specifically FCεR1α, via interaction with RNA transcripts or alternately by interaction with particular gene sequences, wherein such interaction results in gene silencing either at the transcriptional level or post-transcriptional level such as, for example, but not limited to, RNAi or through cellular processes that modulate the chromatin structure or methylation patterns of the target and prevent transcription of the target gene, with the nucleotide sequence of the target thereby mediating silencing. More specifically, the target is any of FCεR1α RNA, DNA, mRNA, miRNA, siRNA, or a portion thereof.

In one aspect, the present invention provides a double-stranded short interfering nucleic acid (siNA) molecule comprising a first strand and a second strand having complementarity to each other, wherein at least one strand comprises at least 15 nucleotides of:

| | |
|---|---|
| 5'-CUUGCAAUAUACAUAGAAA-3'; | (SEQ ID NO: 2) |
| 5'-UUUCUAUGUAUAUUGCAAG-3'; | (SEQ ID NO: 131) |
| 5'-CCAUGGAAUAGAAUAUUUA-3'; | (SEQ ID NO: 3) |
| 5'-UAAAUAUUCUAUUCCAUGG-3'; | (SEQ ID NO: 132) |
| 5'-CCCUCAACAUUACUGUAAU-3'; | (SEQ ID NO: 5) |
| 5'-AUUACAGUAAUGUUGAGGG-3'; | (SEQ ID NO: 133) |
| 5'-UCAGCACCAACAAGUUAAU-3'; | (SEQ ID NO: 8) |
| 5'-AUUAACUUGUUGGUGCUGA-3'; | (SEQ ID NO: 134) |
| 5'-ACAGGAUUAUUUAUCUCAA-3'; | (SEQ ID NO: 9) |
| 5'-UUGAGAUAAAUAAUCCUGU-3' | (SEQ ID NO: 135) |
| 5'-UGGUGGUGAUUCUGUUUGC-3'; or | (SEQ ID NO: 17) |
| 5'-GCAAACAGAAUCACCACCA-3'; | (SEQ ID NO: 136) | and
wherein one or more of the nucleotides are optionally chemically modified.

In certain embodiments the 15 nucleotides form a contiguous stretch of nucleotides.

In other embodiments, the siNA molecule can contain one or more nucleotide deletions, substitutions, mismatches and/or additions to SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; provided, however, that the siNA molecule maintains its activity, for example, to mediate RNAi. In a non-limiting example, the deletion, substitution, mismatch and/or addition can result in a loop or buldge, or alternately a wobble or other alternative (non Watson-Crick) base pair.

These siNA molecules can comprise short double-stranded regions of RNA. The double stranded RNA molecules of the invention can comprise two distinct and separate strands that can be symmetric or asymmetric and are complementary, i.e., two single-stranded RNA molecules, or can comprise one single-stranded molecule in which two complementary portions, e.g., a sense region and an antisense region, are base-paired, and are covalently linked by one or more single-stranded "hairpin" areas (i.e. loops) resulting in, for example, a single-stranded short-hairpin polynucleotide or a circular single-stranded polynucleotide.

The linker can be polynucleotide linker or a non-nucleotide linker. In some embodiments, the linker is a non-nucleotide linker. In some embodiments, a hairpin or circular siNA molecule of the invention contains one or more loop motifs, wherein at least one of the loop portion of the siNA molecule is biodegradable. For example, a single-stranded hairpin siNA molecule of the invention is designed such that degradation of the loop portion of the siNA molecule in vivo can generate a double-stranded siNA molecule with 3'-terminal overhangs, such as 3'-terminal nucleotide overhangs comprising 1, 2, 3 or 4 nucleotides. Or alternatively, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In symmetric siNA molecules of the invention, each strand, the sense (passenger) strand and antisense (guide) strand, are independently about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in length In asymmetric siNA molecules, the antisense region or strand of the molecule is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length.

In yet other embodiments, siNA molecules of the invention comprise single stranded hairpin siNA molecules, wherein the siNA molecules are about 25 to about 70 (e.g., about 25, 26, 27, 28, 29, 30, 31, 32, 33, 34, 35, 36, 40, 45, 50, 55, 60, 65, or 70) nucleotides in length.

In still other embodiments, siNA molecules of the invention comprise single-stranded circular siNA molecules, wherein the siNA molecules are about 38 to about 70 (e.g., about 38, 40, 45, 50, 55, 60, 65, or 70) nucleotides in length.

In various symmetric embodiments, the siNA duplexes of the invention independently comprise about 15 to about 40 base pairs (e.g., about 15, 16, 17, 18, 19, 20, 21, 22, 23, 24, 25, 26, 27, 28, 29, 30, 31, 32, 33, 34, 35, 36, 37, 38, 39, or 40).

In yet other embodiments, where the siNA molecules of the invention are asymmetric, the siNA molecules comprise about 3 to 25 (e.g., about 3, 4, 5, 6, 7, 8, 9, 10, 11, 12, 13, 14, 15, 16, 17, 18, 19, 20, 21, 22, 23, 24, or 25) base pairs).

In still other embodiments, where the siNA molecules of the invention are hairpin or circular structures, the siNA molecules comprise about 3 to about 30 (e.g., about 15, 16, 17, 18, 19, 20, 21, 22, 23, 24, 25, 26, 27, 28, 29, or 30) base pairs.

The sense strand and antisense strands or sense region and antisense regions of the siNA molecules of the invention can be complementary. Also, the antisense strand or antisense region can be complementary to a nucleotide sequence or a portion thereof of the FCϵR1α target RNA. The sense strand or sense region if the siNA can comprise a nucleotide sequence of a FCϵR1α gene or a portion thereof. In certain embodiments, the sense region or sense strand of an siNA molecule of the invention is complementary to that portion of the antisense region or antisense strand of the siNA molecule that is complementary to a FCϵR1α target polynucleotide sequence, such as for example, but not limited to, those sequences represented by GENBANK Accession Nos. shown in Table. 7.

In some embodiments, siNA molecules of the invention have perfect complementarity between the sense strand or sense region and the antisense strand or antisense region of the siNA molecule. In other or the same embodiments, siNA molecules of the invention are perfectly complementary to a corresponding target nucleic acid molecule.

In yet other embodiments, siNA molecules of the invention have partial complementarity (i.e., less than 100% complementarity) between the sense strand or sense region and the antisense strand or antisense region of the siNA molecule or between the antisense strand or antisense region of the siNA molecule and a corresponding target nucleic acid molecule. Thus, in some embodiments, the double-stranded nucleic acid molecules of the invention, have between about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in one strand that are complementary to the nucleotides of the other strand. In other embodiments, the molecules have between about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in the sense region that are complementary to the nucleotides of the antisense region. of the double-stranded nucleic acid molecule. In yet other embodiments, the double-stranded nucleic acid molecules of the invention have between about 15 to about 40 (e.g., about 15, 16, 17, 18, 19, 20, 21, 22, 23, 24, 25, 26, 27, 28, 29, 30, 31, 32, 33, 34, 35, 36, 37, 38, 39, or 40) nucleotides in the antisense strand that are complementary to a nucleotide sequence of its corresponding target nucleic acid molecule.

In some embodiments, the double-stranded nucleic acid molecules of the invention, have 1 or more (e.g., 1, 2, 3, 4, 5, or 6) nucleotides, in one strand or region that are mismatches or non-base-paired with the other strand or region. In other embodiments, the double-stranded nucleic acid molecules of the invention, have 1 or more (e.g., 1, 2, 3, 4, 5, or 6) nucleotides in each strand or region that are mismatches or non-base-paired with the other strand or region.

The invention also comprises double-stranded nucleic acid (siNA) molecules as otherwise described hereinabove in which the first strand and second strand are complementary to each other and wherein at least one strand is hybridisable to the polynucleotide sequence of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; under conditions of high stringency, and wherein any of the nucleotides is unmodified or chemically modified.

Hybridization techniques are well known to the skilled artisan (see for instance, Sambrook et al., Molecular Cloning: A Laboratory Manual, 2nd Ed., Cold Spring Harbor Laboratory Press, Cold Spring Harbor, N.Y. (1989)). Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C.

In one specific embodiment, the first strand has about 15, 16, 17, 18, 19, 20 or 21 nucleotides that are complementary to the nucleotides of the other strand and at least one strand is hybridisable to the polynucleotide sequence of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; under conditions of high stringency, and wherein any of the nucleotides is unmodified or chemically modified.

In certain embodiments, the siNA molecules of the invention comprise overhangs of about 1 to about 4 (e.g., about 1, 2, 3 or 4) nucleotides. The nucleotides in the overhangs can be the same or different nucleotides. In some embodiments, the overhangs occur at the 3'-end at one or both strands of the double-stranded nucleic acid molecule. For example, a double-stranded nucleic acid molecule of the invention can comprise a nucleotide or non-nucleotide overhang at the 3'-end of the guide strand or antisense strand/region, the 3'-end of the passenger strand or sense strand/region, or both the guide strand or antisense strand/region and the passenger strand or sense strand/region of the double-stranded nucleic acid molecule.

In some embodiments, the nucleotides comprising the overhang portion of an siNA molecule of the invention comprise sequences based on the FCεR1α target polynucleotide sequence in which nucleotides comprising the overhang portion of the guide strand or antisense strand/region of an siNA molecule of the invention can be complementary to nucleotides in the FCεR1α target polynucleotide sequence and/or nucleotides comprising the overhang portion of the passenger strand or sense strand/region of an siNA molecule of the invention can comprise the nucleotides in the FCεR1α target polynucleotide sequence. Thus, in some embodiments, the overhang comprises a two nucleotide overhang that is complementary to a portion of the FCεR1α target polynucleotide sequence. In other embodiments, however, the overhang comprises a two nucleotide overhang that is not complementary to a portion of the FCεR1α target polynucleotide sequence. In certain embodiments, the overhang comprises a 3'-UU overhang that is not complementary to a portion of the FCεR1α target polynucleotide sequence. In other embodiments, the overhang comprises a UU overhang at the 3' end of the antisense strand and a TT overhang at the 3' end of the sense strand.

In any of the embodiments of the siNA molecules described herein having 3'-terminal nucleotide overhangs, the overhangs are optionally chemically modified at one or more nucleic acid sugar, base, or backbone positions. Representative, but not limiting examples of modified nucleotides in the overhang portion of a double-stranded nucleic acid (siNA) molecule of the invention include 2'-O-alkyl (e.g., 2'-O-methyl), 2'-deoxy, 2'-deoxy-2'-fluoro, 2'-deoxy-2'-fluoroarabino (FANA), 4'-thio, 2'-O-trifluoromethyl, 2'-O-ethyl-trifluoromethoxy, 2'-O-difluoromethoxy-ethoxy, universal base, acyclic, or 5-C-methyl nucleotides. In more preferred embodiments, the overhang nucleotides are each independently, a 2'-O-alkyl nucleotide, 2'-O-methyl nucleotide, 2'-deoxy-2-fluoro nucleotide, or 2'-deoxyribonucleotide In yet other embodiments, siNA molecules of the invention comprise duplex nucleic acid molecules with blunt ends (i.e., does not have any nucleotide overhangs), where both ends are blunt, or alternatively, where one of the ends is blunt. In some embodiments, the siNA molecules of the invention can comprises one blunt end, for example wherein the 5'-end of the antisense strand and the 3'-end of the sense strand do not have any overhanging nucleotides. In another example, the siNA molecule comprises one blunt end, for example wherein the 3'-end of the antisense strand and the 5'-end of the sense strand do not have any overhanging nucleotides. In other embodiments, siNA molecules of the invention comprise two blunt ends, for example wherein the 3'-end of the antisense strand and the 5'-end of the sense strand as well as the 5'-end of the antisense strand and 3'-end of the sense strand do not have any overhanging nucleotides.

In any of the embodiments or aspects of the siNA molecules of the invention, the sense strand and/or the antisense strand can further have a cap, such as described herein or as known in the art, at the 3'-end, the 5'-end, or both of the 3' and 5'-ends of the sense strand and/or antisense strand. Or as in the case of a hairpin siNA molecule, the cap can be at either one or both of the terminal nucleotides of the polynucleotide. In some embodiments, the cap is at one of both of the ends of the sense strand of a double-stranded siNA molecule. In other embodiments, the cap is at the at the 5'-end and 3'-end of antisense (guide) strand. In preferred embodiments, the caps are at the 3'-end of the sense strand and the 5' end of the sense strand.

Representative, but non-limiting examples of such terminal caps include an inverted abasic nucleotide, an inverted deoxy abasic nucleotide, an inverted nucleotide moiety, a group shown in FIG. 5, a glyceryl modification, an alkyl or cycloalkyl group, a heterocycle, or any other group that prevents RNAi activity.

Any of the embodiments of the siNA molecules of the invention can have a 5' phosphate termini. In some embodiments, the siNA molecules lack terminal phosphates.

Any siNA molecule or construct of the invention can comprise one or more chemical modifications. Modifications can be used to improve in vitro or in vivo characteristics such as stability, activity, toxicity, immune response (e.g., prevent stimulation of an interferon response, an inflammatory or pro-inflammatory cytokine response, or a Toll-like Receptor (TlF) response), and/or bioavailability.

Applicant describes herein chemically modified siNA molecules with improved RNAi activity compared to corresponding unmodified or minimally modified siRNA molecules. The chemically modified siNA motifs disclosed herein provide the capacity to maintain RNAi activity that is substantially similar to unmodified or minimally modified active siRNA (see for example Elbashir et al., 2001, EMBO J., 20:6877-6888) while at the same time providing nuclease resistance and pharmacokinetic properties suitable for use in therapeutic applications.

In various embodiments, the siNA molecules of the invention comprise modifications wherein any (e.g., one or more or all) nucleotides present in the sense and/or antisense strand are modified nucleotides (e.g., wherein one nucleotide is modified or all nucleotides are modified nucleotides or alternately a plurality (i.e. more than one) of the nucleotides are modified nucleotides. In some embodiments, the siNA molecules of the invention are partially modified (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80 nucleotides are modified) with chemical modifications. In other embodiments, the siNA molecules of the invention are completely modified (e.g., 100% modified) with chemical modifications, i.e., the siNA molecule does not contain any ribonucleotides. In other embodiments, an siNA molecule of the invention comprises at least about 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78 nucleotides that are modified nucleotides. In some of embodiments, 1 or more of the nucleotides in the sense strand of the siNA molecules of the invention are modified. In the same or other embodiments, 1 or more of the nucleotides in the antisense strand of the siNA molecules of the invention are modified.

The chemical modification within a single siNA molecule can be the same or different. In some embodiments, at least one strand has at least one chemical modification. In other embodiments, each strand has at least one chemical modifications, which can be the same or different, such as, sugar, base, or backbone (i.e., internucleotide linkage) modifications. In other embodiments, siNA molecules of the invention contains at least 2, 3, 4, 5, or more different chemical modifications.

Non-limiting examples of chemical modifications that are suitable for use in the present invention, are disclosed in U.S. Ser. No. 10/444,853, U.S. Ser. No. 10/981,966, U.S. Ser. No. 12/064,014 and in references cited therein and include sugar, base, and phosphate, non-nucleotide modifications, and/or any combination thereof.

In various embodiments, a majority of the pyrimidine nucleotides present in the double-stranded siNA molecule comprises a sugar modification. In yet other embodiments, a majority of the purine nucleotides present in the double-stranded siNA molecule comprises a sugar modification. In certain instances, the purines and pyrimidines are differentially modified at the 2'-sugar position (i.e., at least one purine has a different modification from at least one pyrimidine in the same or different strand at the 2'-sugar position).

In certain specific embodiments of this aspect of the invention, at least one modified nucleotide is a 2'-deoxy-2-fluoro nucleotide, a 2'-deoxy nucleotide, or a 2'-O-alkyl (e.g., 2'-O-methyl) nucleotide.

In yet other embodiments of the invention, at least one nucleotide has a ribo-like, Northern or A form helix configuration (see e.g., Saenger, Principles of Nucleic Acid Structure, Springer-Verlag ed., 1984). Non-limiting examples of nucleotides having a Northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl nucleotides, 2'-deoxy-2'-fluoro nucleotides, 2'-deoxy-2'-chloro nucleotides, 2'-azido nucleotides, 2'-O-trifluoromethyl nucleotides, 2'-O-ethyl-trifluoromethoxy nucleotides, 2'-O-difluoromethoxy-ethoxy nucleotides, 4'-thio nucleotides and 2'-O-methyl nucleotides.

In certain embodiments of the invention, all the pyrimidine nucleotides in the complementary region on the sense strand are 2'-deoxy-2'-fluoro pyrimidine nucleotides. In certain embodiments, all of the pyrimidine nucleotides in the complementary region of the antisense strand are 2'-deoxy-2'-fluoro pyrimidine nucleotides. In certain embodiments, all the purine nucleotides in the complementary region on the sense strand are 2'-deoxy purine nucleotides. In certain embodiments, all of the purines in the complementary region on the antisense strand are 2'-O-methyl purine nucleotides. In certain embodiments, all of the pyrimidine nucleotides in the complementary regions on the sense strand are 2'-deoxy-2'-fluoro pyrimidine nucleotides; all of the pyrimidine nucleotides in the complementary region of the antisense strand are 2'-deoxy-2'-fluoro pyrimidine nucleotides; all the purine nucleotides in the complementary region on the sense strand are 2'-deoxy purine nucleotides and all of the purines in the complementary region on the antisense strand are 2'-O-methyl purine nucleotides.

Any of the above described modifications, or combinations thereof, including those in the references cited, can be applied to any of the siNA molecules of the invention.

The modified siNA molecules of the invention can comprise modifications at various locations within the siNA molecule. In some embodiments, the double-stranded siNA molecule of the invention comprises modified nucleotides at internal base paired positions within the siNA duplex. In other embodiments, a double-stranded siNA molecule of the invention comprises modified nucleotides at non-base paired or overhang regions of the siNA molecule. In yet other embodiments, a double-stranded siNA molecule of the invention comprises modified nucleotides at terminal positions of the siNA molecule. For example, such terminal regions include the 3'-position and/or 5'-position of the sense and/or antisense strand or region of the siNA molecule. Additionally, any of the modified siNA molecules of the invention can have a modification in one or both oligonucleotide strands of the siNA duplex, for example in the sense strand, the antisense strand, or both strands. Moreover, with regard to chemical modifications of the siNA molecules of the invention, each strand of the double-stranded siNA molecules of the invention can have one or more chemical modifications, such that each strand comprises a different pattern of chemical modifications.

In certain embodiments each strand of a double-stranded siNA molecule of the invention comprises a different pattern of chemical modifications, such as any "Stab 00"-"Stab 36" or "Stab 3F"-"Stab 36F" (Table 8) modification patterns herein or any combination thereof. Further, non-limiting examples of modification schemes that could give rise to different patterns of modifications are shown in Table 8. The stabilization chemistries referred to in Table 8 as Stab, can be combined in any combination of Sense/Antisense chemistries, such as Stab 7/8, Stab 7/11, Stab 8/8, Stab 18/8, Stab 18/11, Stab 12/13, Stab 7/13, Stab 18/13, Stab 7/19, Stab 8/19, Stab 18/19, Stab 7/20, Stab 8/20, Stab 18/20, Stab 7/32, Stab 8/32, or Stab 18/32 (e.g., any siNA having Stab 7, 8, 11, 12, 13, 14, 15, 17, 18, 19, 20, or 32 sense or antisense strands or any combination thereof). Herein, numeric Stab chemistries can include both 2'-fluoro and 2'-OCF3 versions of the chemistries shown in Table 8. For example, "Stab ⅞" refers to both Stab 7/8 and Stab 7F/8F etc.

In other embodiments, one or more (for example 1, 2, 3, 4 or 5) nucleotides at the 5'-end of the guide strand or guide region (also known as antisense strand or antisense region) of the siNA molecule are ribonucleotides.

In some embodiments, the pyrimidine nucleotides in the antisense strand are 2'-O-methyl or 2'-deoxy-2'-fluoro pyrimidine nucleotides and the purine nucleotides present in the antisense strand are 2'-O-methyl nucleotides or 2'-deoxy nucleotides. In other embodiments, the pyrimidine nucleotides in the sense strand are 2'-deoxy-2'-fluoro pyrimidine nucleotides and the purine nucleotides present in the sense strand are 2'-O-methyl or 2'-deoxy purine nucleotides.

Figure 1:
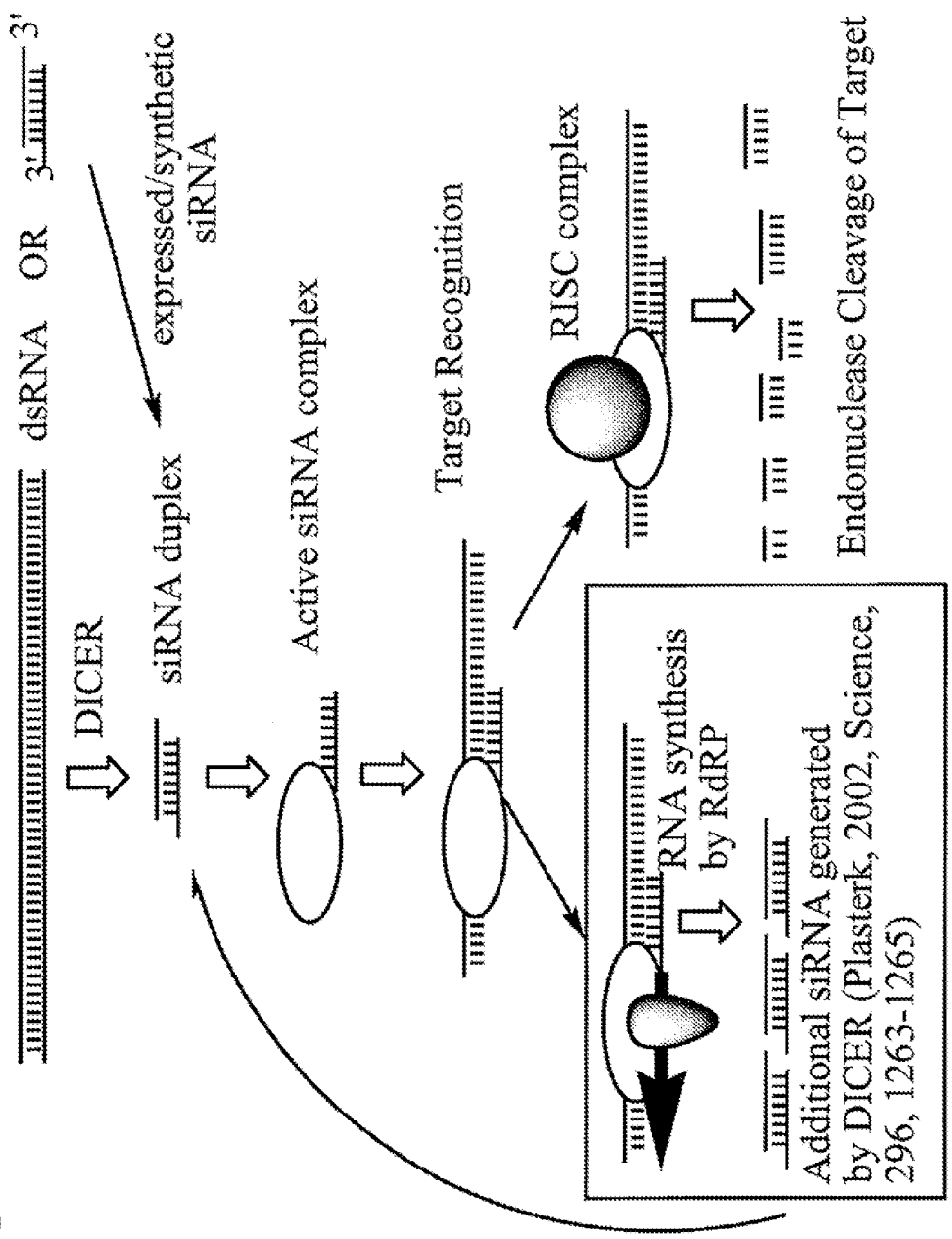
FIG. 1 shows a non-limiting proposed mechanistic representation of target RNA degradation involved in RNAi. Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex forms which recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.
Figure 2:
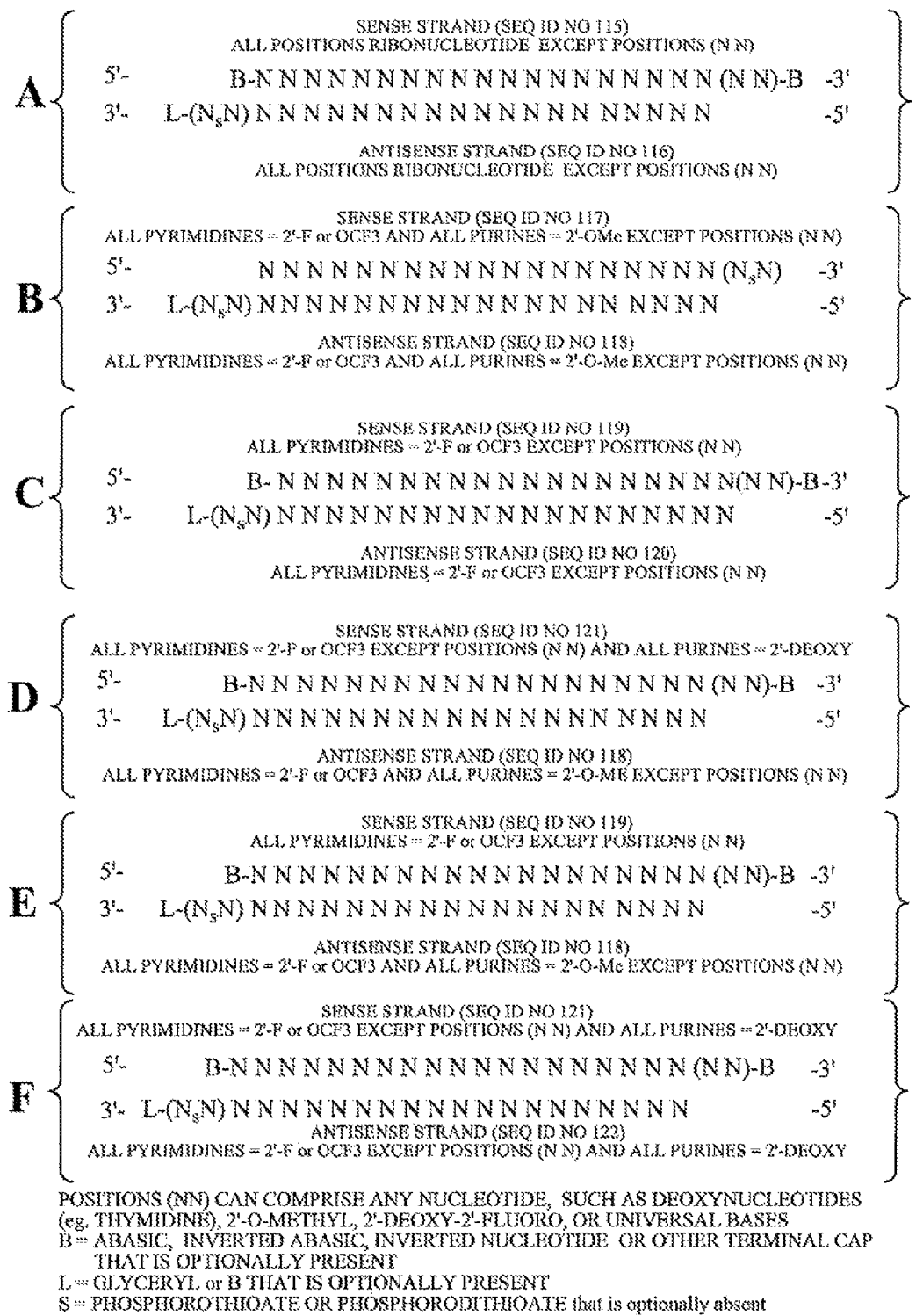
FIG. 2A-F shows non-limiting examples of chemically modified siNA constructs of the present invention. In the figure, N stands for any nucleotide (adenosine, guanosine, cytosine, uridine, or optionally thymidine, for example thymidine can be substituted in the overhanging regions designated by parenthesis (N N). Various modifications are shown for the sense and antisense strands of the siNA constructs. The (N N) nucleotide positions can be chemically modified as described herein (e.g., 2'-O-methyl, 2'-deoxy-2'-fluoro etc.) and can be either derived from a corresponding target nucleic acid sequence or not (see for example FIG. 4C). Furthermore, although not depicted on the Figure, the sequences shown in FIG. 2 can optionally include a ribonucleotide at the 9$^{th}$ position from the 5'-end of the sense strand or the 11$^{th}$ position based on the 5'-end of the guide strand by counting 11 nucleotide positions in from the 5'-terminus of the guide strand (see FIG. 4C). The antisense strand of constructs A-F comprises sequence complementary to any target nucleic acid sequence of the invention. Furthermore, when a glyceryl moiety (L) is present at the 3'-end of the antisense strand for any construct shown in FIG. 2 A-F, the modified internucleotide linkage is optional.
Figure 3:
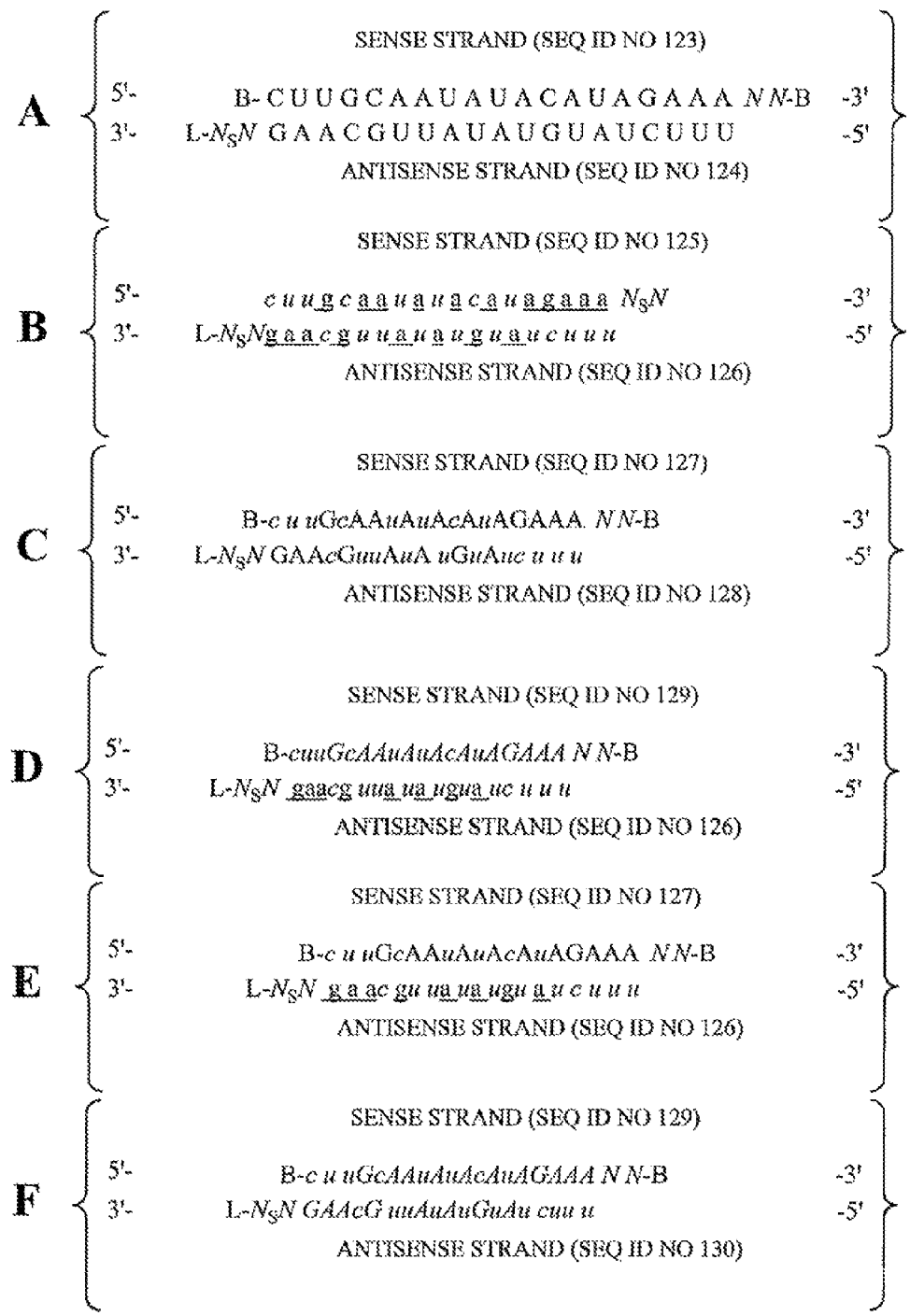
FIG. 3A-F shows non-limiting examples of specific chemically modified siNA sequences of the invention. A-F applies the chemical modifications described in FIG. 2A-F to an exemplary FCεR1α siNA sequence. Such chemical modifications can be applied to any FCεR1α sequence. Furthermore, although this is not depicted on FIG. 3, the sequences shown in FIG. 3 can optionally include a ribonucleotide at the $9^{th}$ position from the 5'-end of the sense strand or the $11^{th}$ position based on the 5'-end of the guide strand by counting 11 nucleotide positions in from the 5'-terminus of the guide strand (see FIG. 4C). In addition, the sequences shown in FIG. 3 can optionally include terminal ribonucleotides at up to about 6 positions at the 5'-end of the antisense strand (e.g., about 1, 2, 3, 4, 5, or 6 terminal ribonucleotides at the 5'-end of the antisense strand).

Further non-limiting examples of sense and antisense strands of such siNA molecules having various modification patterns are shown in FIGS. 2 and 3.

In certain embodiments of the invention, double-stranded siNA molecules are provided, wherein the molecule has a sense strand and an antisense strand and comprises the following formula (A):

wherein, the upper strand is the sense strand and the lower strand is the antisense strand of the double-stranded nucleic acid molecule; wherein the antisense strand comprises at least 15 nucleotides of SEQ ID NO: 131, SEQ ID NO: 132, SEQ ID NO: 133, SEQ ID NO: 134, SEQ ID NO: 135, or SEQ ID NO: 136, and the sense strand comprises a sequence having complementarity to the antisense strand;

each N is independently a nucleotide which is unmodified or chemically modified;

each B is a terminal cap that is present or absent;

(N) represents overhanging nucleotides, each of which is independently unmodified chemically modified;

[N] represents nucleotides that are ribonucleotides;

X1 and X2 are independently integers from 0 to 4;

X3 is an integer from 17 to 36;

X4 is an integer from 11 to 35; and

X5 is an integer from 1 to 6, provided that the sum of X4 and X5 is 17-36.

In certain embodiments, the at least 15 nucleotides form a contiguous stretch of nucleotides.

In other embodiments, the siNA molecule can contain one or more nucleotide deletions, substitutions, mismatches and/or additions to SEQ ID NO: 131, SEQ ID NO: 132, SEQ ID NO: 133, SEQ ID NO: 134, SEQ ID NO: 135, or SEQ ID NO: 136 provided however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair.

In one embodiment, the invention features a double-stranded short interfering nucleic acid (siNA) of formula (A); wherein
(a) one or more pyrimidine nucleotides in $N_{X4}$ positions are independently 2'-deoxy-2'-fluoro nucleotides, 2'-O-alkyl nucleotides, 2'-deoxy nucleotides, ribonucleotides, or any combination thereof;
(b) one or more purine nucleotides in $N_{X4}$ positions are independently 2'-deoxy-2'-fluoro nucleotides, 2'-O-alkyl nucleotides, 2'-deoxy nucleotides, ribonucleotides, or any combination thereof;
(c) one or more pyrimidine nucleotides in $N_{X3}$ positions are independently 2'-deoxy-2'-fluoro nucleotides, 2'-O-alkyl nucleotides, 2'-deoxy nucleotides, ribonucleotides, or any combination thereof; and
(d) one or more purine nucleotides in $N_{X3}$ positions are independently 2'-deoxy-2'-fluoro nucleotides, 2'-O-alkyl nucleotides, 2'-deoxy nucleotides, ribonucleotides, or any combination thereof.

In one embodiment, the invention features a double-stranded short interfering nucleic acid (siNA) of formula (A); wherein
(a) each pyrimidine nucleotide in $N_{X4}$ positions is independently a 2'-deoxy-2'-fluoro nucleotide, 2'-O-alkyl nucleotide, 2'-deoxy nucleotide, or ribonucleotide;
(b) each purine nucleotide in $N_{X4}$ positions is independently a 2'-deoxy-2'-fluoro nucleotide, 2'-O-alkyl nucleotide, 2'-deoxy nucleotide, or ribonucleotide;
(c) each pyrimidine nucleotide in $N_{X3}$ positions is independently a 2'-deoxy-2'-fluoro nucleotide, 2'-O-alkyl nucleotide, 2'-deoxy nucleotide, or ribonucleotide; and
(d) each purine nucleotides in $N_{X3}$ positions is independently a 2'-deoxy-2'-fluoro nucleotide, 2'-O-alkyl nucleotide, 2'-deoxy nucleotide, or ribonucleotide.

In one embodiment, the invention features a double-stranded short interfering nucleic acid (siNA) of formula (A); wherein
(a) each pyrimidine nucleotide in $N_{X4}$ positions is independently a 2'-deoxy-2'-fluoro nucleotide;
(b) each purine nucleotide in $N_{X4}$ positions is independently a 2'-O-alkyl nucleotide;
(c) each pyrimidine nucleotide in $N_{X3}$ positions is independently a 2'-deoxy-2'-fluoro nucleotide; and
(d) each purine nucleotide in $N_{X3}$ positions is independently a 2'-deoxy nucleotide.

In one embodiment, the invention features a double-stranded short interfering nucleic acid (siNA) of formula (A); wherein
(a) each pyrimidine nucleotide in $N_{X4}$ positions is independently a 2'-deoxy-2'-fluoro nucleotide;
(b) each purine nucleotide in $N_{X4}$ positions is independently a 2'-O-alkyl nucleotide;
(c) each pyrimidine nucleotide in $N_{X3}$ positions is independently a 2'-deoxy-2'-fluoro nucleotide; and
(d) each purine nucleotide in $N_{X3}$ positions is independently a ribonucleotide.

In one embodiment, the invention features a double-stranded short interfering nucleic acid (siNA) of formula (A); wherein
(a) each pyrimidine nucleotide in $N_{X4}$ positions is independently a 2'-deoxy-2'-fluoro nucleotide;
(b) each purine nucleotide in $N_{X4}$ positions is independently a ribonucleotide;
(c) each pyrimidine nucleotide in $N_{X3}$ positions is independently a 2'-deoxy-2'-fluoro nucleotide; and
(d) each purine nucleotide in $N_{X3}$ positions is independently a ribonucleotide.

In some embodiments, siNA molecules having formula A comprise a terminal phosphate group at the 5'-end of the antisense strand or antisense region of the nucleic acid molecule.

In various embodiments, siNA molecules having formula A comprise X5=1, 2, or 3; each X1 and X2=1 or 2; X3=17, 18, 19, 20, 21, 22, 23, 24, 25, 26, 27, 28, 29, or 30, and X4=15, 16, 17, 18, 19, 20, 21, 22, 23, 24, 25, 26, 27, 28, 29, or 30.

In one specific embodiment, an siNA molecule having formula A comprises X5=1; each X1 and X2=2; X3=19, and X4=18.

In another specific embodiment, an siNA molecule having formula A comprises X5=2; each X1 and X2=2; X3=19, and X4=17

In yet another embodiment, an siNA molecule having formula A comprises X5=3; each X1 and X2=2; X3=19, and X4=16.

In certain embodiments, siNA molecules having formula A comprise caps (B) at the 3' and 5' ends of the sense strand or sense region.

In certain embodiments, siNA molecules having formula A comprise caps (B) at the 3'-end of the antisense strand or antisense region.

In various embodiments, siNA molecules having formula A comprise caps (B) at the 3' and 5' ends of the sense strand or sense region and caps (B) at the 3'-end of the antisense strand or antisense region.

In yet other embodiments, siNA molecules having formula A comprise caps (B) only at the 5'-end of the sense (upper) strand of the double-stranded nucleic acid molecule.

In some embodiments, siNA molecules having formula A further comprise one or more phosphorothioate internucleotide linkages between the first terminal (N) and the adjacent nucleotide on the 3' end of the sense strand, antisense strand, or both sense strand and antisense strands of the nucleic acid molecule. For example, a double-stranded nucleic acid molecule can comprise X1 and/or X2=2 having overhanging nucleotide positions with a phosphorothioate internucleotide linkage, e.g., (NsN) where "s" indicates phosphorothioate.

In some embodiments, siNA molecules having formula A comprises (N) nucleotides in the antisense strand (lower strand) that are complementary to nucleotides in a FCεR1α target polynucleotide sequence which also has complementarity to the N and [N] nucleotides of the antisense (lower) strand.

In yet another embodiment, the invention provides a double stranded short interfering nucleic acid (siNA) molecule wherein the siNA is:

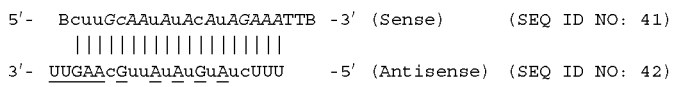

wherein:
    each B is an inverted abasic cap moiety;
    c is 2'-deoxy-2'fluorocytidine;
    u is 2'-deoxy-2'fluorouridine;
    A is 2'-deoxyadenosine;
    G is 2'-deoxyguanosine;
    T is thymidine;
    U is uridine;
    A is 2'-O-methyl-adenosine;
    G̅ is 2'-O-methyl-guanosine;
    U̅ is 2'-O-methyl-uridine; and
    the internucleotide linkages are chemically modified or unmodified.

In yet another embodiment, the invention provides a double stranded short interfering nucleic acid (siNA) molecule wherein the siNA is:

```
5'- BccAuGGAAuAGAAuAuuuATTB -3'  (Sense)      (SEQ ID NO: 43)
    ||||||||||||||||||||
 3' UUGGuAccuuAucuuAuAAAU    -5'  (Antisense)  (SEQ ID NO: 44)
``` wherein:
    each B is an inverted abasic cap;
    c is 2'-deoxy-2'fluorocytidine;
    u is 2'-deoxy-2'fluorouridine;
    A is 2'-deoxyadenosine;
    G is 2'-deoxyguanosine;
    T is thymidine;
    A is adenosine;
    U is uridine;
    A is 2'-O-methyl-adenosine;
    G̅ is 2'-O-methyl-guanosine;
    U̅ is 2'-O-methyl-uridine; and
    the internucleotide linkages are chemically modified or unmodified.

In yet another embodiment, the invention provides a double stranded short interfering nucleic acid (siNA) molecule wherein the siNA is:

```
5'- BccucAAcAuuAcuGuAAuTTB  3'  (Sense)      (SEQ ID NO: 47)
    ||||||||||||||||||||
 3' UUGGGAGuuGuAAuGAcAUUA   5'  (Antisense)  (SEQ ID NO: 48)
``` wherein:
    each B is an inverted abasic cap moiety;
    c is 2'-deoxy-2'fluorocytidine;
    u is 2'-deoxy-2'fluorouridine;
    A is 2'-deoxyadenosine;
    G is 2'-deoxyguanosine;
    T is thymidine;
    A is adenosine;
    U is uridine;
    A is 2'-O-methyl-adenosine;
    G̅ is 2'-O-methyl-guanosine;
    U̅ is 2'-O-methyl-uridine; and
    the internucleotide linkages are chemically modified or unmodified.

In yet another embodiment, the invention provides a double stranded short interfering nucleic acid (siNA) molecule wherein the siNA is:

```
5'- BucAGcAccAAcAAGuuAAuTTB -3'  (Sense)      (SEQ ID NO: 53)
    ||||||||||||||||||||
 3' UUAGucGuGGuuGuucAAUUA   -5'  (Antisense)  (SEQ ID NO: 54)
``` wherein:
    each B is an inverted abasic cap moiety;
    c is 2'-deoxy-2'fluorocytidine;
    u is 2'-deoxy-2'fluorouridine;
    A is 2'-deoxyadenosine;
    G is 2'-deoxyguanosine;
    T is thymidine;
    A is adenosine;
    U is uridine;
    A is 2'-O-methyl-adenosine;
    G̅ is 2'-O-methyl-guanosine;
    U̅ is 2'-O-methyl-uridine; and
    the internucleotide linkages are chemically modified or unmodified.

In yet another embodiment, the invention provides a double stranded short interfering nucleic acid (siNA) molecule wherein the siNA is:

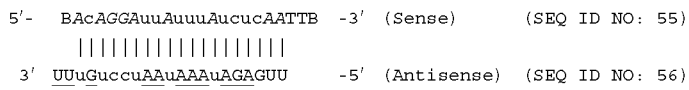

```
5'-  BAcAGGAuuAuuuAucucAATTB  -3'  (Sense)      (SEQ ID NO: 55)
     ||||||||||||||||||||
  3' UUuGuccuAAuAAAuAGAGUU    -5'  (Antisense)  (SEQ ID NO: 56)
``` wherein:
each B is an inverted abasic cap moiety;
c is 2'-deoxy-2'fluorocytidine;
u is 2'-deoxy-2'fluorouridine;
A is 2'-deoxyadenosine;
G is 2'-deoxyguanosine;
T is thymidine;
G is guanosine;
U is uridine;
A is 2'-O-methyl-adenosine;
Ḡ is 2'-O-methyl-guanosine;
Ū is 2'-O-methyl-uridine; and
the internucleotide linkages are chemically modified or unmodified.

In yet another embodiment, the invention provides a double stranded short interfering nucleic acid (siNA) molecule wherein the siNA is:

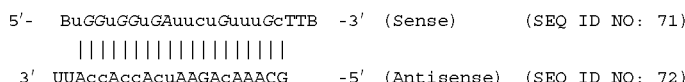

```
5'-  BuGGuGGuGAuucuGuuuGcTTB  -3'  (Sense)      (SEQ ID NO: 71)
     ||||||||||||||||||||
  3' UUAccAccAcuAAGAcAAACG    -5'  (Antisense)  (SEQ ID NO: 72)
``` wherein:
each B is an inverted abasic cap moiety;
c is 2'-deoxy-2'fluorocytidine;
u is 2'-deoxy-2'fluorouridine;
A is 2'-deoxyadenosine;
G is 2'-deoxyguanosine;
T is thymidine;
G is guanosine;
A is adenosine;
C is cytidine;
A is 2'-O-methyl-adenosine;
Ḡ is 2'-O-methyl-guanosine;
Ū is 2'-O-methyl-uridine; and
the internucleotide linkages are chemically modified or unmodified.

C. Generation/Synthesis of siNA Molecules

The siNAs of the invention can be obtained using a number of techniques known to those of skill in the art. For example the siNA can be chemically synthesized or may be encoded by plasmid (e.g., transcribed as sequences that automatically fold into duplexes with hairpin loops). siNA can also be generated by cleavage of longer dsRNA (e.g., dsRNA greater than about 25 nucleotides in length) by the *E. coli* RNase II or Dicer. These enzymes process the dsRNA into biologically active siRNA (see, e.g., Yang et al., PNAS USA 99:9942-9947 (2002); Calegari et al. PNAS USA 99:14236 (2002) Byron et al. Ambion Tech Notes; 10 (1):4-6 (2009); Kawaski et al., Nucleic Acids Res., 31:981-987 (2003), Knight and Bass, Science, 293:2269-2271 (2001) and Roberston et al., J. Biol. Chem 243:82 (1969).

1. Chemical Synthesis

Preferably, siNA of the invention are chemically synthesized. Oligonucleotides (e.g., certain modified oligonucleotides or portions of oligonucleotides lacking ribonucleotides) are synthesized using protocols known in the art, for example as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.*, 74, 59, Brennan et al., 1998, *Biotechnol Bioeng.*, 61, 33-45, and Brennan, U.S. Pat. No. 6,001,311. The synthesis of oligonucleotides makes use of common nucleic acid protecting and coupling groups, such as dimethoxytrityl at the 5'-end, and phosphoramidites at the 3'-end.

siNA molecules without modifications are synthesized using procedures as described in Usman et al., 1987, *J. Am. Chem. Soc.*, 109, 7845; Scaringe et al., 1990, *Nucleic Acids Res.*, 18, 5433. These which makes use of common nucleic acid protecting and coupling groups, such as dimethoxytrityl at the 5'-end, and phosphoramidites at the 3'-end, can be used for certain siNA molecules of the invention.

In certain embodiments, the siNA molecules of the invention are synthesized, deprotected, and analyzed according to methods described in U.S. Pat. Nos. 6,995,259, 6,686,463, 6,673,918, 6,649,751, 6,989,442, and U.S. Ser. No. 10/190,359

In a non-limiting synthesis example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides. Table 9 outlines the amounts and the contact times of the reagents used in the synthesis cycle.

Alternatively, the siNA molecules of the present invention can be synthesized separately and joined together post-synthetically, for example, by ligation (Moore et al., 1992, *Science* 256, 9923; Draper et al., International PCT Publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204), or by hybridization following synthesis and/or deprotection.

Various siNA molecules of the invention can also be synthesized using the teachings of Scaringe et al., U.S. Pat. Nos. 5,889,136; 6,008,400; and 6,111,086.

2. Vector Expression

Alternatively, siNA molecules of the invention that interact with and down-regulate gene encoding target FCεR1α molecules can be expressed and delivered from transcription units (see for example Couture et al., 1996, *TIG.*, 12, 510) inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus.

In some embodiments, pol III based constructs are used to express nucleic acid molecules of the invention transcription of the siNA molecule sequences can be driven from a promoter for eukaryotic RNA polymerase I (pol I), RNA polymerase II (pol II), or RNA polymerase III (pol III). (see for example Thompson, U.S. Pat. Nos. 5,902,880 and 6,146, 886). (See also, Izant and Weintraub, 1985, *Science*, 229, 345; McGarry and Lindquist, 1986, *Proc. Natl. Acad. Sci.*, USA 83, 399; Scanlon et al., 1991, *Proc. Natl. Acad. Sci. USA*, 88, 10591-5; Kashani-Sabet et al., 1992, *Antisense Res. Dev.*, 2, 3-15; Dropulic et al., 1992, *J. Virol.*, 66, 1432-41; Weerasinghe et al., 1991, *J. Virol.*, 65, 5531-4; Ojwang et al., 1992, *Proc. Natl. Acad. Sci. USA*, 89, 10802-6; Chen et al., 1992, *Nucleic Acids Res.*, 20, 4581-9; Sarver et al., 1990 *Science*, 247, 1222-1225; Thompson et al., 1995, *Nucleic Acids Res.*, 23, 2259; Good et al., 1997, *Gene Therapy*, 4, 45. Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. U S A*, 87, 6743-7; Gao and Huang 1993, *Nucleic Acids Res.*, 21, 2867-72; Lieber et al., 1993, *Methods Enzymol.*, 217, 47-66; Zhou et al., 1990, *Mol. Cell. Biol.*, 10, 4529-37). Several investigators have demonstrated that nucleic acid molecules expressed from such promoters can function in mammalian cells (e.g. Kashani-Sabet et al., 1992, *Antisense Res. Dev.*, 2, 3-15; Ojwang et al., 1992, *Proc. Natl. Acad. Sci. U S A*, 89, 10802-6; Chen et al., 1992, *Nucleic Acids Res.*, 20, 4581-9; Yu et al., 1993, *Proc. Natl. Acad. Sci. U S A*, 90, 6340-4; L'Huillier et al., 1992, *EMBO J.*, 11, 4411-8; Lisziewicz et al., 1993, *Proc. Natl. Acad. Sci. U. S. A*, 90, 8000-4; Thompson et al., 1995, *Nucleic Acids Res.*, 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, *Nucleic Acid Res.*, 22, 2830; Noonberg et al., U.S. Pat. No. 5,624,803; Good et al., 1997, *Gene Ther.*, 4, 45; Beigelman et al., International PCT Publication No. WO 96/18736. The above siNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

Vectors used to express the siNA molecules of the invention can encode one or both strands of an siNA duplex, or a single self-complementary strand that self hybridizes into an siNA duplex. The nucleic acid sequences encoding the siNA molecules of the instant invention can be operably linked in a manner that allows expression of the siNA molecule (see for example Paul et al., 2002, *Nature Biotechnology*, 19, 505; Miyagishi and Taira, 2002, *Nature Biotechnology*, 19, 497; Lee et al., 2002, *Nature Biotechnology*, 19, 500; and Novina et al., 2002, *Nature Medicine*, advance online publication doi:10.1038/nm725).

D. Carrier/Delivery Systems

The siNA molecules of the invention are added directly, or can be complexed with cationic lipids, packaged within liposomes, or as a recombinant plasmid or viral vectors which express the siNA molecules, or otherwise delivered to target cells or tissues. Methods for the delivery of nucleic acid molecules are described in Akhtar et al., 1992, *Trends Cell Bio.*, 2, 139; *Delivery Strategies for Antisense Oligonucleotide Therapeutics*, ed. Akhtar, 1995, Maurer et al., 1999, *Mol. Membr. Biol.*, 16, 129-140; Hofland and Huang, 1999, *Handb. Exp. Pharmacol.*, 137, 165-192; and Lee et al., 2000, *ACS Symp. Ser.*, 752, 184-192. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, *Bioconjugate Chem.*, 10, 1068-1074; Wang et al., International PCT Publication Nos. WO 03/47518 and WO 03/46185), poly(lactic-co-glycolic) acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722).

In one aspect, the present invention provides carrier systems containing the siNA molecules described herein. In some embodiments, the carrier system is a lipid-based carrier system, cationic lipid, or liposome nucleic acid complexes, a liposome, a micelle, a virosome, a lipid nanoparticle or a mixture thereof. In other embodiments, the carrier system is a polymer-based carrier system such as a cationic polymer-nucleic acid complex. In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system in a lipid nanoparticle formulation. Lipid nanoparticle ("LNP") formulations described in Table 10 can be applied to any siNA molecule or combination of siNA molecules herein.

In certain embodiment, the siNA molecules of the invention are formulated as a lipid nanoparticle composition such as is described in U.S. Ser. No. 11/353,630 and U.S. Ser. No. 11/586,102.

In some embodiments, the invention features a composition comprising an siNA molecule formulated as any of formulation LNP-051; LNP-053; LNP-054; LNP-069; LNP-073; LNP-077; LNP-080; LNP-082; LNP-083; LNP-060; LNP-061; LNP-086; LNP-097; LNP-098; LNP-099; LNP-100; LNP-101; LNP-102; LNP-103; or LNP-104 (see Table 10).

In other embodiments, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. Non-limiting, examples of such conjugates are described in U.S. Ser. No. 10/427,160 and U.S. Ser. No. 10/201,394; and U.S. Pat. Nos. 6,528,631; 6,335, 434; 6, 235,886; 6,153,737; 5,214,136; 5,138,045.

In various embodiments, polyethylene glycol (PEG) can be covalently attached to siNA compounds of the present invention. The attached PEG can be any molecular weight, preferably from about 100 to about 50,000 daltons (Da).

In yet other embodiments, the invention features compositions or formulations comprising surface-modified liposomes containing poly(ethylene glycol) lipids (PEG-modified, or long-circulating liposomes or stealth liposomes) and siNA molecules of the invention, such as is disclosed in for example, International PCT Publication No. WO 96/10391; Ansell et al., International PCT Publication No. WO 96/10390; Holland et al., International PCT Publication No. WO 96/10392).

In some embodiments, the siNA molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules of the invention are formulated as described in U.S. Patent Application Publication No. 20030077829.

In other embodiments, siNA molecules of the invention are complexed with membrane disruptive agents such as those described in U.S. Patent Application Publication No. 20010007666. In still other embodiments, the membrane disruptive agent or agents and the siNA molecule are also complexed with a cationic lipid or helper lipid molecule, such as those lipids described in U.S. Pat. No. 6,235,310.

In certain embodiments, siNA molecules of the invention are complexed with delivery systems as described in U.S. Patent Application Publication Nos. 2003077829; 20050287551; 20050164220; 20050191627; 20050118594; 20050153919; 20050085486; and 20030158133; and International PCT Publication Nos. WO 00/03683 and WO 02/087541.

In some embodiments, a liposomal formulation of the invention comprises an siNA molecule of the invention (e.g., siNA) formulated or complexed with compounds and compositions described in U.S. Pat. Nos. 6,858,224; 6,534,484; 6,287,591; 6,835,395; 6,586,410; 6,858,225; 6,815,432; 6,586,001; 6,120,798; 6,977,223; 6,998,115; 5,981,501; 5,976,567; 5,705,385; and U.S. Patent Application Publication Nos. 2006/0019912; 2006/0019258; 2006/0008909; 2005/0255153; 2005/0079212; 2005/0008689; 2003/0077829, 2005/0064595, 2005/0175682, 2005/0118253; 2004/0071654; 2005/0244504; 2005/0265961 and 2003/0077829.

Alternatively, recombinant plasmids and viral vectors, as discussed above, which express siRNA of the invention can be used to deliver the molecules of the invention. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell (for a review see Couture et al., 1996, *TIG.,* 12, 510). Such recombinant plasmids can also be administered directly or in conjunction with a suitable delivery reagents, including, for example, the Mirus Transit LT1 lipophilic reagent; lipofectin; lipofectamine; cellfectin; polycations (e.g., polylysine) or liposomes lipid-based carrier system, cationic lipid, or liposome nucleic acid complexes, a micelle, a virosome, a lipid nanoparticle.

E. Kits

The present invention also provides nucleic acids in kit form. The kit may comprise a container. The kit typically contains a nucleic acid of the invention with instructions for its administration. In certain instances, the nucleic acids may have a targeting moiety attached. Methods of attaching targeting moieties (e.g. antibodies, proteins) are known to those of skill in the art. In certain instances the nucleic acids is chemically modified. In other embodiments, the kit contains more than one siNA molecule of the invention. The kits may comprise an siNA molecule of the invention with a pharmaceutically acceptable carrier or diluent. The kits may further comprise excipients.

F. Therapeutic Uses/Pharmaceutical Compositions

The present body of knowledge in FCεR1α research indicates the need for methods to assay FCεR1α activity and for compounds that can regulate FCεR1α expression for research, diagnostic, and therapeutic use. As described infra, the nucleic acid molecules of the present invention can be used in assays to diagnose disease state related of FCεR1α levels. In addition, the nucleic acid molecules and pharmaceutical compositions can be used to treat disease states related to FCεR1α levels 1. Disease States Associated with FCεR1α

Particular disease states that can be associated with FCεR1α expression modulation include, but are not limited to, respiratory, inflammatory, and autoimmune disease, traits, conditions, and phenotypes. Non-limiting examples of such disease states or indications include Chronic Obstructive Pulmonary Disease (COPD), asthma, eosinophilic cough, bronchitis, acute and chronic rejection of lung allograft, sarcoidosis, pulmonary fibrosis, rhinitis and sinusitis. Each of the inflammatory respiratory diseases are all characterized by the presence of mediators that recruit and activate different inflammatory cells, which release enzymes or oxygen radicals causing symptoms, the persistence of inflammation and when chronic, destruction or disruption of normal tissue.

It is understood that the siNA molecules of the invention can degrade the target FCεR1α mRNA (and thus inhibit the diseases stated above). Inhibition of a disease can be evaluated by directly measuring the progress of the disease in a subject. It can also be inferred through observing a change or reversal in a condition associated with the disease. Additionally, the siNA molecules of the invention can be used as a prophylaxis. Thus, the use of the nucleic acid molecules and pharmaceutical compositions of the invention can be used to ameliorate, treat, prevent, and/or cure these diseases and others associated with regulation of FCεR1α.

2. Pharmaceutical Compositions

The siNA molecules of the instant invention provide useful reagents and methods for a variety of therapeutic, prophylactic, cosmetic, veterinary, diagnostic, target validation, genomic discovery, genetic engineering, and pharmacogenomic applications.

a. Formulations

Thus, the present invention, in one aspect, also provides for pharmaceutical compositions of the siNA molecules described. These pharmaceutical compositions include salts of the above compounds, e.g., acid addition salts, for example, salts of hydrochloric, hydrobromic, acetic acid, and benzene sulfonic acid. These pharmaceutical formulations or pharmaceutical compositions can comprise a pharmaceutically acceptable carrier or diluent.

In one embodiment, the invention features a pharmaceutical composition comprising an siNA molecule comprising at least 15 nucleotides of SEQ ID NO: 2. In another embodiment, the invention features a pharmaceutical composition comprising an siNA molecule comprising at least 15 nucleotides of SEQ ID NO: 131. In yet another embodiment, the invention features a pharmaceutical composition comprising an siNA molecule comprising at least 15 nucleotides of SEQ ID NO: 3. In still another embodiment, the invention features a pharmaceutical composition comprising an siNA molecule comprising at least 15 nucleotides of SEQ ID NO: 132. In another embodiment, the invention features a pharmaceutical composition comprising an siNA molecule comprising at least 15 nucleotides of SEQ ID NO: 5. In another embodiment, the invention features a pharmaceutical composition comprising an siNA molecule comprising at least 15 nucleotides of SEQ ID NO: 133. In another embodiment, the invention features a pharmaceutical composition comprising an siNA molecule comprising at least 15 nucleotides of SEQ ID NO: 8. In yet another embodiment, the invention features a pharmaceutical composition comprising an siNA molecule comprising at least 15 nucleotides of SEQ ID NO: 134. In another embodiment, the invention features a pharmaceutical composition comprising an siNA molecule comprising at least 15 nucleotides of SEQ ID NO: 9. In yet another embodiment, the invention features a pharmaceutical composition comprising an siNA molecule comprising at least 15 nucleotides of SEQ ID NO: 135. In another embodiment, the invention features a pharmaceutical composition comprising an siNA molecule comprising at least 15 nucleotides of SEQ ID NO: 17. In yet another embodiment, the invention features a pharmaceutical composition comprising an siNA molecule comprising at least 15 nucleotides of SEQ ID NO: 136. In another embodiment, the invention features a pharmaceutical composition comprising an siNA molecule comprising SEQ ID NO: 41 and SEQ ID NO: 42. In still another embodiment, the invention features a pharmaceutical composition comprising an siNA molecule comprising SEQ ID NO: 43 and SEQ ID NO: 44. In yet another embodiment, the invention features a pharmaceutical composition comprising an siNA molecule comprising SEQ ID NO: 47 and SEQ ID NO: 48. In yet another embodiment, the invention features a pharmaceutical composition comprising an siNA molecule comprising SEQ ID NO: 53 and SEQ ID NO: 54. In yet another embodiment, the invention features a pharmaceutical composition comprising an siNA molecule comprising SEQ ID NO: 55 and SEQ ID NO: 56. In still another embodiment, the invention features a pharmaceutical composition comprising an siNA molecule comprising SEQ ID NO: 71 and SEQ ID NO: 72. In still another embodiment, the invention features a pharmaceutical composition comprising an siNA molecule comprising formula (A).

The siNA molecules of the invention are preferably formulated as pharmaceutical compositions prior to administering to a subject, according to techniques known in the art. Pharmaceutical compositions of the present invention are characterized as being at least sterile and pyrogen-free. Methods for preparing pharmaceutical composition of the invention are within the skill in the art for example as described in *Remington's Pharmaceutical Science*, 17$^{th}$ ed., Mack Publishing Company, Easton, Pa. (1985).

In some embodiments, pharmaceutical compositions of the invention (e.g. siNA and/or LNP formulations thereof) further comprise conventional pharmaceutical excipients and/or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

Non-limiting examples of various types of formulations for local administration include ointments, lotions, creams, gels, foams, preparations for delivery by transdermal patches, powders, sprays, aerosols, capsules or cartridges for use in an inhaler or insufflator or drops (for example eye or nose drops), solutions/suspensions for nebulization, suppositories, pessaries, retention enemas and chewable or suckable tablets or pellets (for example for the treatment of aphthous ulcers) or liposome or microencapsulation preparations.

Ointments, creams and gels, can, for example, be formulated with an aqueous or oily base with the addition of suitable thickening and/or gelling agent and/or solvents. Non limiting examples of such bases can thus, for example, include water and/or an oil such as liquid paraffin or a vegetable oil such as arachis oil or castor oil, or a solvent such as polyethylene glycol. Thickening agents and gelling agents which can be used according to the nature of the base. Non-limiting examples of such agents include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

In one embodiment lotions can be formulated with an aqueous or oily base and will in general also contain one or more emulsifying agents, stabilizing agents, dispersing agents, suspending agents or thickening agents.

In one embodiment powders for external application can be formed with the aid of any suitable powder base, for example, talc, lactose or starch. Drops can be formulated with an aqueous or non-aqueous base also comprising one or more dispersing agents, solubilizing agents, suspending agents or preservatives.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate; or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

In other embodiments, the siNA and LNP compositions and formulations provided herein for use in pulmonary delivery further comprise one or more surfactants. Suitable surfactants or surfactant components for enhancing the uptake of the compositions of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly(vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

b. Combinations

The compound and pharmaceutical formulations according to the invention can be administered to a s subject alone or used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics, antivirals, or antihistamines. The invention thus provides, in a further embodiment, a combination comprising an siNA molecule of the invention, such as for example, but not limitation, an siNA molecule comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), or a pharmaceutically acceptable salt, solvate or physiologically functional derivative thereof together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. Other embodiments of the invention encompasses combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), or a pharmaceutically acceptable salt, solvate or physiologically functional derivative thereof together with a $\beta_2$-adrenoreceptor agonist, and/or an anticholinergic, and/or a FCεR1α inhibitor, and/or an antihistamine.

In one embodiment, the invention encompasses a combination comprising a siNA molecule of the invention together with a β2-adrenoreceptor agonist. Non-limiting examples of β2-adrenoreceptor agonists include salmeterol (which can be a racemate or a single enantiomer such as the R-enantiomer), salbutamol (which can be a racemate or a single enantiomer such as the R-enantiomer), formoterol (which can be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the β2-adrenoreceptor agonists are long-acting β2-adrenoreceptor agonists, for example, compounds which provide effective bronchodilation for about 12 hours or longer.

Other β2-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Further examples of β2-adrenoreceptor agonists include 3-(4-{[6-({(2R)-2-hydroxy-2-[4-hydroxy-3-(hydroxymethyl)phenyl]ethyl}amino)hexyl]oxy}butyl)benzenesulfonamide; 3-(3-{[7-({(2R)-2-hydroxy-2-[4-hydroxy-3-hydroxymethyl)phenyl]ethyl}-amino)heptyl]oxy}propyl)benzenesulfonamide; 4-{(1R)-2-[(6-{2-[(2,6-dichlorobenzyl)oxy]ethoxy}hexyl)amino]-1-hydroxyethyl}-2-(hydroxymethyl)phenol; 4-{(1R)-2-[(6-{4-[3-(cyclopentylsulfonyl)phenyl]butoxy}hexyl)amino]-1-hydroxyethyl}-2-(hydroxymethyl)phenol; N-[2-hydroxyl-5-[(1R)-1-hydroxy-2-[[2-4-[[(2R)-2-hydroxy-2phenylethyl]amino]phenyl]ethyl]amino]ethyl]phenyl]formamide; N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In one embodiment, the β2-adrenoreceptor agonist can be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, naphthaleneacrylic, benzoic, 4-methoxybenzoic, 2- or 4-hydroxybenzoic, 4-chlorobenzoic and 4-phenylbenzoic acid.

Suitable anti-inflammatory agents also include corticosteroids. Examples of corticosteroids which can be used in combination with the compounds of the invention are those oral and inhaled corticosteroids and their pro-drugs which have anti-inflammatory activity. Non-limiting examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, 6α,9α-difluoro-11β-hydroxy-16α-methyl-3-oxo-17α-(2,2,3,3 tetramethycyclopropyl-carbonyl)oxy-androsta-1,4-diene-17β-carbothioic acid S-cyanomethyl ester and 6α,9α-difluoro-11β-hydroxy-16α-methyl-17α-(1-methycyclopropyl-carbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclo-propylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester. Non-limiting examples of corticosteroids include those described in the following published patent applications and patents: WO02/088167, WO02/100879, WO02/12265, WO02/12266, WO05/005451, WO05/005452, WO06/072599 and WO06/072600.

In one embodiment, are combinations comprising siNA molecules of the invention and non-steroidal compounds having glucocorticoid agonism that can possess selectivity for transrepression over transactivation such as non-steroidal compounds disclosed in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870.

Non-limiting examples of other anti-inflammatory agents that can be used in combination with the siNA molecules of the invention include non-steroidal anti-inflammatory drugs (NSAID's).

Non-limiting examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. In one embodiment, the invention encompasses iNOS (inducible nitric oxide synthase) inhibitors for oral administration. Examples of iNOS inhibitors include those disclosed in the following published international patents and patent applications: WO93/13055, WO98/30537, WO02/50021, WO95/34534 and WO99/62875. Examples of CCR3 inhibitors include those disclosed in WO02/26722.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxy-phenyl)cyclohexan-1-one and cis-[4-cyano-4-(3-cyclopropylmethoxy-4-difluoromethoxy-phenyl) cyclohexan-1-ol]. Also, cis-4-cyano-4-[3-(cyclopentyloxy)-4-methoxyphenyl]cyclo-hexane-1-carboxylic acid (also known as cilomilast) and its salts, esters, pro-drugs or physical forms, which is described in U.S. Pat. No. 5,552,438

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropyl-benzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585. Further compounds are disclosed in the published international patent applications WO04/024728 (Glaxo Group Ltd), WO04/056823 (Glaxo Group Ltd) and WO04/103998 (Glaxo Group Ltd).

Example of cystic fibrous agents that can be use in combination with the compounds of the invention include, but are not limited to, compounds such as Tobi® and Pulmozyme®.

Examples of anticholinergic agents that can be used in combination with the compounds of the invention are those compounds that act as antagonists at the muscarinic receptors, in particular those compounds which are antagonists of the M1 or M3 receptors, dual antagonists of the M1/M3 or M2/M3, receptors or pan-antagonists of the M1/M2/M3 receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds of formula (XXI), which are disclosed in U.S. patent application 60/487,981:

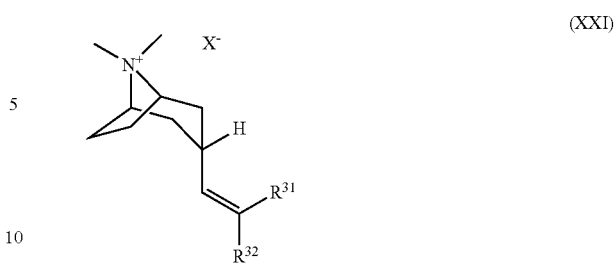

in which the preferred orientation of the alkyl chain attached to the tropane ring is endo; $R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms; $X^-$ represents an anion associated with the positive charge of the N atom. $X^-$ can be but is not limited to chloride, bromide, iodide, sulfate, benzene sulfonate, and toluene sulfonate. Examples of formula XXI include, but are not limited to, (3-endo)-3-(2,2-di-2-thienylethenyl)-8,8-dimethyl-8-azoniabicyclo[3.2.1]octane bromide; (3-endo)-3-(2,2-diphenylethenyl)-8,8-dimethyl-8-azoniabicyclo[3.2.1]octane bromide; (3-endo)-3-(2,2-diphenylethenyl)-8,8-dimethyl-8-azoniabicyclo[3.2.1]octane 4-methylbenzene-sulfonate; (3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further anticholinergic agents include compounds of formula (XXII) or (XXIII), which are disclosed in U.S. patent application 60/511,009:

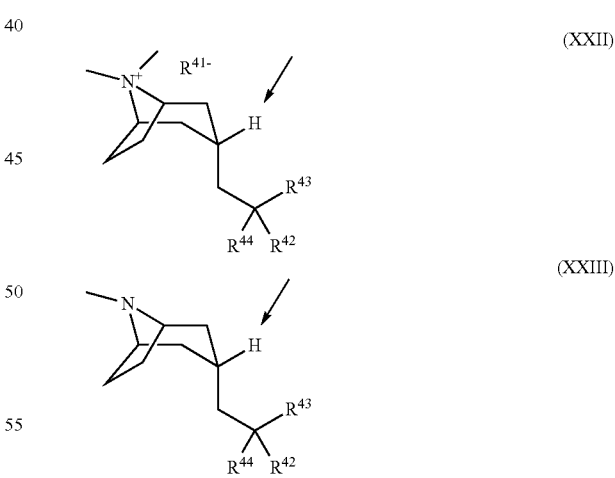

wherein: the H atom indicated is in the exo position; $R^{41}$ represents an anion associated with the positive charge of the N atom. $R^{41}$ can be, but is not limited to, chloride, bromide, iodide, sulfate, benzene sulfonate and toluene sulfonate; $R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl; $R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cyclo alkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —CN, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$, —$CH_2N(R^{48})SO_2(R^{46})$, —$CH_2N(R^{48})CO_2(R^{45})$, —$CH_2N(R^{48})CONH(R^{47})$; $R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl; $R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl; $R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, representative, but non-limiting, examples include: (endo)-3-(2-methoxy-2,2-di-thiophen-2-yl-ethyl)-8,8-dimethyl-8-azonia-bicyclo[3.2.1]octane iodide; 3-((endo)-8-methyl-8-aza-bicyclo[3.2.1]oct-3-yl)-2,2-diphenyl-propionitrile; (endo)-8-methyl-3-(2,2,2-triphenyl-ethyl)-8-azabicyclo[3.2.1]oct-ane; 3-((endo)-8-methyl-8-aza-bicyclo[3.2.1]oct-3-yl)-2,2-diphenylpropionamide; 3-((endo)-8-methyl-8-aza-bicyclo[3.2.1]oct-3-yl)-2,2-diphenyl-propionic acid; (endo)-3-(2-cyano-2,2-di-phenyl-ethyl)-8,8-dimethyl-8-azonia-bicyclo[3.2.1]octane iodide; (endo)-3-(2-cyano-2,2-diphenyl-ethyl)-8,8-dimethyl-8-azonia-bicyclo[3.2.1]octane bromide; 3-((endo)-8-methyl-8-aza-bicyclo[3.2.1]oct-3-yl)-2,2-diphenyl-propan-1-ol; N-benzyl-3-((endo)-8-methyl-8-aza-bicyclo[3.2.1]oct-3-yl)-2,2-diphenyl-propionamide; (endo)-3-(2-carbamoyl-2,2-diphenyl-ethyl)-8,8-dimethyl-8-azonia-bicyclo[3.2.1]octane iodide; 1-benzyl-3-[3-((endo)-8-methyl-8-azabicyclo[3.2.1]oct-3-yl)-2,2-diphenyl-propyl]-urea; 1-ethyl-3-[3-((endo)-8-methyl-8-aza-bicyclo[3.2.1]oct-3-yl)-2,2-di-phenyl-propyl]-urea; N-[3-((endo)-8-methyl-8-aza-bicyclo[3.2.1]oct-3-yl)-2,2-diphenyl-propyl]-acetamide; N-[3-((endo)-8-methyl-8-aza-bicyclo[3.2.1]oct-3-yl)-2,2-diphenyl-propyl]-benzamide; 3-((endo)-8-methyl-8-aza-bicyclo[3.2.1]oct-3-yl)-2,2-di-thiophen-2-yl-propionitrile; (endo)-3-(2-cyano-2,2-di-thiophen-2-yl-ethyl)-8,8-dimethyl-8-azonia-bicyclo[3.2.1]octaneiodide; N-[3-((endo)-8-methyl-8-aza-bicyclo[3.2.1]oct-3-yl)-2,2-diphenyl-propyl]-benzenesulfonamide; [3-((endo)-8-methyl-8-aza-bicyclo[3.2.1]oct-3-yl)-2,2-diphenyl-propyl]-urea; N-[3-((endo)-8-methyl 8-aza-bicyclo[3.2.1]oct-3-yl)-2,2-diphenyl-propyl]-methanesulfonamide; and/or (endo)-3-{2,2-diphenyl-3-[(1-phenyl-methanoyl)-amino]-propyl}-8,8-dimethyl-8-azoniabicyclo[3.2.1]octane bromide.

Further compounds include: (endo)-3-(2-methoxy-2,2-di-thiophen-2-yl-ethyl)-8,8-di-methyl-8-azonia-bicyclo[3.2.1]octane iodide; (endo)-3-(2-cyano-2,2-diphenyl-ethyl)-8,8-di-methyl-8-azonia-bicyclo[3.2.1]octane iodide; (endo)-3-(2-cyano-2,2-diphenyl-ethyl)-8,8-di-methyl-8-azonia-bicyclo[3.2.1]octane bromide; (endo)-3-(2-carbamoyl-2,2-diphenyl-ethyl)-8,8-dimethyl-8-azonia-bicyclo[3.2.1]octane iodide; (endo)-3-(2-cyano-2,2-di-thiophen-2-yl-ethyl)-8,8-dimethyl-8-azonia-bicyclo[3.2.1]octane iodide; and/or (endo)-3-{2,2-diphenyl-3-[(1-phenyl-methanoyl)-amino]-propyl}-8,8-dimethyl-8-azonia-bicyclo[3.2.1]octane bromide.

In certain embodiments, the invention provides a combination comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

In other embodiments, the invention provides a combination comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which can be used in combination with the compounds of the present invention include antagonists (and/or inverse agonists) of the H4 receptor, for example, the compounds disclosed in Jablonowski et al., J. Med. Chem. 46:3957-3960 (2003).

The invention thus provides a combination comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with a FCεR1α inhibitor.

The invention also provides, in a further embodiments, combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with a β2-adrenoreceptor agonist.

The invention also provides, in a further embodiments, combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with a corticosteroid.

The invention also provides, in a further embodiments, combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with an anticholinergic.

The invention provides, in a further aspect, combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with an antihistamine.

The invention provides, in yet a further aspect, combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with an FCεR1α inhibitor and a β2-adrenoreceptor agonist.

The invention thus provides, in a further aspect, combinations comprising an siNA molecule of the invention comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and/or a pharmaceutically acceptable salt, solvate or physiologically functional derivative thereof together with an anticholinergic and a FCεR1α inhibitor.

The combinations referred to above can conveniently be presented for use in the form of a pharmaceutical formulation and thus pharmaceutical compositions comprising a combination as defined above together with a pharmaceutically acceptable diluent or carrier represent a further aspect of the invention.

The individual compounds of such combinations can be administered either sequentially or simultaneously in separate or combined pharmaceutical formulations. In one embodiment, the individual compounds will be administered simultaneously in a combined pharmaceutical formulation.

In a further embodiment, the siNA molecules can be used in combination with other known treatments to prevent or treat respiratory diseases, disorders, or conditions in a subject or organism. For example, the siNa molecules of the invention can be used with additional airway hydration therapies such as hypertonic saline, denufosol, bronchitol; CFTR gene therapy; protein assist/repair such as CFTR correctors, e.g. VX-809 (Vertex), CFTR potentiators, e.g. VX-770 (Vertex); mucus treatments such as pulmozyme; anti-inflammatory treatments such as oral N-acetylcysteine, sildenafil, inhaled glutathione, pioglitazone, hydroxychloroquine, simvastatin; anti-infective therapies such as azithromycin, arikace; transplant drugs such as inhaled cyclosporin; and nutritional supplements such as aquADEKs, pancrelipase products, trizytek. Thus, the described molecules could be used in combination with one or more known compounds, treatments, or procedures to prevent or treat diseases, disorders, conditions, and traits described herein in a subject or organism as are known in the art, such as other FCεR1α inhibitors.

3. Therapeutic Applications

The present body of knowledge in FCεR1α research indicates the need for methods that can regulate FCεR1α expression for therapeutic use.

Thus, one aspect of the invention comprises a method of treating a subject including, but not limited to, a human suffering from a condition which is mediated by the action, or by loss of action, of FCεR1α, which method comprises administering to said subject an effective amount of a double-stranded siNA molecule of the invention. In one embodiment of this aspect, the siNA molecules comprises at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A). In another embodiment of this aspect, the condition is or is caused by a respiratory disease. Respiratory diseases treatable according to this aspect of the invention include COPD, asthma, eosinophilic cough, bronchitis, sarcoidosis, pulmonary fibrosis, rhinitis, sinusitis. In a particular embodiment, the use is for the treatment of a respiratory disease selected from the group consisting of COPD, cystic fibrosis, and asthma. In certain embodiments, the administration of the siNA molecule is via local administration or systemic administration. In other embodiments, the invention features contacting the subject or organism with an siNA molecule of the invention via local administration to relevant tissues or cells, such as lung cells and tissues, such as via pulmonary delivery. In yet other embodiments the invention features contacting the subject or organism with an siNA molecule of the invention via systemic administration (such as via intravenous or subcutaneous administration of siNA) to relevant tissues or cells, such as tissues or cells involved in the maintenance or development of the inflammatory disease, trait, or condition in a subject or organism.

siNA molecules of the invention are also used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more genes in the cells or tissue, such that the cells or tissue obtain a desired phenotype or are able to perform a function when transplanted in vivo. In one embodiment, certain FCεR1α target cells from a patient are extracted. These extracted cells are contacted with FCεR1α siNAs targeting a specific nucleotide sequence within the cells under conditions suitable for uptake of the siNAs by these cells (e.g., using delivery reagents such as cationic lipids, liposomes and the like or using techniques such as electroporation to facilitate the delivery of siNAs into cells). The cells are then reintroduced back into the same patient or other patients.

For therapeutic applications, a pharmaceutically effective dose of the siNA molecules or pharmaceutical compositions of the invention is administered to the subject. A pharmaceutically effective dose is that dose required to prevent, inhibit the occurrence, or treat (alleviate a symptom to some extent, preferably all of the symptoms) of a disease state. One skilled in the art can readily determine a therapeutically effective dose of the siNA of the invention to be administer to a given subject, by taking into account factors, such as the size and weight of the subject, the extent of the disease progression or penetration, the age, health, and sex of the subject, the route of administration m and whether the administration is regional or systemic. Generally, an amount between 0.1 mg/kg and 100 mg/kg body weight/day of active ingredients is administered dependent upon potency of the negatively charged polymer. The siNA molecules of the invention can be administered in a single dose or in multiple doses.

G. Administration

Compositions or formulations can be administered in a variety of ways. Non-limiting examples of administration methods of the invention include oral, buccal, sublingual, parenteral (i.e., intraarticularly, intravenously, intraperitoneally, subcutaneously, or intramuscularly), local rectal administration or other local administration. In one embodiment, the composition of the invention can be administered by insufflation and inhalation. Administration can be accomplished via single or divided doses. In some embodiments, the pharmaceutical compositions are administered intravenously or intraperitoneally by a bolus injection (see, e.g., U.S. Pat. No. 5,286,634). The lipid nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)). In one embodiment, the siNA molecules of the invention and formulations or compositions thereof are administered to a cell, subject, or organism as is described herein and as is generally known in the art.

1. In Vivo Administration

In any of the methods of treatment of the invention, the siNA can be administered to the subject systemically as described herein or otherwise known in the art, either alone as a monotherapy or in combination with additional therapies described herein or as are known in the art. Systemic administration can include, for example, pulmonary (inhalation, nebulization etc.) intravenous, subcutaneous, intramuscular, catheterization, nasopharangeal, transdermal, or oral/gastrointestinal administration as is generally known in the art.

In one embodiment, in any of the methods of treatment or prevention of the invention, the siNA can be administered to the subject locally or to local tissues as described herein or otherwise known in the art, either alone as a monotherapy or in combination with additional therapies as are known in the art. Local administration can include, for example, inhalation, nebulization, catheterization, implantation, direct injection, dermal/transdermal application, patches, stenting, ear/eye drops, or portal vein administration to relevant tissues, or any other local administration technique, method or procedure, as is generally known in the art.

The compounds of the invention can in general be given by internal administration in cases wherein systemic glucocorticoid receptor agonist therapy is indicated.

In one embodiment, the siNA molecules of the invention and formulations or compositions thereof are administered to the liver as is generally known in the art (see for example Wen et al., 2004, *World J Gastroenterol.*, 10, 244-9; Murao et al., 2002, *Pharm Res.*, 19, 1808-14; Liu et al., 2003, *gene Ther.*, 10, 180-7; Hong et al., 2003, *J Pharm Pharmacol.*, 54, 51-8; Herrmann et al., 2004, *Arch Virol.*, 149, 1611-7; and Matsuno et al., 2003, *gene Ther.*, 10, 1559-66).

In one embodiment, the invention features the use of methods to deliver the siNA molecules of the instant invention to hematopoietic cells, including monocytes and lymphocytes. These methods are described in detail by Hartmann et al., 1998, *J. Phamacol. Exp. Ther.*, 285(2), 920-928; Kronenwett et al., 1998, *Blood*, 91(3), 852-862; Filion and Phillips, 1997, *Biochim. Biophys. Acta.*, 1329(2), 345-356; Ma and Wei, 1996, *Leuk. Res.*, 20(11/12), 925-930; and Bongartz et al., 1994, *Nucleic Acids Research*, 22(22), 4681-8.

In one embodiment, the siNA molecules of the invention and formulations or compositions thereof are administered directly or topically (e.g., locally) to the dermis or follicles as is generally known in the art (see for example Brand, 2001, *Curr. Opin. Mol. Ther.*, 3, 244-8; Regnier et al., 1998, *J. Drug Target*, 5, 275-89; Kanikkannan, 2002, *BioDrugs*, 16, 339-47; Wraight et al., 2001, *Pharmacol. Ther.*, 90, 89-104; and Preat and Dujardin, 2001, STP PharmaSciences, 11, 57-68). In one embodiment, the siNA molecules of the invention and formulations or compositions thereof are administered directly or topically using a hydroalcoholic gel formulation comprising an alcohol (e.g., ethanol or isopropanol), water, and optionally including additional agents such isopropyl myristate and carbomer 980. In other embodiments, the siNA are formulated to be administered topically to the nasal cavity. Topical preparations can be administered by one or more applications per day to the affected area; over skin areas occlusive dressings can advantageously be used. Continuous or prolonged delivery can be achieved by an adhesive reservoir system.

In one embodiment, an siNA molecule of the invention is administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In one embodiment, the siNA molecules of the invention and formulations or compositions thereof are administered to the lung as is described herein and as is generally known in the art. In another embodiment, the siNA molecules of the invention and formulations or compositions thereof are administered to lung tissues and cells as is described in U.S. Patent Publication Nos. 2006/0062758; 2006/0014289; and 2004/0077540.

2. Aerosols and Delivery Devices a. Aerosol Formulations

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In one embodiment, the siNA molecules of the invention and formulations thereof are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the siNA compositions of the invention can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Spray compositions comprising siNA molecules or compositions of the invention can, for example, be formulated as aqueous solutions or suspensions or as aerosols delivered from pressurized packs, such as a metered dose inhaler, with the use of a suitable liquefied propellant. In one embodiment, aerosol compositions of the invention suitable for inhalation can be either a suspension or a solution and generally contain an siNA molecule comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition can optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment a pharmaceutical aerosol formulation of the invention comprising a compound of the invention and a fluorocarbon or hydrogen-containing chlorofluorocarbon or mixtures thereof as propellant, optionally in combination with a surfactant and/or a co-solvent.

The aerosol formulations of the invention can be buffered by the addition of suitable buffering agents.

Aerosol formulations can include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions of the invention (e.g., siNA and/or LNP formulations thereof). In another embodiment, a device comprising a nebulizer delivers a composition of the invention (e.g., siNA and/or LNP formulations thereof) comprising fluorochemicals that are bacteriostatic thereby decreasing the potential for microbial growth in compatible devices.

Capsules and cartridges comprising the composition of the invention for use in an inhaler or insufflator, of for example gelatine, can be formulated containing a powder mix for inhalation of a compound of the invention and a suitable powder base such as lactose or starch. In one embodiment, each capsule or cartridge contain an siNA molecule comprising at least 15 nucleotides of SEQ ID NO: 2, SEQ ID NO: 131, SEQ ID NO: 3, SEQ ID NO: 132, SEQ ID NO: 5, SEQ ID NO: 133, SEQ ID NO: 8, SEQ ID NO: 134, SEQ ID NO: 9, SEQ ID NO: 135, SEQ ID NO: 17, or SEQ ID NO: 136; or comprising SEQ ID NO: 41 and SEQ ID NO: 42, or SEQ ID NO: 43 and SEQ ID NO: 44, or SEQ ID NO: 47 and SEQ ID NO: 48, or SEQ ID NO: 53 and SEQ ID NO: 54, or SEQ ID NO: 55 and SEQ ID NO: 56, or SEQ ID NO: 71 and SEQ ID NO: 72 or formula (A), and one or more excipients. In another embodiment, the compound of the invention can be presented without excipients such as lactose The aerosol compositions of the present invention can be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range can be from 1 to 5 microns. In another embodiment, the particulate range can be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

In some embodiments, an siNA composition of the invention is administered topically to the nose for example, for the treatment of rhinitis, via pressurized aerosol formulations, aqueous formulations administered to the nose by pressurized pump or by nebulization. Suitable formulations contain water as the diluent or carrier for this purpose. In certain embodiments, the aqueous formulations for administration of the composition of the invention to the lung or nose can be provided with conventional excipients such as buffering agents, tonicity modifying agents and the like.

b. Devices

The siNA molecules of the invention can be formulated and delivered as particles and/or aerosols as discussed above and dispensed from various aerosolization devices known by those of skill in the art.

Aerosols of liquid or non-liquid particles comprising an siNA molecule or formulation of the invention can be produced by any suitable means, such as with a device comprising a nebulizer (see for example U.S. Pat. No. 4,501,729) such as ultrasonic or air jet nebulizers. In one embodiment, the nebulizer for administering an siNA molecule of the invention, relies on oscillation signals to drive a piezoelectric ceramic oscillator for producing high energy ultrasonic waves which mechanically agitate a composition of the invention (e.g., siNA and/or LNP formulations thereof) generating a medicament aerosol cloud. (See for example, U.S. Pat. Nos. 7,129,619 B2 and 7,131,439 B2). In another embodiment, the nebulizer relies on air jet mixing of compressed air with a composition of the invention (e.g., siNA and/or LNP formulations thereof) to form droplets in an aerosol cloud.

Nebulizer devices used with the siNA molecules or formulations of the invention can use carriers, typically water or a dilute aqueous or non-aqueous solution comprising siNA molecules of the invention. One embodiment of the invention is a device comprising a nebulizer that uses an alcoholic solution, preferably made isotonic with body fluids by the addition of, for example, sodium chloride or other suitable salts which comprises an siNA molecule or formulation of the invention. In another embodiment, the nebulizer devices comprises one or more non-aqueous fluorochemical carriers comprising an siNA molecule or formulation of the invention.

Solid particle aerosols comprising an siNA molecule or formulation of the invention and surfactant can be produced with any solid particulate aerosol generator. In one embodiment, aerosol generators are used for administering solid particulate agents to a subject. These generators produce particles which are respirable, as explained below, as a predetermined metered dose of a composition. Certain embodiments of the invention comprise an aerosol comprising a combination of particulates having at least one siNA molecule or formulation of the invention with a pre-determined volume of suspension medium or surfactant to provide a respiratory blend. Other embodiments of the invention, comprise an aerosol generator that comprises an siNA molecule or formulation of the invention.

One type of solid particle aerosol generator used with the siNA molecules of the invention is an insufflator. Suitable formulations for administration by insufflation include finely comminuted powders which can be delivered by means of an insufflator. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. A second type of illustrative aerosol generator comprises a metered dose inhaler ("MDI")

MDIs are pressurized aerosol dispensers, typically containing a suspension or solution formulation of the active ingredient in a liquefied propellant. During use, these devices discharge the formulation through a valve adapted to deliver a metered volume to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, for example US Patent Application No. 20040037780, and U.S. Pat. Nos. 6,592,904; 6,582,728; 6,565,885.

The canisters of a MDI typically comprise a container capable of withstanding the vapor pressure of the propellant used, such as a plastic or plastic-coated glass bottle or preferably a metal can, for example, aluminum or an alloy thereof which can optionally be anodized, lacquer-coated and/or plastic-coated (for example incorporated herein by reference WO96/32099 wherein part or all of the internal surfaces are coated with one or more fluorocarbon polymers optionally in combination with one or more non-fluorocarbon polymers, such as for example, but not limitation, a polymer blend of polytetrafluoroethylene (PTFE) and polyethersulfone (PES)), which container is closed with a metering valve. The metering valves are designed to deliver a metered amount of the formulation per actuation and incorporate a gasket to prevent leakage of propellant through the valve. The gasket can comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

MDIs containing siNA molecules or formulations taught herein can be prepared by methods of the art (for example, see Byron, above and WO96/32099).

The MDIs used with the siNA molecules of the invention can also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

The siNA molecules can also be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. In one embodiment of the invention are provided fluid dispensers, which use reservoirs of multiple metered doses of a fluid formulation, the doses being dispensable upon sequential pump actuations, and which comprise siNA molecules or formulations of the invention. In certain embodiments, the dispensing nozzle or orifice of the dispenser can be configured for insertion into the nostrils of the user for spray dispensing of the fluid formulation comprising siNA molecules or formulations into the nasal cavity. A fluid dispenser of the aforementioned type is described and illustrated in WO05/044354. The dispenser has a housing which houses a fluid discharge device having a compression pump mounted on a container for containing a fluid formulation. In various embodiments, the housing of the dispenser has at least one finger-operable side lever which is movable inwardly with respect to the housing to cam the container upwardly in the housing to cause the pump to compress and pump a metered dose of the formulation out of a pump stem through a nasal nozzle of the housing. In another embodiment, the fluid dispenser is of the general type illustrated in FIGS. 30-40 of WO05/044354.

In certain embodiments of the invention, nebulizer devices are used in applications for conscious, spontaneously breathing subjects, and for controlled ventilated subjects of all ages. The nebulizer devices can be used for targeted topical and systemic drug delivery to the lung. In one embodiment, a device comprising a nebulizer is used to deliver an siNA molecule or formulation of the invention locally to lung or pulmonary tissues. In another embodiment, a device comprising a nebulizer is used to deliver a an siNA molecule or formulation of the invention systemically.

In other embodiments, nebulizer devices are used to deliver respiratory dispersions comprising emulsions, microemulsions, or submicron and nanoparticulate suspensions of at least one active agent. (See for example U.S. Pat. Nos. 7,128, 897 and 7,090,830 B2).

Nebulizer devices can be used to administer aerosols comprising as siNA molecule or formulation of the invention continuously or periodically and can be regulated manually, automatically, or in coordination with a patient's breathing. (See U.S. Pat. No. 3,812,854, WO 92/11050). For example, periodical administer a siNA molecule of the invention can given as a single-bolus via a microchannel extrusion chamber or via cyclic pressurization. Administration can be once daily or several times daily, for example 2, 3, 4 or 8 times, giving for example 1, 2 or 3 doses each time. The overall daily dose and the metered dose delivered by capsules and cartridges in an inhaler or insufflator will generally be double that delivered with aerosol formulations.

H. Other Applications/Uses of siNA Molecules of the Invention

The siNA molecules of the invention can also be used for diagnostic applications, research applications, and/or manufacture of medicants.

In one aspect, the invention features a method for diagnosing a disease, trait, or condition in a subject comprising administering to the subject a composition of the invention under conditions suitable for the diagnosis of the disease, trait, or condition in the subject.

In one embodiment, siNA molecules of the invention are used to down regulate or inhibit the expression of FCεR1α proteins arising from haplotype polymorphisms that are associated with a trait, disease or condition in a subject or organism. Analysis of FCεR1α genes, or FCεR1α protein or RNA levels can be used to identify subjects with such polymorphisms or those subjects who are at risk of developing traits, conditions, or diseases described herein. These subjects are amenable to treatment, for example, treatment with siNA molecules of the invention and any other composition useful in treating diseases related to target gene expression. As such, analysis of FCεR1α protein or RNA levels directly or indirectly can be used to determine treatment type and the course of therapy in treating a subject. Monitoring of FCεR1α protein or RNA levels can be used to predict treatment outcome and to determine the efficacy of compounds and compositions that modulate the level and/or activity of certain FCεR1α proteins associated with a trait, disorder, condition, or disease.

In another embodiment, the invention comprises use of a double-stranded nucleic acid according to the invention for use in the manufacture of a medicament. In an embodiment, the medicament is for use in treating a condition that is mediated by the action, or by loss of action, of FCεR1α. In one embodiment, the medicament is for use for the treatment of a respiratory disease. In an embodiment the medicament is for use for the treatment of a respiratory disease selected from the group consisting of COPD, cystic fibrosis, asthma, eosinophilic cough, bronchitis, sarcoidosis, pulmonary fibrosis, rhinitis, and sinusitis. In a particular embodiment, the use is for the treatment of a respiratory disease selected from the group consisting of COPD, cystic fibrosis, and asthma.

In certain embodiments, siNAs 25473-DC, 25474-DC, 25476-DC, 25479-DC, 25480-DC, 25488-DC, and siNAs wherein at least one strand comprises at least 15 nucleotides of SEQ ID NO: 2, SEQ ID NO: 3, SEQ ID NO: 5, SEQ ID NO: 8, SEQ ID NO: 9, SEQ ID NO: 17, SEQ ID NO: 131, SEQ ID NO: 132; SEQ ID NO: 133, SEQ ID NO: 134, SEQ ID NO: 135, or SEQ ID NO: 136, and the siNAs comprising Formula A are for use in a method for treating respiratory disease, such as, for example but not limitation, COPD, cystic fibrosis, asthma, eosinophilic cough, bronchitis, sarcoidosis, pulmonary fibrosis, rhinitis, and sinusitis.

I. Examples

The invention will now be illustrated with the following non-limiting examples. Those of skill in the art will readily recognize a variety of non-critical parameters which can be changed or modified to yield essential the same results.

Example 1

Design, Synthesis, and Identification of siNAs Active Against FCεR1α FCεR1α siNA Synthesis A series of 38 siNA molecules were designed, synthesized and evaluated for efficacy against FCεR1α. The primary criteria for design of FCεR1α for human siNAs were (i) homology between two species (human and mouse) and (ii) high efficacy scores as determined by a proprietary algorithm. Mouse sequences were also looked at for use in animal models. The effects of the siNAs on FCεR1α RNA levels were also examined. The sequences of the siNAs that were designed, synthesized, and evaluated for efficacy against FCεR1α are described in Table 1a (target sequences) and Table 1b (modified sequences).

TABLE 1a

FCεR1α Target Sequences, noting target sites. The Homology column indicates perfect homology of the siRNA with the human transcript (h), with only the mouse transcript (m) to both the human and mouse transcript (hm) or perfect homology to one transcript (h or m) with the number of mismatches (1 or 2 mm) to the other transcript (e.g. h 1 mm m, means perfect homology to human with 1 mismatch to mouse).

| Duplex ID | Target Sequence | Target Site | Homology | SEQ ID NO: |
|---|---|---|---|---|
| 25472-DC | GCUCAAGGAUUUAUAGAAA | 976 | h | 1 |
| 25473-DC | CUUGCAAUAUACAUAGAAA | 950 | h | 2 |
| 25474-DC | CCAUGGAAUAGAAUAUUUA | 208 | h (1 mm m) | 3 |
| 25475-DC | GGGAUGUGUACAAGGUGAU | 512 | h | 4 |
| 25476-DC | CCCUCAACAUUACUGUAAU | 665 | h | 5 |
| 25477-DC | CGUCUGUGCUCAAGGAUUU | 969 | h | 6 |
| 25478-DC | GCAUGGGCCUAUAUUUGAA | 34 | h | 7 |
| 25479-DC | UCAGCACCAACAAGUUAAU | 378 | h | 8 |
| 25480-DC | ACAGGAUUAUUUAUCUCAA | 757 | h | 9 |
| 25481-DC | CCUCCAUGGAAUAGAAUAU | 205 | h | 10 |
| 25482-DC | CCUCAACAUUACUGUAAUA | 666 | h | 11 |
| 25483-DC | CCCAAAAACAACUGAUAUA | 859 | h | 12 |
| 25484-DC | CACCGAGCAUGGGCCUAUA | 28 | h | 13 |
| 25485-DC | GGUUGAAUAAAUGAGAGAA | 1058 | h | 14 |
| 25486-DC | CAGUGGAGAAUACAAAUGU | 360 | h | 15 |

TABLE 1a-continued

FCεR1α Target Sequences, noting target sites. The Homology column indicates perfect homology of the siRNA with the human transcript (h), with only the mouse transcript (m) to both the human and mouse transcript (hm) or perfect homology to one transcript (h or m) with the number of mismatches (1 or 2 mm) to the other transcript (e.g. h 1 mm m, means perfect homology to human with 1 mismatch to mouse).

| Duplex ID | Target Sequence | Target Site | Homology | SEQ ID NO: |
|---|---|---|---|---|
| 25487-DC | UGGGAACAAUUUCUUUGAA | 255 | h | 16 |
| 25488-DC | UGGUGGUGAUUCUGUUUGC | 731 | h (1 mm m) | 17 |
| 25489-DC | UUGGUGGUGAUUCUGUUUG | 730 | h (1 mm m) | 18 |
| 25490-DC | AGAGUGAACCUGUGUACCU | 398 | h (2 mm m) | 19 |
| 25491-DC | UGGCUGCUCCUUCAGGCCU | 433 | h (2 mm m) | 20 |
| 25492-DC | UUGUUGGUGGUGAUUCUGU | 727 | h (1 mm m) | 21 |
| 25493-DC | UAUUUAAGGAGAGAAUGU | 221 | h (2 mm m) | 22 |
| 25494-DC | GACCCACCAUGGAUUAGAA | 136 | m | 23 |
| 25495-DC | CCACCAUGGAUUAGAAUAU | 139 | m | 24 |
| 25496-DC | GGAACAAUCACCUUCAAAU | 191 | m | 25 |
| 25497-DC | UGGGAACAAUCACCUUCAA | 189 | m | 26 |
| 25498-DC | CAGUGGAAAAUACAUAUGU | 297 | m | 27 |
| 25499-DC | AUGGGAACAAUCACCUUCA | 188 | m | 28 |
| 25500-DC | GUGGAAAAUACAUAUGUCA | 299 | m | 29 |
| 25501-DC | GCUGGAAGAACUGGAAUGU | 437 | m | 30 |
| 25502-DC | CCUGUGUACUUGAAUGUAA | 343 | m | 31 |
| 25503-DC | GUGGCACCUACCACUGCAA | 545 | m | 32 |
| 25504-DC | GAUACAUAUAGGAACUAAU | 792 | m | 33 |
| 25505-DC | CUCAUGUGAUCCCUAGAAA | 886 | m | 34 |
| 25506-DC | AGUGGAAAAUACAUAUGUC | 298 | m | 35 |
| 25507-DC | UCAGAAGCAAGGAUUGUUU | 315 | m | 36 |
| 25508-DC | UAAAUAGCAAAUACUCAAU | 972 | m | 37 |
| 25509-DC | GCCUAGCACUGCUGUUCAU | 68 | m | 38 |

For each oligonucleotide of a target sequence, the two individual, complementary strands of the siRNA were synthesized separately using solid phase synthesis, then purified separately by reversed phase solid phase extraction (SPE). The complementary strands were annealed to form the double strand (duplex) and delivered in the desired concentration and buffer of choice.

Briefly, the single strand oligonucleotides were synthesized using phosphoramidite chemistry on an automated solid-phase synthesizer, as is generally known in the art (see for example U.S. Ser. No. 12/064,014). A synthesis column was packed with solid support derivatized with the first nucleoside residue. Synthesis was initiated by detritylation of the acid labile 5'-O-dimethoxytrityl group to release the 5'-hydroxyl. Phosphoramidite and a suitable activator in acetonitrile were delivered simultaneously to the synthesis column resulting in coupling of the amidite to the 5'-hydroxyl. The column was then washed with acetonitrile. Iodine solution was pumped through the column to oxidize the phosphite triester linkage P(III) to its phosphotriester P(V) analog. Unreacted 5'-hydroxyl groups were capped using reagents such as acetic anhydride in the presence of 2,6-lutidine and N-methylimidazole. The elongation cycle was resumed with the detritylation step for the next phosphoramidite incorporation. This process was repeated until the desired sequence was synthesized. The synthesis concluded with the final 5'-terminus protecting group (trityl or 5'-O-dimethoxytrityl).

Upon completion of the synthesis, the solid-support and associated oligonucleotide was dried under argon pressure or vacuum. Aqueous base was added and the mixture was heated to effect cleavage of the succinyl linkage, removal of the cyanoethyl phosphate protecting group, and deprotection of the exocyclic amine protection.

The following process is performed on single strands that do not contain ribonucleotides. After treating the solid support with the aqueous base, the mixture is filtered to separate the solid support from the deprotected crude synthesis material. The solid support is then rinsed with water, which is combined with the filtrate. The resultant basic solution allows for retention of the 5'-O-dimethoxytrityl group to remain on the 5' terminal position (trityl-on).

For single strands that contain ribonucleotides, the following process was performed. After treating the solid support with the aqueous base, the mixture was filtered to separate the solid support from the deprotected crude synthesis material. The solid support was then rinsed with dimethylsulfoxide (DMSO), which was combined with the filtrate. Fluoride reagent, such as triethylamine trihydrofluoride, was added to the mixture, and the solution was heated. The reaction was quenched with suitable buffer to provide a solution of crude single strand with the 5'-O-dimethoxytrityl group on the final 5' terminal position.

The trityl-on solution of each crude single strand was purified using chromatographic purification, such as SPE RPC purification. The hydrophobic nature of the trityl group permits stronger retention of the desired full-length oligo than the non-tritylated truncated failure sequences. The failure sequences were selectively washed from the resin with a suitable solvent, such as low percent acetonitrile. Retained oligonucleotides were then detritylated on-column with trifluoroacetic acid to remove the acid-labile trityl group. Residual acid was washed from the column, a salt exchange was performed, and a final desalting of the material commenced. The full-length oligo was recovered in a purified form with an aqueous-organic solvent. The final product was then analyzed for purity (HPLC), identity (Maldi-TOF MS), and yield (UV $A_{260}$). The oligos were dried via lyophilization or vacuum condensation.

Annealing:

Based on the analysis of the product, the dried oligos were dissolved in appropriate buffers followed by mixing equal molar amounts (calculated using the theoretical extinction coefficient) of the sense and antisense oligonucleotide strands. The solution was then analyzed for purity of duplex by chromatographic methods and desired final concentration. If the analysis indicated an excess of either strand, then the additional non-excess strand was titrated until duplexing was complete. When analysis indicated that the desired product purity has been achieved the material was delivered and ready for use.

Below is a table showing various siNAs synthesized using this protocol.

TABLE 1b

FCεR1α siNA Strands Synthesized

| Duplex ID | Target Site | SEQ ID NO: | Target Sequence | Modified Sequence | SEQ ID NO: |
|---|---|---|---|---|---|
| 25472-DC | 976 | 1 | GCUCAAGGAUUUAUAGAAA | B GcucAAGGAuuuAuAGAAA TTB | 39 |
| 25472-DC | 976 | 1 | GCUCAAGGAUUUAUAGAAA | UUUcuAuAAAuccuuGAGcUU | 40 |
| 25473-DC | 950 | 2 | CUUGCAAUAUACAUAGAAA | B cuuGcAAuAuAcAUAGAAA TTB | 41 |
| 25473-DC | 950 | 2 | CUUGCAAUAUACAUAGAAA | UUUcuAuGuAuAuuGcAAGUU | 42 |
| 25474-DC | 208 | 3 | CCAUGGAAUAGAAUAUUUA | B ccAuGGAAuAGAAuAuuuA TTB | 43 |
| 25474-DC | 208 | 3 | CCAUGGAAUAGAAUAUUUA | UAAAuAuucuAuuccAuGGUU | 44 |
| 25475-DC | 512 | 4 | GGGAUGUGUACAAGGUGAU | B GGGAuGuGuAcAAGGuGAu TTB | 45 |
| 25475-DC | 512 | 4 | GGGAUGUGUACAAGGUGAU | AUCAccuuGuAcAcAucccUU | 46 |
| 25476-DC | 665 | 5 | CCCUCAACAUUACUGUAAU | B cccucAAcAuuAcuGuAAu TTB | 47 |
| 25476-DC | 665 | 5 | CCCUCAACAUUACUGUAAU | AUUAcAGuAAuGuuGAGGGUU | 48 |
| 25477-DC | 969 | 6 | CGUCUGUGCUCAAGGAUUU | B cGucuGuGcucAAGGAuuu TTB | 49 |
| 25477-DC | 969 | 6 | CGUCUGUGCUCAAGGAUUU | AAAuccuuGAGcAcAGAcGUU | 50 |
| 25478-DC | 34 | 7 | GCAUGGGCCUAUAUUUGAA | B GcAuGGGccuAuAuuuGAA TTB | 51 |
| 25478-DC | 34 | 7 | GCAUGGGCCUAUAUUUGAA | UUCAAAAuAuAGGcccAuGcUU | 52 |
| 25479-DC | 378 | 8 | UCAGCACCAACAAGUUAAU | B ucAGcAccAAcAAGuuAAu TTB | 53 |
| 25479-DC | 378 | 8 | UCAGCACCAACAAGUUAAU | AUUAAcuuGuuGGuGcuGAUU | 54 |
| 25480-DC | 757 | 9 | ACAGGAUUAUUUAUCUCAA | B AcAGGAuuAuuuAucucAA TTB | 55 |
| 25480-DC | 757 | 9 | ACAGGAUUAUUUAUCUCAA | UUGAGAuAAAuAAuccuGuUU | 56 |
| 25481-DC | 205 | 10 | CCUCCAUGGAAUAGAAUAU | B ccuccAuGGAAuAGAAuAu TTB | 57 |
| 25481-DC | 205 | 10 | CCUCCAUGGAAUAGAAUAU | AUAuucuAuuccAuGGAGGUU | 58 |
| 25482-DC | 666 | 11 | CCUCAACAUUACUGUAAUA | B ccucAAcAuuAcuGuAAuA TTB | 59 |
| 25482-DC | 666 | 11 | CCUCAACAUUACUGUAAUA | UAUuAcAGuAAuGuuGAGGUU | 60 |
| 25483-DC | 859 | 12 | CCCAAAAACAACUGAUAUA | B cccAAAAAcAAcuGAuAuA TTB | 61 |
| 25483-DC | 859 | 12 | CCCAAAAACAACUGAUAUA | UAUAucAGuuGuuuuuGGGUU | 62 |
| 25484-DC | 28 | 13 | CACCGAGCAUGGGCCUAUA | B cAccGAGcAuGGGccuAuA TTB | 63 |
| 25484-DC | 28 | 13 | CACCGAGCAUGGGCCUAUA | UAUAGGcccAuGcucGGuGUU | 64 |
| 25485-DC | 1058 | 14 | GGUUGAAUAAAUGAGAGAA | B GGuuGAAuAAAuGAGAGAA TTB | 65 |
| 25485-DC | 1058 | 14 | GGUUGAAUAAAUGAGAGAA | UUCucucAuuuAuucAAccUU | 66 |
| 25486-DC | 360 | 15 | CAGUGGAGAAUACAAAUGU | B cAGuGGAGAAuAcAAAuGu TTB | 67 |
| 25486-DC | 360 | 15 | CAGUGGAGAAUACAAAUGU | ACAuuuGuAuucuccAcuGUU | 68 |
| 25487-DC | 255 | 16 | UGGGAACAAUUUCUUUGAA | B uGGGAAcAAuuucuuuGAA TTB | 69 |
| 25487-DC | 255 | 16 | UGGGAACAAUUUCUUUGAA | UUCAAAGAAAuuGuucccAUU | 70 |
| 25488-DC | 731 | 17 | UGGUGGUGAUUCUGUUUGC | B uGGuGGuGAuucuGuuuGc TTB | 71 |
| 25488-DC | 731 | 17 | UGGUGGUGAUUCUGUUUGC | GCAAAcAGAAucAccAccAUU | 72 |
| 25489-DC | 730 | 18 | UUGGUGGUGAUUCUGUUUG | B uuGGuGGuGAuucuGuuuG TTB | 73 |
| 25489-DC | 730 | 18 | UUGGUGGUGAUUCUGUUUG | CAAAcAGAAucAccAccAAUU | 74 |
| 25490-DC | 398 | 19 | AGAGUGAACCUGUGUACCU | B AGAGuGAAccuGuGuAccu TTB | 75 |
| 25490-DC | 398 | 19 | AGAGUGAACCUGUGUACCU | AGGuAcAcAGGuucAcucuUU | 76 |

TABLE 1b-continued

FCεR1α siNA Strands Synthesized

| Duplex ID | Target Site | SEQ ID NO: | Target Sequence | Modified Sequence | SEQ ID NO: |
|---|---|---|---|---|---|
| 25491-DC | 433 | 20 | UGGCUGCUCCUUCAGGCCU | B uGGcuGcuccuucAGGccu TTB | 77 |
| 25491-DC | 433 | 20 | UGGCUGCUCCUUCAGGCCU | AGGccuGAAGGAGcAGccAUU | 78 |
| 25492-DC | 727 | 21 | UUGUUGGUGGUGAUUCUGU | B uuGuuGGuGGuGAuucuGu TTB | 79 |
| 25492-DC | 727 | 21 | UUGUUGGUGGUGAUUCUGU | ACAGAAuCAccAccAAcAAUU | 80 |
| 25493-DC | 221 | 22 | UAUUUAAAGGAGAGAAUGU | B uAuuuAAAGGAGAGAAuGu TTB | 81 |
| 25493-DC | 221 | 22 | UAUUUAAAGGAGAGAAUGU | ACAuucucuccuuuAAAuAUU | 82 |
| 25494-DC | 136 | 23 | GACCCACCAUGGAUUAGAA | B GAcccAccAuGGAuuAGAA TTB | 83 |
| 25494-DC | 136 | 23 | GACCCACCAUGGAUUAGAA | UUCuAAuccAuGGuGGGucUU | 84 |
| 25495-DC | 139 | 24 | CCACCAUGGAUUAGAAUAU | B ccAccAuGGAuuAGAAuAu TTB | 85 |
| 25495-DC | 139 | 24 | CCACCAUGGAUUAGAAUAU | AUAuucuAAuccAuGGuGGUU | 86 |
| 25496-DC | 191 | 25 | GGAACAAUCACCUUCAAAU | B GGAAcAAucAccuucAAAu TTB | 87 |
| 25496-DC | 191 | 25 | GGAACAAUCACCUUCAAAU | AUUuGAAGGuGAuuGuuccUU | 88 |
| 25497-DC | 189 | 26 | UGGGAACAAUCACCUUCAA | B uGGGAAcAAucAccuucAA TTB | 89 |
| 25497-DC | 189 | 26 | UGGGAACAAUCACCUUCAA | UUGAAGGuGAuuGuucccAUU | 90 |
| 25498-DC | 297 | 27 | CAGUGGAAAAUACAUAUGU | B cAGuGGAAAAuAcAuAuGu TTB | 91 |
| 25498-DC | 297 | 27 | CAGUGGAAAAUACAUAUGU | ACAuAuGuAuuuccAcuGUU | 92 |
| 25499-DC | 188 | 28 | AUGGGAACAAUCACCUUCA | B AuGGGAAcAAucAccuucA TTB | 93 |
| 25499-DC | 188 | 28 | AUGGGAACAAUCACCUUCA | UGAAGGuGAuuGuucccAuUU | 94 |
| 25500-DC | 299 | 29 | GUGGAAAAUACAUAUGUCA | B GuGGAAAAuAcAuAuGucA TTB | 95 |
| 25500-DC | 299 | 29 | GUGGAAAAUACAUAUGUCA | UGAcAuAuGuAuuuuccAcUU | 96 |
| 25501-DC | 437 | 30 | GCUGGAAGAACUGGAAUGU | B GcuGGAAGAAcuGGAAuGu TTB | 97 |
| 25501-DC | 437 | 30 | GCUGGAAGAACUGGAAUGU | ACAuuccAGuucuuccAGcUU | 98 |
| 25502-DC | 343 | 31 | CCUGUGUACUUGAAUGUAA | B ccuGuGuAcuuGAAuGuAA TTB | 99 |
| 25502-DC | 343 | 31 | CCUGUGUACUUGAAUGUAA | UUAcAuucAAGuAcAcAGGUU | 100 |
| 25503-DC | 545 | 32 | GUGGCACCUACCACUGCAA | B GuGGcAccuAccAcuGcAA TTB | 101 |
| 25503-DC | 545 | 32 | GUGGCACCUACCACUGCAA | UUGcAGuGGuAGGuGccAcUU | 102 |
| 25504-DC | 792 | 33 | GAUACAUAUAGGAACUAAU | B GAuAcAuAuAGGAAcuAAu TTB | 103 |
| 25504-DC | 792 | 33 | GAUACAUAUAGGAACUAAU | AUUAGuuccuAuAuGuAucUU | 104 |
| 25505-DC | 886 | 34 | CUCAUGUGAUCCCUAGAAA | B cAcAuGuGAucccuAGAAA TTB | 105 |
| 25505-DC | 886 | 34 | CUCAUGUGAUCCCUAGAAA | UUUcuAGGGAucAcAuGAGUU | 106 |
| 25506-DC | 298 | 35 | AGUGGAAAAUACAUAUGUC | B AGuGGAAAAuAcAuAuGuc TTB | 107 |
| 25506-DC | 298 | 35 | AGUGGAAAAUACAUAUGUC | GACAuAuGuAuuuuccAcuUU | 108 |
| 25507-DC | 315 | 36 | UCAGAAGCAAGGAUUGUUU | B ucAGAAGcAAGGAuuGuuu TTB | 109 |
| 25507-DC | 315 | 36 | UCAGAAGCAAGGAUUGUUU | AAAcAAuccuuGcuucuGAUU | 110 |
| 25508-DC | 972 | 37 | UAAAUAGCAAAUACUCAAU | B uAAAuAGcAAAuAcucAAu TTB | 111 |
| 25508-DC | 972 | 37 | UAAAUAGCAAAUACUCAAU | AUUGAGuAuuuGcuAuuuAUU | 112 |

TABLE 1b-continued

FCɛR1α siNA Strands Synthesized

| Duplex ID | Target Site | SEQ ID NO: | Target Sequence | Modified Sequence | SEQ ID NO: |
|---|---|---|---|---|---|
| 25509-DC | 68 | 38 | GCCUAGCACUGCUGUUCAU | B G*c*cu*A*G*c*A*c*uG*c*uG*u*uc*A*u TTB | 113 |
| 25509-DC | 68 | 38 | GCCUAGCACUGCUGUUCAU | AUG<u>A</u><u>A</u>c<u>A</u>G*c*<u>A</u>G*u*G*c*u<u>A</u>GG*c*<u>UU</u> | 114 | wherein:
A, C, G, and U = ribose A, C, G or U
c and u = 2'-deoxy-2'-fluoro C or U
<u>A</u>, <u>U</u> and <u>G</u> = 2'-O-methyl (2'-OMe) A U or G
A and *G* = deoxy A or G
B = inverted abasic
T = thymidine Further Synthesis Steps for Commercial Preparation Once analysis indicates that the desired product purity has been achieved after the annealing step, the material is transferred to the tangential flow filtration (TFF) system for concentration and desalting, as opposed to doing this prior to the annealing step.

Ultrafiltration: The annealed product solution is concentrated using a TFF system containing an appropriate molecular weight cut-off membrane. Following concentration, the product solution is desalted via diafiltration using Milli-Q water until the conductivity of the filtrate is that of water.

Lyophilization: The concentrated solution is transferred to a bottle, flash frozen and attached to a lyophilizer. The product is then freeze-dried to a powder. The bottle is removed from the lyophilizer and is now ready for use.

Initial Screening Protocol (96-Well Plate Transfections)

Cell Culture Preparation:

All cells were obtained from ATCC (Manassas, Va.) unless otherwise indicated. Cells were grown and transfected under standard conditions, which are detailed below for each cell line.

LAD2 (human; provided by GSK): Cells were cultured at 37° C. in the presence of 5% $CO_2$ and grown in Stem pro-34 SFM media (Invitrogen cat#10640-019) supplemented with stem pro34 nutrient supplement (1:40 dilution, supplied), glutamine (2 mM), penicillin (100 units/ml), streptomycin (100 µg/ml) and 100 ng/ml of Human Stem Cell Factor (SCF) (R&D Systems cat#255-SC).

MC9 (mouse; ATCC cat# CRL-8306): Cells were cultured at 37° C. in the presence of 5% $CO_2$ and grown in RPMI 1640 supplemented with 10% FCS, glutamine (2 mM), penicillin (100 units/ml), streptomycin (100 µg/ml), and 10% Rat T-STIM with ConA (BD Biosciences cat#354115).

LAD2 Transfection and Screening

Cells were plated in all wells of a tissue-culture treated, 96-well plate at a final count of 30,000 cells/well in 100 µL of the appropriate culture media. Cells were transfected on the day of seeding.

Complexes containing siNA and RNAiMax were created as follows: A solution of RNAiMax diluted 33-fold in OPTI-MEM was prepared. In parallel, solutions of the siNAs for testing were prepared to a final concentration of 120 nM in OPTI-MEM. After incubation of RNAiMax/OPTI-MEM solution at room temperature for 5 min, an equal volume of the siNA solution and the RNAiMax solution were added together for each of the siNAs.

Mixing resulted in a solution of siNA/RNAiMax where the concentration of siNA was 60 nM. This solution was incubated at room temperature for 20 minutes. After incubation, 20 uL of the solution was added to each of the relevant wells.

The final concentration of siNA in each well was 10 nM and the final volume of RNAiMax in each well was 0.3 ul.

The time of incubation with the RNAiMax-siNA complexes was 72 hours and there was no change in media between transfection and harvesting, unless otherwise indicated.

Dose response curves were carried out in a similar fashion in 96-well plates, while maintaining a constant amount of RNAiMax in each transfection.

MC9 Transfection and Screening

In all experiments the siNA concentration was 10 nM.

Experiment 1:

Cells were plated in all wells of V-shaped tissue-culture treated, 96-well plates at final counts of 10,000 and 30,000 cells/well in 100 µL of appropriate culture media. Transfection was performed on the day of seeding in the similar fashion as described above. The time of incubation with the RNAiMax-siNA complexes was 72 hours.

Experiment 2:

Cells were transfected using Human Monocyte Kit (AMAXA cat# VPA-1007) according to manufacturer's instructions. Two different cell densities were used: 50,000 and 100,000 cells/transfection reaction. RNA was harvested 24 hours post-transfection.

Experiment 3:

Cells were transfected using 96-well Nucleofector Kit with SF reagent (AMAXA cat #VHCA-1002) at 50,000, 100,000, and 150,000 cells/reaction according to manufacturer's protocol. The time of incubation was 24 h.

Experiments 4 and 5:

Cells were transfected using 96-well Nucleofector Kit with SF reagent (AMAXA cat #VHCA-1002) at 200,000 cells/reaction according to manufacturer's protocol. RNA was isolated 48 and 72 hours post-transfection.

6-Well Plate Transfections (for Protein Extraction)

LAD2 cells were plated in 6-well plates at final count of 300,000 cells/well in 2 ml of complete growth media. Transfection was performed on the day of seeding using RNAiMax; final concentration of siRNAs was 30, 5, 0.8, 0.14, 0.023, and 0.004 nM. The amount of RNAiMax in each well was 2.5 uL. Protein lysates were harvested 72 hours post-transfection using PARIS Kit (Ambion, cat#1921) according to manufacturer's instructions. Protein concentration was measured using a Bradford Quick Start Kit (Bio-Rad, cat#500-0205).

RNA Isolation and Reverse Transcription (96-Well Plate)

RNA was extracted from a 96-well plate using the Taq-Man® Gene Expression Cells-to-CT™ Kit (Cat#4399002) with a modified protocol. Briefly, a 60 uL (1 plate) or 110 uL (2 plates) of the Lysis Solution with DNase I was dispensed into each well of the Lysis Buffer Plate (twin.tec full skirt plate). The lysis buffer and stop plates were stored at 4° C. until the cells were washed.

The plate was spun at 1100 rpm for 5 minutes. The culture medium was aspirated and discarded from the wells of the culture plate. The lysis was performed automatically using a BioMek FX instrument and method. After the Biomek method was completed, the lysis plate was incubated for 2 min. at room temperature. The lysis plate can be stored for 2 hours at 4° C., or at −20° C. or −80° C. for two months.

Each well of the reverse transcription plate required 10 uL of 2× reverse transcriptase Buffer, 1 uL of 20× reverse transcription enzyme and 2 uL of nuclease-free water. The reverse transcription master mix was prepared by mixing 2× reverse transcription buffer, 20× reverse transcription enzyme mix, and nuclease-free water. 13 uL of the reverse transcription master mix was dispensed into each well of the reverse transcription plate (semi-skirted). A separate reverse transcription plate was prepared for each cell plate. The plate was loaded onto a Biomek NX or Biomek FX Dual −96 and the Biomek method was run. The program is programmed to automatically added 7 uL of lysate from the cell lysis procedure described above into each well of the reverse transcription plate. The plate is sealed and spun on a centrifuge (1000 rpm for 30 seconds) to settle the contents to the bottom of the reverse transcription plate. The plate is placed in a thermocycler at 37° C. for 60 min, 95° C. for 5 min, and 4° C. until the plate is removed from the thermocycler. Upon removal, if not used immediately, the plate was frozen at −20° C.

Quantitative RT-PCR (Taqman)

A series of probes and primers were used to detect the various mRNA transcripts of the genes of FCεR1α, FCεR1γ, and GAPDH in mouse and human cell lines (see Table 2). All the Taqman probes and primers for the experiments here-in described except for human FCεR1α were supplied as pre-validated sets by Applied Biosystems, Inc. (see Table 2). The assays were performed on an ABI 7900 instrument, according to the manufacturer's instructions.

TABLE 2

Probes and primers used to carry out Real-Time RT/PCR (Taqman) reactions for FCεR1α and FCεR1γ mRNA analysis.

| Species | Gene | Probe/Primer | SEQ ID NO: |
|---------|------|--------------|------------|
| Human | FCεR1α | Forward: 5'-TACTCTACTGT GTGTAGCCTTACTGTTCTTC 3'<br>Reverse: 5' GAGGGTTCAAG GAGACCTTAGGTT 3'<br>Probe: 5' CTCCAGATGGCGT GTTAGCAGTCCCTC 3' | 137<br>138<br>139 |
| Human | FCεR1γ | ABI Cat. #Hs00175408_m1 | |
| Human | GAPDH | ABI Cat. #4310884E | |
| Mouse | FCεR1α | ABI Cat. #Mm00438867_m1 | |
| Mouse | GAPDH | ABI Cat. #4352339E | |

A TaqMan Gene Expression Master Mix (provided in the Cells-to-CT™, Applied Biosystems, Cat #4399002) was used. The PCR reactions were carried out at 50° C. for 2 min, 95° C. for 20 min followed by 40 cycles at 95° C. for 15 secs and 60° C. for 1 min.

Within each experiment, the baseline was set in the exponential phase of the amplification curve, and based on the intersection point of the baselines with the amplification curve, a Ct value was assigned by the instrument.

FCεR1α Western Blot

The protein source for the Western Blot experiments were from transfection of LAD2 cells in a 6 well plate, as described above.

Samples were diluted 1:1 in 2× Laemmli buffer with 5% β-mercapto-ethanol and incubated at 95° C. for 5 minutes. 15 ug of protein was loaded in each lane of 10% Tris-HCl gel. One lane was designated for MagicMark Protein Standard (Invitrogen # LC5602). The gel was run at 100V for approximately 2 hours. Proteins were transferred to a PVDF membrane at 100V for 60 minutes. Once the transfer was finished, the membrane was blocked in 1% Casein in PBS (BioRad Cat#161-0783) for 1 hour on a plate rocker at room temperature followed by the overnight incubation at 4° C. with rabbit polyclonal anti-FCεR1α primary antibody (Upstate, cat#06-725) diluted 1:1000 in 1% Casein. On the next day, the blot was washed 4×5 minutes in PBST solution and incubated for 30 minutes at room temperature with goat anti-rabbit secondary antibody (Jackson ImmunoResearch, cat#111-035-144) diluted 1:20,000 in 1% Casein. Then, the blot was washed 4×5 minutes with PBST and incubated for 1 minute with ECL Western Blotting Substrate (Pierce Biotechnology, Cat#32106). The bands were visualized on the Bio-Rad VersaDoc Imager.

The Western Blots assays as described above, were used to confirm that the siNA molecules of the invention reduced the protein level of FCεR1α.

Calculations

The expression level of the gene of interest and % knockdown was calculated using Comparative Ct method:

$$\Delta Ct = Ct_{Target} - Ct_{GAPDH}$$

$$\Delta\Delta Ct = \Delta Ct_{(Target\ siRNA)} - \Delta Ct_{(NTC)}$$

Relative expression level = $2^{-\Delta\Delta Ct}$ $$\% KD = 100 \times (1 - 2^{-\Delta\Delta Ct})$$

The non-targeting control siNA was, unless otherwise indicated, chosen as the value against which to calculate the % knock-down, because it is the most relevant control.

Additionally, only normalized data, which reflects the general health of the cell and quality of the RNA extraction, was examined. This was done by looking at the level of two different mRNAs in the treated cells, the first being the target mRNA and the second being the normalizer mRNA. This allowed for elimination of siNAs that might be potentially toxic to cells rather than solely knocking down the gene of interest. This was done by comparing the Ct for GAPDH in each well relative to the Ct for the entire plate.

All calculations of $IC_{50}$s were performed using SigmaPlot 10.0 software. The data were analyzed using the sigmoidal dose-response (variable slope) equation for simple ligand binding. In all of the calculations of the % knock-down, the calculation was made relative to the normalized level of expression of the gene of interest in the samples treated with the non-targeting control (Ctrl siNA) unless otherwise indicated.

Results:

The FCεR1α siNAs were designed and synthesized as described previously. The siNAs were screened in human LAD2 cells. The data from the screen of FCεR1α siNAs in human cells is shown in Table 3. The screen was performed at 72 hrs post-transfection.

TABLE 3

Summary of screening data in human LAD2 Cells (n = 3)
% KD LAD2 cells is represented as mean ± S.D.

| Duplex ID | Target Site | Homology | % KD LAD2 Cells |
|---|---|---|---|
| 25472-DC | 976 | h | 75 ± 2.6 |
| 25473-DC | 950 | h | 78 ± 7.7 |
| 25474-DC | 208 | h (1 mm m) | 76 ± 15 |
| 25475-DC | 512 | h | 77 ± 9.6 |
| 25476-DC | 665 | h | 84 ± 5.1 |
| 25477-DC | 969 | h | 74 ± 10. |
| 25478-DC | 34 | h | −1 ± 20. |
| 25479-DC | 378 | h | 85 ± 3.9 |
| 25480-DC | 757 | h | 81 ± 8.9 |
| 25481-DC | 205 | h | 71 ± 3.6 |
| 25482-DC | 666 | h | 73 ± 3.7 |
| 25483-DC | 859 | h | 58 ± 8.7 |
| 25484-DC | 28 | h | −3 ± 0.8 |
| 25485-DC | 1058 | h | 75 ± 0.5 |
| 25486-DC | 360 | h | 47 ± 15. |
| 25487-DC | 255 | h | 70 ± 1.3 |
| 25488-DC | 731 | h (1 mm m) | 80 ± 1.5 |
| 25489-DC | 730 | h (1 mm m) | 2. ± 3.9 |
| 25490-DC | 398 | h (2 mm m) | 25 ± 14. |
| 25491-DC | 433 | h (2 mm m) | 19 ± 1.6 |
| 25492-DC | 727 | h (1 mm m) | 21 ± 5.5 |
| 25493-DC | 221 | h (2 mm m) | 67 ± 1.4 |
| 25494-DC | 136 | m | 66 ± 3.9 |
| 25495-DC | 139 | m | 7. ± 8.1 |
| 25496-DC | 191 | m | 0. ± 10. |
| 25497-DC | 189 | m | −1 ± 1.3 |
| 25498-DC | 297 | m | 24 ± 10. |
| 25499-DC | 188 | m | 0. ± 12. |
| 25500-DC | 299 | m | 46 ± 2.3 |
| 25501-DC | 437 | m | −1 ± 13. |
| 25502-DC | 343 | m | 6. ± 4.1 |
| 25503-DC | 545 | m | 11 ± 12. |
| 25504-DC | 792 | m | −3 ± 5.0 |
| 25505-DC | 886 | m | 8. ± 18. |
| 25506-DC | 298 | m | 40 ± 0.7 |
| 25507-DC | 315 | m | −1 ± 13. |
| 25508-DC | 972 | m | 22 ± 4.8 |
| 25509-DC | 68 | m | −1 ± 0.7 |

Summary data, as to potency and efficacy for FCεR1α mRNA knock-down in human cells for certain siNA molecules, is presented in Table 4. Cells for the experiments were treated with 12 concentrations of siNA ranging from 0.083 fM to 30 nM. All of the data is presented as % knockdown of FCεR1α normalized against the expression of GAPDH mRNA expression level. Then the data was determined as a % knockdown relative to the non-targeting control siNA.

TABLE 4

Summary of efficacy (% KD) and potency ($IC_{50}$) of the FCεR1α mRNA knock-down of certain siNA in human LAD2 cells.

| Duplex ID | Homology | % KD LAD2 Cells 10 nM | Maximum % KD in DRC 30 nM | IC50 (pM) |
|---|---|---|---|---|
| 25473-DC | h | 78 ± 7.7 | 78 ± 12 | 42 ± 9.7 |
| 25474-DC | h (1 mm m) | 76 ± 15 | 87 ± 7 | 17 ± 4.2 |
| 25476-DC | h | 84 ± 5.1 | 83 ± 6 | 17 ± 3.0 |
| 25479-DC | h | 85 ± 3.9 | 84 ± 5 | 13 ± 3.7 |
| 25480-DC | h | 81 ± 8.9 | 79 ± 9 | 15 ± 3.4 |
| 25488-DC | h (1 mm m) | 80 ± 1.5 | 76 ± 8 | 46 ± 28 |

Each of the data are summarized from at three separate experiments (except 25474 where n = 2), and within each experiment, each data point is calculated from an n of 3. Values are mean ± standard deviation.

The specificity of these six siNAs was also assessed. These siNAs were tested at 10 nM concentration. The siNA tested did not show greater than 20% reduction of the FCεR1γ transcript.

Various siNAs were also evaluated for their potential to knock-down FCεR1α protein using Western Blots. The siNAs were tested at a single time point post-transfection (72 hrs). This was the time point at which the FCεR1α mRNA levels had previously been determined. The final concentration of siNAs was 30 nM. Lanes were loaded with 15 ug of total proteinProtein samples from the treated cells were used in Western blots with an α-FCεR1α antibody. Each of the FCεR1α bands detected was quantified and used to calculate the percentage reduction of protein for each siRNA treatment (see Table 5).

TABLE 5

Quantification of bands from FCεR1α Western blot.

| siNA | % Protein Reduction (30 nM) |
|---|---|
| 25473-DC | 74.4 |
| 25474-DC | 76.7 |
| 25476-DC | 74.5 |
| 25479-DC | 78 |
| 25480-DC | 90 |
| 25488-DC | 81 |
| UC3 | 0 |

Four of the siNAs from Table 5 were tested in for dose dependence. These siNAs showed a dose dependent reduction of FCεR1α protein. All four siRNAs tested showed a statistically significant reduction of protein ($P<0.05$) (at 30 nM) when compared to UC3 treated cells. In order to meet the assumption of group independence required by the statistical test, the density of the band for each treatment group was compared to the density of the control group using a t-test with equal variances. The equality of variances was confirmed by the F-test. The density is defined by the ratio between the total intensity of all pixels and the area of the rectangle drawn around each band (intensity/mm$^2$) and is calculated by the BioRad software. The average band densities±S.D. for each treatment and their respective p-values are listed in Table 6.

TABLE 6

Average band densities ± S.D. calculated for the four siNAs and Universal Control 3 at 30 nM concentration.

| Duplex ID | Density (Intensity/mm$^2$) | Two-tail p-value |
|---|---|---|
| 25473-DC (n = 2) | 38487 ± 12711 | 0.0124 |
| 25474-DC (n = 2) | 33904 ± 8392 | 0.0086 |
| 25479-DC (n = 3) | 37651 ± 9075 | 0.0028 |
| 25480-DC (n = 3) | 37871 ± 11725 | 0.0033 |
| UC3 (n = 5) | 102055 ± 21361 | na |

The data represents n = 2 for 25473-DC and 25474-DC, n = 3 for 25479-DC and 25480-DC, and n = 5 for Universal Control 3.

The density of the band detected by the FCεR1α antibody in samples treated with the active siRNAs is statistically significantly different from the density of the band detected in samples treated with the control siRNA.

Example 2

In Vivo Assessment of Actions of siNAs Administered Topically to the Airway

Following identification of active siNA constructs in vitro, the activities of the siNAs following topical administration to the airway can be assessed in a variety of laboratory species—a typical example is rat, using the methodology summarised below. siNA, an appropriate scrambled control, or vehicle are injected in 200 μl volume into the trachea, via a cannula placed trans-orally, whilst the animals are anaesthetised briefly using isoflurane (4.5% in oxygen) and nitrous oxide (anaesthetics delivered in a ratio of 1:3). In order to facilitate administration of material, animals are supine and placed on a dosing table at an angle of approximately 45° in order to facilitate visualisation of the airway via a cold light source placed over the throat. Alternatively, the anaesthetised animals are dosed intranasally via a pipette (dosing volume 25 μl per nostril). In other studies, conscious rodents are placed in a circular Perspex chamber and exposed to an aerosol of nebulised test material for at least 20 min. When each dosing procedure is completed, the animals are returned to standard holding cages and allowed free access to food and water. Groups of animals (typically n=4-6) are then humanely euthanatized by i.p. injection of pentobarbital at set intervals post dose. Samples of airway cells and tissue are removed immediately and placed in Trizol or RNAlater for subsequent mRNA extraction and analysis. In some studies airway tissue is fixed in 4% paraformaldehyde for subsequent histological analysis. In other experiments the airways are lavaged for analysis of infiltrating leukocyte populations and/or cytokine/mediator content. RNA extraction is carried out using standard methods and QRT-PCR used to quantify the expression of the target mRNA of interest between animals treated with active and control siRNA and to determine whether target knockdown had been achieved. In some cases, mRNA expression levels are normalized relative to either the housekeeping gene, GAPDH, or the epithelial specific marker, E-cadherin.

Preparation of Materials

Solutions of unformulated siNAs and scrambled controls are prepared in phosphate-buffered saline. A range of formulated materials can also been used—in each case the effects of an siNA are compared to that of an equivalent volume of scrambled control.

Example 3

Preparation of Nanoparticle Encapsulated siNA/Carrier Formulations

General LNP Preparation siNA nanoparticle solutions are prepared by dissolving siNAs and/or carrier molecules in 25 mM citrate buffer (pH 4.0) at a concentration of 0.9 mg/mL. Lipid solutions are prepared by dissolving a mixture of cationic lipid (e.g., CLinDMA or DOBMA, see structures and ratios for Formulations in Table 10), DSPC, Cholesterol, and PEG-DMG (ratios shown in Table 10) in absolute ethanol at a concentration of about 15 mg/mL. The nitrogen to phosphate ratio is approximate to 3:1.

Equal volume of siNA/carrier and lipid solutions are delivered with two FPLC pumps at the same flow rates to a mixing T connector. A back pressure valve is used to adjust to the desired particle size. The resulting milky mixture is collected in a sterile glass bottle. This mixture is then diluted slowly with an equal volume of citrate buffer, and filtered through an ion-exchange membrane to remove any free siNA/carrier in the mixture. Ultra filtration against citrate buffer (pH 4.0) is employed to remove ethanol (test stick from ALCO screen), and against PBS (pH 7.4) to exchange buffer. The final LNP is obtained by concentrating to a desired volume and sterile filtered through a 0.2 μm filter. The obtained LNPs are characterized in term of particle size, Zeta potential, alcohol content, total lipid content, nucleic acid encapsulated, and total nucleic acid concentration LNP Manufacture Process In a non-limiting example, a LNP-086 siNA/carrier formulation is prepared in bulk as follows. The process consists of (1) preparing a lipid solution; (2) preparing an siNA/carrier solution; (3) mixing/particle formation; (4) incubation; (5) dilution; (6) ultrafiltration and concentration.

1. Preparation of Lipid Solution

A 3-necked 2 L round bottom flask, a condenser, measuring cylinders, and two 10 L conical glass vessels are depyrogenated. The lipids are warmed to room temperature. Into the 3-necked round bottom flask is transferred 50.44 g of CLinDMA with a pipette and 43.32 g of DSPC, 5.32 g of Cholesterol, 6.96 g of PEG-DMG, and 2.64 g of linoleyl alcohol are added. To the mixture is added 1 L of ethanol. The round bottom flask is placed in a heating mantle that is connected to a J-CHEM process controller. The lipid suspension is stirred under Argon with a stir bar and a condenser on top. A thermocouple probe is put into the suspension through one neck of the round bottom flask with a sealed adapter. The suspension is heated at 30° C. until it became clear. The solution is allowed to cool to room temperature and transferred to a conical glass vessel and sealed with a cap.

2. Preparation of siNA/Carrier Solution

Into a sterile container, such as the Corning storage bottle, is weighed 3.6 g times the water correction factor (approximately 1.2) of siNA-1 powder. The siNA is transferred to a depyrogenated 5 L glass vessel. The weighing container is rinsed 3× with citrate buffer (25 mM, pH 4.0, and 100 mM NaCl) and the rinses are placed into the 5 L vessel, QS with citrate buffer to 4 L. The concentration of the siNA solution is determined with a UV spectrometer using the following procedure. 20 μL is removed from the solution, diluted 50 times to 1000 μL, and the UV reading recorded at A260 nm after blanking with citrate buffer. This is repeated. If the readings for the two samples are consistent, an average is taken and the concentration is calculated based on the extinction coefficients of the siNAs. If the final concentration are out of the range of 0.90±0.01 mg/mL, the concentration is adjusted by adding more siNA/carrier powder, or adding more citrate buffer. This process is repeated for the second siNA, siNA-2. Into a depyrogenated 10 L glass vessel, 4 L of each 0.9 mg/mL siNA solution is transferred.

Alternatively, if the siNA/carrier solution comprised a single siNA duplex and or carrier instead of a cocktail of two or more siNA duplexes and/or carriers, then the siNA/carrier is dissolved in 25 mM citrate buffer (pH 4.0, 100 mM of NaCl) to give a final concentration of 0.9 mg/mL.

The lipid/ethanol solution is then sterile/filtered through a Pall Acropak 20 0.8/0.2 μm sterile filter PN 12203 into a depyrogenated glass vessel using a Master Flex Peristaltic Pump Model 7520-40 to provide a sterile starting material for the encapsulation process. The filtration process is run at an 80 mL scale with a membrane area of 20 cm$^2$. The flow rate is 280 mL/min. This process is scaleable by increasing the tubing diameter and the filtration area.

3. Particle Formation—Mixing Step

An AKTA P900 pump is turned on and sanitized by placing 1000 mL of 1 N NaOH into a 1 L glass vessel and 1000 mL of 70% ethanol into a 1 L glass vessel and attaching the pump with a pressure lid to each vessel. A 2000 mL glass vessel is placed below the pump outlet and the flow rate is set to 40 mL/min for a 40 minute time period with argon flushing the system at 10 psi. When the sanitation is complete, the gas is turned off and the pump is stored in the solutions until ready for use. Prior to use, the pump flow is verified by using 200 mL of ethanol and 200 mL of sterile citrate buffer.

To the AKTA pump is attached the sterile lipid/ethanol solution, the sterile siNA/carrier or siNA/carrier cocktail/citrate buffer solution and a depyrogenated receiving vessel (2× batch size) with lid. The gas is turned on and the pressure maintained between 5 to 10 psi during mixing.

4. Incubation

The solution is held after mixing for a 22±2 hour incubation. The incubation is done at room temperature (20-25° C.) and the in-process solution was protected from light.

5. Dilution

The lipid siNA solution is diluted with an equal volume of Citrate buffer using a dual head peristaltic pump, Master Flex Peristaltic Pump, Model 7520-40 that is set up with equal lengths of tubing and a Tee connection and a flow rate of 360 mL/minute.

6. Ultrafiltration and Concentration

The ultrafiltration process is a timed process and the flow rates must be monitored carefully. This is a two step process; the first is a concentration step taking the diluted material from 32 liters to 3600 mLs and to a concentration of approximately 2 mg/mL.

In the first step, a Flexstand with a ultrafiltration membrane GE PN UFP-100-C-35A installed is attached to the quatroflow pump. 200 mL of WFI is added to the reservoir followed by 3 liters of 0.5 N sodium hydroxide which is then flushed through the retentate to waste. This process is repeated three times. Then 3 L WFI are flushed through the system twice followed by 3 L of citrate buffer. The pump is then drained.

The diluted LNP solution is placed into the reservoir to the 4 liter mark. The pump is turned on and the pump speed adjusted so the permeate flow rate is 300 mL/min. and the liquid level is constant at 4 L in the reservoir. The pump is stopped when all the diluted LNP solution has been transferred to the reservoir. The diluted LNP solution is concentrated to 3600 mL in 240 minutes by adjusting the pump speed as necessary.

The second step is a diafiltration step exchanging the ethanol citrate buffer to phosphate buffered saline. The diafiltration step takes 3 hours and again the flow rates must be carefully monitored. During this step, the ethanol concentration is monitored by head space GC. After 3 hours (20 diafiltration volumes), a second concentration is undertaken to concentrate the solution to approximately 6 mg/mL or a volume of 1.2 liters. This material is collected into a depyrogenated glass vessel. The system is rinsed with 400 mL of PBS at high flow rate and the permeate line closed. This material is collected and added to the first collection. The expected concentration at this point is 4.5 mg/mL. The concentration and volume are determined.

The feed tubing of the peristaltic pump is placed into a container containing 72 L of PBS (0.05 μm filtered) and the flow rate is adjusted initially to maintain a constant volume of 3600 mL in the reservoir and then increased to 400 mL/min. The LNP solution is diafiltered with PBS (20 volumes) for 180 minutes.

The LNP solution is concentrated to the 1.2 liter mark and collected into a depyrogenated 2 L graduated cylinder. 400 mL of PBS are added to the reservoir and the pump is recirculated for 2 minutes. The rinse is collected and added to the collected LNP solution in the graduated cylinder.

The obtained LNPs are characterized in terms of particle size, Zeta potential, alcohol content, total lipid content, nucleic acid encapsulated, and total nucleic acid concentration.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

TABLE 7

| FCeR1α Accession Numbers |
| --- |
| NM_002001 - SEQ ID NO: 140<br>*Homo sapiens* Fc fragment of IgE, high affinity I, receptor for; alpha polypeptide (FCER1A), mRNA<br>gi\|31317229\|ref\|NM_002001.2\|[31317229]<br>NM_010184<br>*Mus musculus* Fc receptor, IgE, high affinity I, alpha polypeptide (Fcer1a), mRNA |

TABLE 7-continued

FCεR1α Accession Numbers gi|6753827|ref|NM_010184.1|[6753827]
NM_012724
*Rattus norvegicus* Fc fragment of IgE, high affinity I, receptor for; alpha polypeptide (Fcer1a), mRNA
gi|119709835|ref|NM_02724.4|[119709835]

TABLE 8

Non-limiting examples of Stabilization Chemistries for chemically modified siNA constructs

| Chemistry | pyrimidine | Purine | cap | p = S | Strand |
|---|---|---|---|---|---|
| "Stab 00" | Ribo | Ribo | TT at 3'-ends | | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S/AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | | Usually S |
| "Stab 13" | 2'-fluoro | LNA | | 1 at 3'-end | Usually AS |
| "Stab 14" | 2'-fluoro | 2'-deoxy | | 2 at 5'-end 1 at 3'-end | Usually AS |
| "Stab 15" | 2'-deoxy | 2'-deoxy | | 2 at 5'-end 1 at 3'-end | Usually AS |
| "Stab 16" | Ribo | 2'-O-Methyl | 5' and 3'-ends | | Usually S |
| "Stab 17" | 2'-O-Methyl | 2'-O-Methyl | 5' and 3'-ends | | Usually S |
| "Stab 18" | 2'-fluoro | 2'-O-Methyl | 5' and 3'-ends | | Usually S |
| "Stab 19" | 2'-fluoro | 2'-O-Methyl | 3'-end | | S/AS |
| "Stab 20" | 2'-fluoro | 2'-deoxy | 3'-end | | Usually AS |
| "Stab 21" | 2'-fluoro | Ribo | 3'-end | | Usually AS |
| "Stab 22" | Ribo | Ribo | 3'-end | | Usually AS |
| "Stab 23" | 2'-fluoro* | 2'-deoxy* | 5' and 3'-ends | | Usually S |
| "Stab 24" | 2'-fluoro* | 2'-O-Methyl* | — | 1 at 3'-end | S/AS |
| "Stab 25" | 2'-fluoro* | 2'-O-Methyl* | — | 1 at 3'-end | S/AS |
| "Stab 26" | 2'-fluoro* | 2'-O-Methyl* | — | | S/AS |
| "Stab 27" | 2'-fluoro* | 2'-O-Methyl* | 3'-end | | S/AS |
| "Stab 28" | 2'-fluoro* | 2'-O-Methyl* | 3'-end | | S/AS |
| "Stab 29" | 2'-fluoro* | 2'-O-Methyl* | | 1 at 3'-end | S/AS |
| "Stab 30" | 2'-fluoro* | 2'-O-Methyl* | | | S/AS |
| "Stab 31" | 2'-fluoro* | 2'-O-Methyl* | 3'-end | | S/AS |
| "Stab 32" | 2'-fluoro | 2'-O-Methyl | | | S/AS |
| "Stab 33" | 2'-fluoro | 2'-deoxy* | 5' and 3'-ends | — | Usually S |
| "Stab 34" | 2'-fluoro | 2'-O-Methyl* | 5' and 3'-ends | | Usually S |
| "Stab 35" | 2'-fluoro*† | 2'-O-Methyl*† | | | Usually AS |
| "Stab 36" | 2'-fluoro*† | 2'-O-Methyl*† | | | Usually AS |
| "Stab 3F" | 2'-OCF3 | Ribo | — | 4 at 5'-end 4 at 3'-end | Usually S |
| "Stab 4F" | 2'-OCF3 | Ribo | 5' and 3'-ends | — | Usually S |
| "Stab 5F" | 2'-OCF3 | Ribo | — | 1 at 3'-end | Usually AS |
| "Stab 7F" | 2'-OCF3 | 2'-deoxy | 5' and 3'-ends | — | Usually S |
| "Stab 8F" | 2'-OCF3 | 2'-O-Methyl | — | 1 at 3'-end | S/AS |
| "Stab 11F" | 2'-OCF3 | 2'-deoxy | — | 1 at 3'-end | Usually AS |
| "Stab 12F" | 2'-OCF3 | LNA | 5' and 3'-ends | | Usually S |
| "Stab 13F" | 2'-OCF3 | LNA | | 1 at 3'-end | Usually AS |
| "Stab 14F" | 2'-OCF3 | 2'-deoxy | | 2 at 5'-end 1 at 3'-end | Usually AS |
| "Stab 15F" | 2'-OCF3 | 2'-deoxy | | 2 at 5'-end 1 at 3'-end | Usually AS |
| "Stab 18F" | 2'-OCF3 | 2'-O-Methyl | 5' and 3'-ends | | Usually S |
| "Stab 19F" | 2'-OCF3 | 2'-O-Methyl | 3'-end | | S/AS |
| "Stab 20F" | 2'-OCF3 | 2'-deoxy | 3'-end | | Usually AS |
| "Stab 21F" | 2'-OCF3 | Ribo | 3'-end | | Usually AS |
| "Stab 23F" | 2'-OCF3* | 2'-deoxy* | 5' and 3'-ends | | Usually S |
| "Stab 24F" | 2'-OCF3* | 2'-O-Methyl* | — | 1 at 3'-end | S/AS |
| "Stab 25F" | 2'-OCF3* | 2'-O-Methyl* | — | 1 at 3'-end | S/AS |
| "Stab 26F" | 2'-OCF3* | 2'-O-Methyl* | — | | S/AS |
| "Stab 27F" | 2'-OCF3* | 2'-O-Methyl* | 3'-end | | S/AS |
| "Stab 28F" | 2'-OCF3* | 2'-O-Methyl* | 3'-end | | S/AS |
| "Stab 29F" | 2'-OCF3* | 2'-O-Methyl* | | 1 at 3'-end | S/AS |

TABLE 8-continued

Non-limiting examples of Stabilization Chemistries for chemically modified siNA constructs

| Chemistry | pyrimidine | Purine | cap | p = S | Strand |
|---|---|---|---|---|---|
| "Stab 30F" | 2'-OCF3* | 2'-O-Methyl* | | | S/AS |
| "Stab 31F" | 2'-OCF3* | 2'-O-Methyl* | 3'-end | | S/AS |
| "Stab 32F" | 2'-OCF3 | 2'-O-Methyl | | | S/AS |
| "Stab 33F" | 2'-OCF3 | 2'-deoxy* | 5' and 3'-ends | | Usually S |
| "Stab 34F" | 2'-OCF3 | 2'-O-Methyl* | 5' and 3'-ends | — | Usually S |
| "Stab 35F" | 2'-OCF3*† | 2'-O-Methyl*† | | | Usually AS |
| "Stab 36F" | 2'-OCF3*† | 2'-O-Methyl*† | | | Usually AS |

CAP = any terminal cap, see for example FIG. 5.
All Stab 00-34 chemistries can comprise 3'-terminal thymidine (TT) residues
All Stab 00-34 chemistries typically comprise about 21 nucleotides, but can vary as described herein.
All Stab 00-36 chemistries can also include a single ribonucleotide in the sense or passenger strand at the 11th base paired position of the double-stranded nucleic acid duplex as determined from the 5'-end of the antisense or guide strand (see FIG. 4C)
S = sense strand
AS = antisense strand
*Stab 23 has a single ribonucleotide adjacent to 3'-CAP
*Stab 24 and Stab 28 have a single ribonucleotide at 5'-terminus
*Stab 25, Stab 26, Stab 27, Stab 35 and Stab 36 have three ribonucleotides at 5'-terminus
*Stab 29, Stab 30, Stab 31, Stab 33, and Stab 34 any purine at first three nucleotide positions from 5'-terminus are ribonucleotides
p = phosphorothioate linkage
†Stab 35 has 2'-O-methyl U at 3'-overhangs and three ribonucleotides at 5'-terminus
†Stab 36 has 2'-O-methyl overhangs that are complementary to the target sequence (naturally occurring overhangs) and three ribonucleotides at 5'-terminus

TABLE 9

A. 2.5 µmol Synthesis Cycle ABI 394 Instrument

| Reagent | Equivalents | Amount | Wait Time* DNA | Wait Time* 2'-O-methyl | Wait Time*RNA |
|---|---|---|---|---|---|
| Phosphoramidites | 6.5 | 163 µL | 45 sec | 2.5 min | 7.5 min |
| S-Ethyl Tetrazole | 23.8 | 238 µL | 45 sec | 2.5 min | 7.5 min |
| Acetic Anhydride | 100 | 233 µL | 5 sec | 5 sec | 5 sec |
| N-Methyl Imidazole | 186 | 233 µL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 µL | 100 sec | 300 sec | 300 sec |
| Acetonitrile | NA | 6.67 mL | NA | NA | NA |

B. 0.2 µmol Synthesis Cycle ABI 394 Instrument

| Reagent | Equivalents | Amount | Wait Time* DNA | Wait Time* 2'-O-methyl | Wait Time*RNA |
|---|---|---|---|---|---|
| Phosphoramidites | 15 | 31 µL | 45 sec | 233 sec | 465 sec |
| S-Ethyl Tetrazole | 38.7 | 31 µL | 45 sec | 233 min | 465 sec |
| Acetic Anhydride | 655 | 124 µL | 5 sec | 5 sec | 5 sec |
| N-Methyl Imidazole | 1245 | 124 µL | 5 sec | 5 sec | 5 sec |
| TCA | 700 | 732 µL | 10 sec | 10 sec | 10 sec |
| Iodine | 20.6 | 244 µL | 15 sec | 15 sec | 15 sec |
| Beaucage | 7.7 | 232 µL | 100 sec | 300 sec | 300 sec |
| Acetonitrile | NA | 2.64 mL | NA | NA | NA |

C. 0.2 µmol Synthesis Cycle 96 well Instrument

| Reagent | Equivalents: DNA/2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 µL | 60 sec | 180 sec | 360 sec |

TABLE 9-continued

| | | | | | |
|---|---|---|---|---|---|
| S-Ethyl Tetrazole | 70/105/210 | 40/60/120 µL | 60 sec | 180 min | 360 sec |
| Acetic Anhydride | 265/265/265 | 50/50/50 µL | 10 sec | 10 sec | 10 sec |
| N-Methyl Imidazole | 502/502/502 | 50/50/50 µL | 10 sec | 10 sec | 10 sec |
| TCA | 238/475/475 | 250/500/500 µL | 15 sec | 15 sec | 15 sec |
| Iodine | 6.8/6.8/6.8 | 80/80/80 µL | 30 sec | 30 sec | 30 sec |
| Beaucage | 34/51/51 | 80/120/120 | 100 sec | 200 sec | 200 sec |
| Acetonitrile | NA | 1150/1150/1150 µL | NA | NA | NA |

Wait time does not include contact time during delivery.
Tandem synthesis utilizes double coupling of linker molecule

TABLE 10

Lipid Nanoparticle (LNP) Formulations

| Formulation # | Composition | Mole Ratio |
|---|---|---|
| L051 | CLinDMA/DSPC/Chol/PEG-n-DMG | 48/40/10/2 |
| L053 | DMOBA/DSPC/Chol/PEG-n-DMG | 30/20/48/2 |
| L054 | DMOBA/DSPC/Chol/PEG-n-DMG | 50/20/28/2 |
| L069 | CLinDMA/DSPC/Cholesterol/PEG-Cholesterol | 48/40/10/2 |
| L073 | pCLinDMA or CLin DMA/DMOBA/DSPC/Chol/PEG-n-DMG | 25/25/20/28/2 |
| L077 | eCLinDMA/DSPC/Cholesterol/2KPEG-Chol | 48/40/10/2 |
| L080 | eCLinDMA/DSPC/Cholesterol/2KPEG-DMG | 48/40/10/2 |
| L082 | pCLinDMA/DSPC/Cholesterol/2KPEG-DMG | 48/40/10/2 |
| L083 | pCLinDMA/DSPC/Cholesterol/2KPEG-Chol | 48/40/10/2 |
| L086 | CLinDMA/DSPC/Cholesterol/2KPEG-DMG/Linoleyl alcohol | 43/38/10/2/7 |
| L061 | DMLBA/Cholesterol/2KPEG-DMG | 52/45/3 |
| L060 | DMOBA/Cholesterol/2KPEG-DMG N/P ratio of 5 | 52/45/3 |
| L097 | DMLBA/DSPC/Cholesterol/2KPEG-DMG | 50/20/28/2 |
| L098 | DMOBA/Cholesterol/2KPEG-DMG, N/P ratio of 3 | 52/45/3 |
| L099 | DMOBA/Cholesterol/2KPEG-DMG, N/P ratio of 4 | 52/45/3 |
| L100 | DMOBA/DOBA/3% PEG-DMG, N/P ratio of 3 | 52/45/3 |
| L101 | DMOBA/Cholesterol/2KPEG-Cholesterol | 52/45/3 |
| L102 | DMOBA/Cholesterol/2KPEG-Cholesterol, N/P ratio of 5 | 52/45/3 |
| L103 | DMLBA/Cholesterol/2KPEG-Cholesterol | 52/45/3 |
| L104 | CLinDMA/DSPC/Cholesterol/2KPEG-cholesterol/Linoleyl alcohol | 43/38/10/2/7 |
| L105 | DMOBA/Cholesterol/2KPEG-Chol, N/P ratio of 2 | 52/45/3 |
| L106 | DMOBA/Cholesterol/2KPEG-Chol, N/P ratio of 3 | 67/30/3 |
| L107 | DMOBA/Cholesterol/2KPEG-Chol, N/P ratio of 1.5 | 52/45/3 |
| L108 | DMOBA/Cholesterol/2KPEG-Chol, N/P ratio of 2 | 67/30/3 |
| L109 | DMOBA/DSPC/Cholesterol/2KPEG-Chol, N/P ratio of 2 | 50/20/28/2 |
| L110 | DMOBA/Cholesterol/2KPEG-DMG, N/P ratio of 1.5 | 52/45/3 |
| L111 | DMOBA/Cholesterol/2KPEG-DMG, N/P ratio of 1.5 | 67/30/3 |
| L112 | DMLBA/Cholesterol/2KPEG-DMG, N/P ratio of 1.5 | 52/45/3 |
| L113 | DMLBA/Cholesterol/2KPEG-DMG, N/P ratio of 1.5 | 67/30/3 |
| L114 | DMOBA/Cholesterol/2KPEG-DMG, N/P ratio of 2 | 52/45/3 |
| L115 | DMOBA/Cholesterol/2KPEG-DMG, N/P ratio of 2 | 67/30/3 |
| L116 | DMLBA/Cholesterol/2KPEG-DMG, N/P ratio of 2 | 52/45/3 |
| L117 | DMLBA/Cholesterol/2KPEG-DMG, N/P ratio of 2 | 52/45/3 |
| L118 | LinCDMA/DSPC/Cholesterol/2KPEG-DMG/Linoleyl alcohol, N/P ratio of 2.85 | 43/38/10/2/7 |
| L121 | 2-CLIM/DSPC/Cholesterol/2KPEG-DMG/, N/P ratio of 3 | 48/40/10/2 |
| L122 | 2-CLIM/Cholesterol/2KPEG-DMG/, N/P ratio of 3 | 68/30/2 |
| L123 | CLinDMA/DSPC/Cholesterol/2KPEG-DMG/Linoleyl alcohol, N/P ratio of 2.85 | 43/37/10/3/7 |
| L124 | CLinDMA/DSPC/Cholesterol/2KPEG-DMG/Linoleyl alcohol, N/P ratio of 2.85 | 43/36/10/4/7 |
| L130 | CLinDMA/DOPC/Chol/PEG-n-DMG, N/P ratio of 3 | 48/39/10/3 |
| L131 | DMLBA/Cholesterol/2KPEG-DMG, N/P ratio of 3 | 52/43/5 |
| L132 | DMOBA/Cholesterol/2KPEG-DMG, N/P ratio of 3 | 52/43/5 |
| L133 | CLinDMA/DOPC/Chol/PEG-n-DMG, N/P ratio of 3 | 48/40/10/2 |
| L134 | CLinDMA/DOPC/Chol/PEG-n-DMG, N/P ratio of 3 | 48/37/10/5 |
| L149 | COIM/DSPC/Cholesterol/2KPEG-DMG/, N/P ratio of 3 | 48/40/10/2 |
| L155 | CLinDMA/DOPC/Cholesterol/2KPEG-DMG/Linoleyl alcohol, N/P ratio of 2.85 | 43/38/10/2/7 |
| L156 | CLinDMA/DOPC/Cholesterol/2KPEG-DMG, N/P ratio of 2.85 | 45/43/10/2 |
| L162 | CLinDMA/DOPC/Cholesterol/2KPEG-DMG, N/P ratio of 2.5 | 45/43/10/2 |
| L163 | CLinDMA/DOPC/Cholesterol/2KPEG-DMG, N/P ratio of 2 | 45/43/10/2 |
| L164 | CLinDMA/DOPC/Cholesterol/2KPEG-DMG, N/P ratio of 2.25 | 45/43/10/2 |
| L165 | CLinDMA/DOPC/Cholesterol/2KPEG-DMG, N/P ratio of 2.25 | 40/43/15/2 |
| L166 | CLinDMA/DOPC/Cholesterol/2KPEG-DMG, N/P ratio of 2.5 | 40/43/15/2 |
| L167 | CLinDMA/DOPC/Cholesterol/2KPEG-DMG, N/P ratio of 2 | 40/43/15/2 |
| L174 | CLinDMA/DSPC/DOPC/Cholesterol/2KPEG-DMG/Linoleyl alcohol, N/P ratio of 2.85 | 43/9/27/10/4/7 |
| L175 | CLinDMA/DSPC/DOPC/Cholesterol/2KPEG-DMG/Linoleyl alcohol, N/P ratio of 2.85 | 43/27/9/10/4/7 |
| L176 | CLinDMA/DOPC/Cholesterol/2KPEG-DMG/Linoleyl alcohol, N/P ratio of 2.85 | 43/36/10/4/7 |
| L180 | CLinDMA/DOPC/Cholesterol/2KPEG-DMG/Linoleyl alcohol, N/P ratio of 2.25 | 43/36/10/4/7 |
| L181 | CLinDMA/DOPC/Cholesterol/2KPEG-DMG/Linoleyl alcohol, N/P ratio of 2 | 43/36/10/4/7 |
| L182 | CLinDMA/DOPC/Cholesterol/2KPEG-DMG, N/P ratio of 2.25 | 45/41/10/4 |

TABLE 10-continued

Lipid Nanoparticle (LNP) Formulations

| Formulation # | Composition | Mole Ratio |
|---|---|---|
| L197 | CODMA/DOPC/Cholesterol/2KPEG-DMG, N/P ratio of 2.85 | 43/36/10/4/7 |
| L198 | CLinDMA/DOPC/Cholesterol/2KPEG-DMG/2KPEG-DSG/Linoleyl alcohol, N/P ratio of 2.85 | 43/34/10/4/2/7 |
| L199 | CLinDMA/DOPC/Cholesterol/2KPEG-DMG/Linoleyl alcohol, N/P ratio of 2.85 | 43/34/10/6/7 |
| L200 | CLinDMA/Cholesterol/2KPEG-DMG, N/P ratio of 3.0 | 50/46/4 |
| L201 | CLinDMA/Cholesterol/2KPEG-DMG, N/P ratio of 3.0 | 50/44/6 |
| L206 | CLinDMA/Cholesterol/2KPEG-DMG, N/P ratio of 3.0 | 40/56/4 |
| L207 | CLinDMA/Cholesterol/2KPEG-DMG, N/P ratio of 3.0 | 60/36/4 |
| L208 | CLinDMA/DOPC/Cholesterol/2KPEG-DMG, N/P ratio of 3.0 | 40/10/46/4 |
| L209 | CLinDMA/DOPC/Cholesterol/2KPEG-DMG, N/P ratio of 3.0 | 60/10/26/4 |

N/P ratio = Nitrogen:Phosphorous ratio between cationic lipid and nucleic acid

The 2KPEG utilized is PEG2000, a polydispersion which can typically vary from ~1500 to ~3000 Da (i.e., where PEG(n) is about 33 to about 67, or on average ~45).

TABLE 11

CLinDMA structure

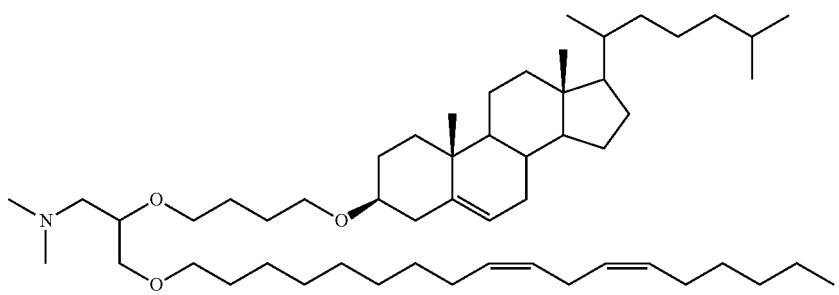 [SMILES: CCCCC/C=C\C/C=C\CCCCCCCCOCC(CN(C)C)OCCCCO[C@H]1CC[C@@]2(C)C(=CCC3C4CCC(C(C)CCCC(C)C)[C@@]4(C)CCC32)C1]

pCLinDMA structure

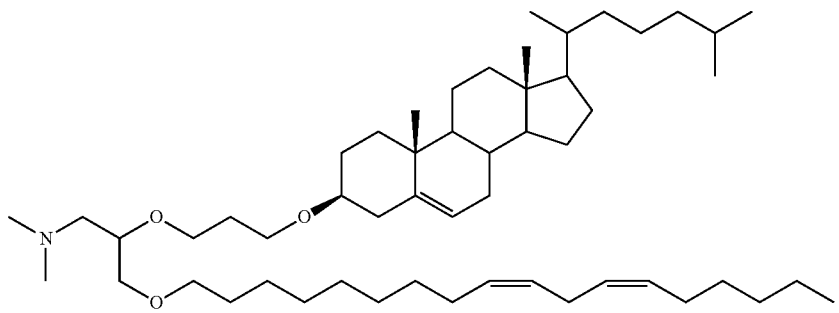 [SMILES: CCCCC/C=C\C/C=C\CCCCCCCCOCC(CN(C)C)OCCCO[C@H]1CC[C@@]2(C)C(=CCC3C4CCC(C(C)CCCC(C)C)[C@@]4(C)CCC32)C1]

eCLinDMA structure

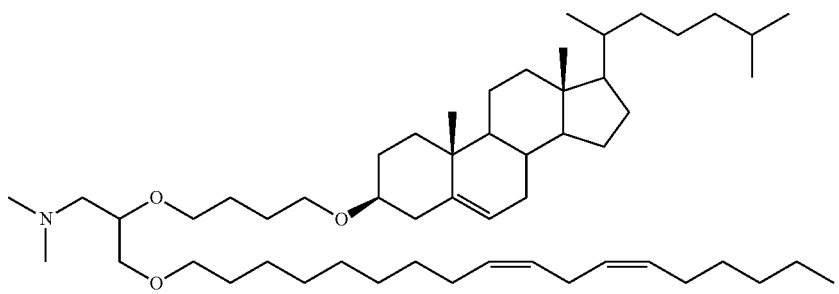 [SMILES: CCCCC/C=C\C/C=C\CCCCCCCCOCC(CN(C)C)OCCCCO[C@H]1CC[C@@]2(C)C(=CCC3C4CCC(C(C)CCCC(C)C)[C@@]4(C)CCC32)C1]

TABLE 11-continued
DEGCLinDMA structure
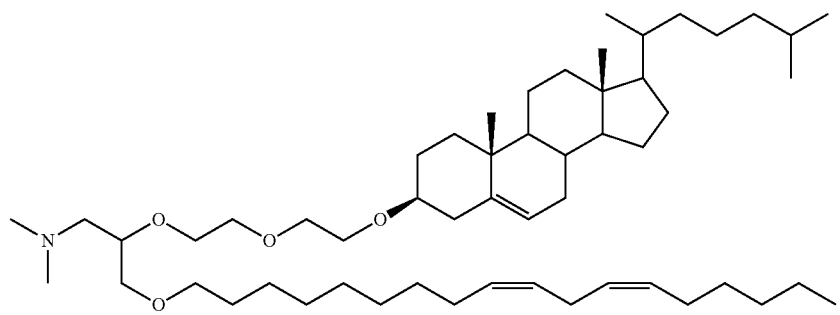 [SMILES: CCCCC/C=C\C/C=C\CCCCCCCCOCC(CN(C)C)OCCOCCO[C@H]1CC[C@@]2(C)C(=CCC3C4CCC(C(C)CCCC(C)C)[C@@]4(C)CCC32)C1]
PEG-n-DMG structure
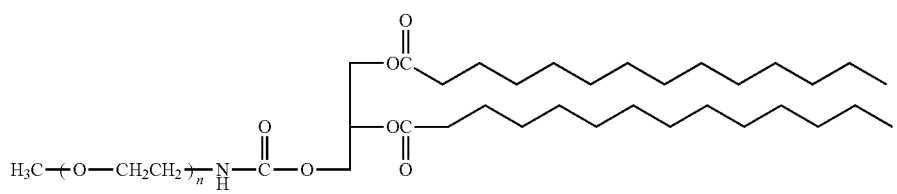
n = about 33 to 67, average = 45 for 2KPEG/PEG2000
DMOBA structure
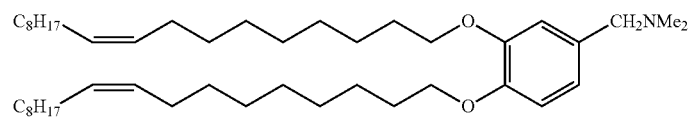
DMLBA structure
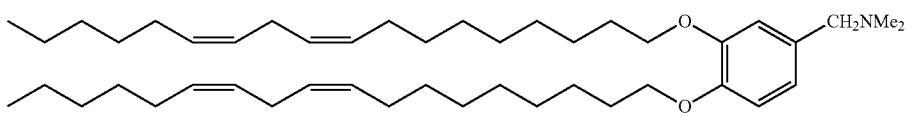
DOBA structure
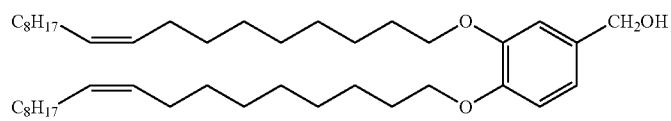
DSPC structure
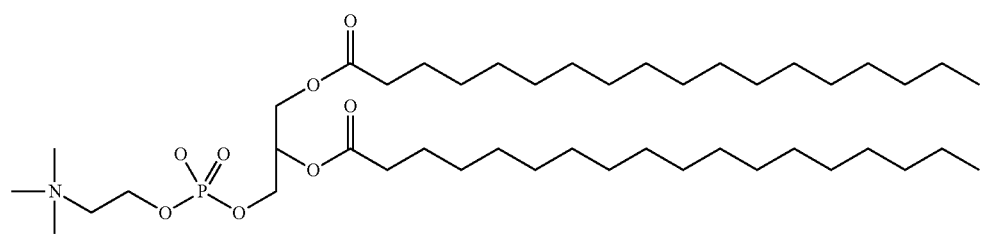

TABLE 11-continued
Cholesterol structure
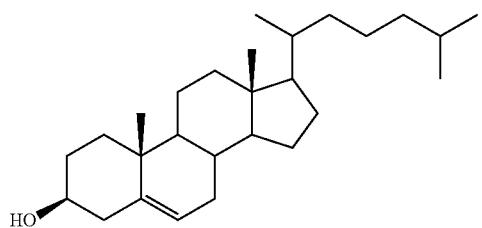 [SMILES: CC(C)CCCC(C)C1CCC2C3CC=C4C[C@@H](O)CC[C@]4(C)C3CC[C@]12C]
2KPEG-Cholesterol structure
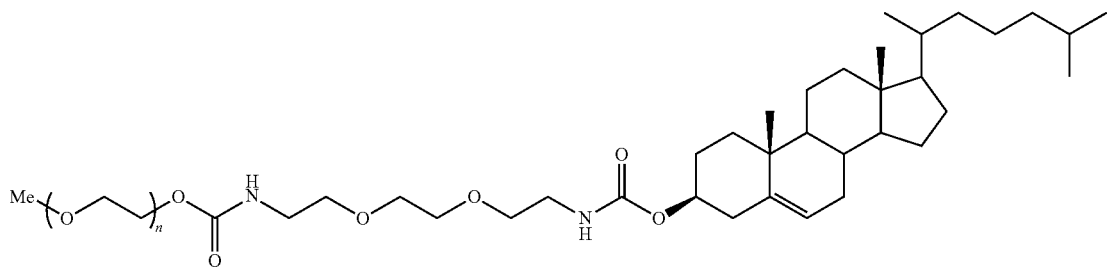
n = about 33 to 67, average = 45 for 2KPEG/PEG2000
2KPEG-DMG structure
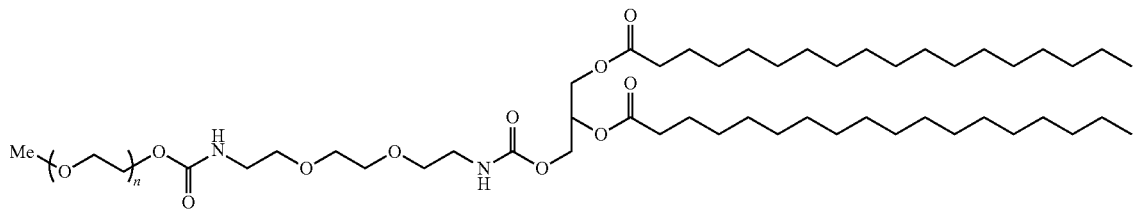
n = about 33 to 67, average = 45 for 2KPEG/PEG2000
COIM STRUCTURE
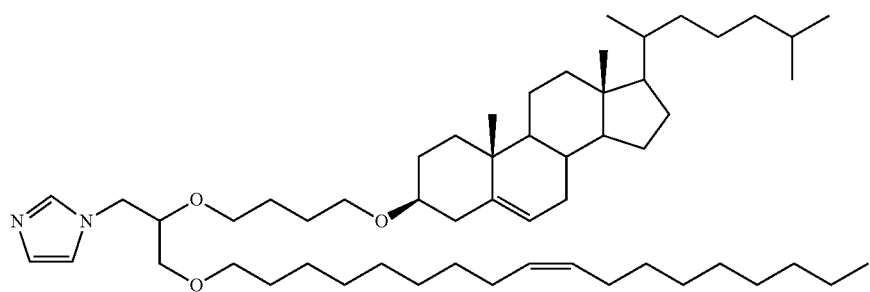 [SMILES: CCCCCCCC/C=C\CCCCCCCCOCC(Cn1ccnc1)OCCCCO[C@H]1CC[C@@]2(C)C(=CCC3C4CCC(C(C)CCCC(C)C)[C@@]4(C)CCC32)C1]

TABLE 11-continued

5-CLIM AND 2-CLIM STRUCTURE

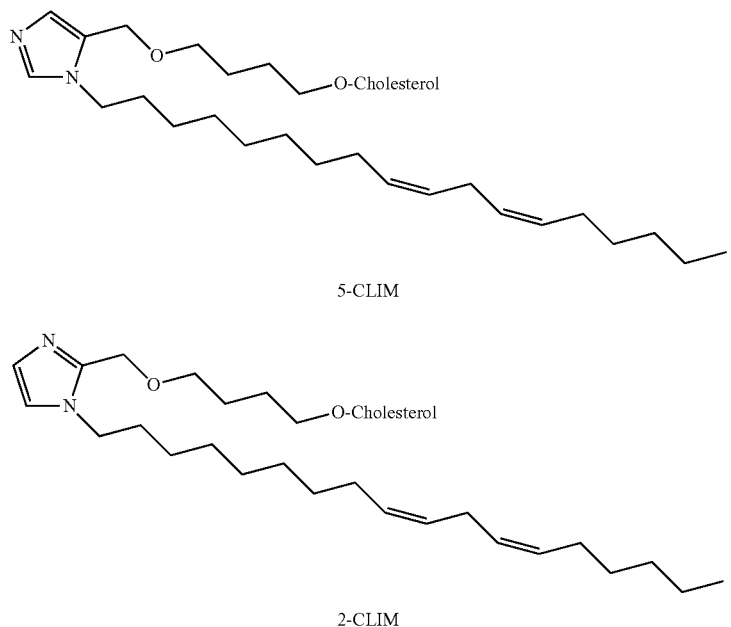

5-CLIM

2-CLIM

What we claim is:

1. A double-stranded short interfering nucleic acid (siNA) molecule wherein the siNA is:

wherein:
each B is an inverted abasic cap moiety;
c is 2'-deoxy-2'fluorocytidine;
u is 2'-deoxy-2'fluorouridine;
A is 2'-deoxyadenosine;
G is 2'-deoxyguanosine;
T is thymidine;
U is uridine;
A is 2'-O-methyl-adenosine;
G is 2'-O-methyl-guanosine;
U is 2'-O-methyl-uridine; and
the internucleotide linkages are chemically modified or unmodified.

2. The double-stranded short interfering nucleic acid (siNA) molecule according to claim 1, wherein the internucleotide linkages are unmodified.

3. A pharmaceutical composition comprising the double-stranded short interfering nucleic acid (siNA) of claim 1 in a pharmaceutically acceptable carrier or diluent.

4. A pharmaceutical composition comprising the double-stranded short interfering nucleic acid (siNA) molecule of claim 1 in an aerosol formulation.

* * * * *

SEQUENCE LISTING

<160> NUMBER OF SEQ ID NOS: 140

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
gcucaaggau uuauagaaa                                                 19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
cuugcaauau acauagaaa                                                 19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
ccauggaaua gaauauuua                                                 19

<210> SEQ ID NO 4
<211> LENGTH: 19

```
<212> TYPE: RNA
<213> ORGANISM: Artificial Sequence
<220> FEATURE:
<223> OTHER INFORMATION: Synthetic

<400> SEQUENCE: 4
gggaugugua caaggugau                                                  19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
cccucaacau uacuguaau                                                  19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
cgucugugcu caaggauuu                                                  19

<210> SEQ ID NO 7
<211> LENGTH: 19
<212> TYPE: RNA
<213> ORGANISM: Artificial Sequence
<220> FEATURE:
<223> OTHER INFORMATION: Synthetic

<400> SEQUENCE: 7
gcaugggccu auauuugaa                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
ucagcaccaa caaguuaau                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
acaggauuau uuaucucaa                                                  19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
ccuccaugga auagaauau                                                  19
```

```
<210> SEQ ID NO 11
<211> LENGTH: 19
<212> TYPE: RNA
<213> ORGANISM: Artificial Sequence
<220> FEATURE:
<223> OTHER INFORMATION: Synthetic

<400> SEQUENCE: 11
ccucaacauu acuguaaua                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
cccaaaaaca acugauaua                                                    19

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
caccgagcau gggccuaua                                                    19

<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
gguugaauaa augagagaa                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic

<400> SEQUENCE: 15
caguggagaa uacaaaugu                                                    19

<210> SEQ ID NO 16
<211> LENGTH: 19
<212> TYPE: RNA
<213> ORGANISM: Artificial Sequence
<220> FEATURE:
<223> OTHER INFORMATION: Synthetic

<400> SEQUENCE: 16
ugggaacaau uucuuugaa                                                    19

<210> SEQ ID NO 17
<211> LENGTH: 19
<212> TYPE: RNA
<213> ORGANISM: Artificial Sequence
<220> FEATURE:
<223> OTHER INFORMATION: Synthetic
```

-continued

<400> SEQUENCE: 17
ugguggugau ucuguuugc                                                    19

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
uuggugguga uucuguuug                                                    19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
agagugaacc uguguaccu                                                    19

<210> SEQ ID NO 20
<211> LENGTH: 19
<212> TYPE: RNA
<213> ORGANISM: Artificial Sequence
<220> FEATURE:
<223> OTHER INFORMATION: Synthetic

<400> SEQUENCE: 20
uggcugcucc uucaggccu                                                    19

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
uuguuggugg ugauucugu                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic

<400> SEQUENCE: 22
uauuuaaagg agagaaugu                                                    19

<210> SEQ ID NO 23
<211> LENGTH: 19
<212> TYPE: RNA
<213> ORGANISM: Artificial Sequence
<220> FEATURE:
<223> OTHER INFORMATION: Synthetic

<400> SEQUENCE: 23
gacccaccau ggauuagaa                                                    19

<210> SEQ ID NO 24
<211> LENGTH: 19

```
<212> TYPE: RNA
<213> ORGANISM: Artificial Sequence
<220> FEATURE:
<223> OTHER INFORMATION: Synthetic

<400> SEQUENCE: 24
ccaccaugga uuagaauau                                                    19

<210> SEQ ID NO 25
<211> LENGTH: 19
<212> TYPE: RNA
<213> ORGANISM: Artificial Sequence
<220> FEATURE:
<223> OTHER INFORMATION: Synthetic

<400> SEQUENCE: 25
ggaacaauca ccuucaaau                                                    19

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26
ugggaacaau caccuucaa                                                    19

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27
caguggaaaa uacauaugu                                                    19

<210> SEQ ID NO 28
<211> LENGTH: 19
<212> TYPE: RNA
<213> ORGANISM: Artificial Sequence
<220> FEATURE:
<223> OTHER INFORMATION: Synthetic

<400> SEQUENCE: 28
augggaacaa ucaccuuca                                                    19

<210> SEQ ID NO 29
<211> LENGTH: 19
<212> TYPE: RNA
<213> ORGANISM: Artificial Sequence
<220> FEATURE:
<223> OTHER INFORMATION: Synthetic

<400> SEQUENCE: 29
guggaaaaua cauauguca                                                    19

<210> SEQ ID NO 30
<211> LENGTH: 19
<212> TYPE: RNA
<213> ORGANISM: Artificial Sequence
<220> FEATURE:
<223> OTHER INFORMATION: Synthetic

<400> SEQUENCE: 30
gcuggaagaa cuggaaugu                                                    19
```

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
ccuguguacu ugaauguaa                                            19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
guggcaccua ccacugcaa                                            19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
gauacauaua ggaacuaau                                            19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
cucaugugau cccuagaaa                                            19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
aguggaaaau acauauguc                                            19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
ucagaagcaa ggauuguuu                                            19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
uaaauagcaa auacucaau                                                    19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
gccuagcacu gcuguucau                                                    19

<210> SEQ ID NO 39
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (5)..(9)
<223> OTHER INFORMATION: 2'-deoxy
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 39
gcucaaggau uuauagaaat t                                                 21

<210> SEQ ID NO 40
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)

```
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-O-methyl
<220> FEATURE:
<221> NAME/KEY: misc_feature
<222> LOCATION: (11)..(15)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 40
uuucuauaaa uccuugagcu u                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
```

```
<222> LOCATION: (11)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 41
cuugcaauau acauagaaat t                                              21

<210> SEQ ID NO 42
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
```

```
<222> LOCATION: (17)..(21)
<223> OTHER INFORMATION: 2'-O-methyl

<400> SEQUENCE: 42
uuucuaugua uauugcaagu u                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 43
ccauggaaua gaauauuuat t                                              21

<210> SEQ ID NO 44
<211> LENGTH: 21
<212> TYPE: RNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(21)
<223> OTHER INFORMATION: 2'-O-methyl

<400> SEQUENCE: 44
uaaauauucu auuccauggu u                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
```

```
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 45
gggaugugua caaggugaut t                                              21

<210> SEQ ID NO 46
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
```

```
<220> FEATURE:
<221> NAME/KEY: misc_feature
<222> LOCATION: (20)..(21)
<223> OTHER INFORMATION: 2'-O-methyl

<400> SEQUENCE: 46
aucaccuugu acacauccccu u                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 47
cccucaacau uacuguaaut t                                               21

<210> SEQ ID NO 48
```

```
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(21)
<223> OTHER INFORMATION: 2'-O-methyl

<400> SEQUENCE: 48
auuacaguaa uguugagggu u                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-deoxy
<220> FEATURE:
<221> NAME/KEY: misc_feature
<222> LOCATION: (3)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
```

```
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(11)
<223> OTHER INFORMATION: 2'-deoxy-2'-fluoro
<220> FEATURE:
<221> NAME/KEY: misc_feature
<222> LOCATION: (12)..(16)
<223> OTHER INFORMATION: 2'-deoxy
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 49
cgucugugcu caaggauuut t                                              21

<210> SEQ ID NO 50
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(8)
<223> OTHER INFORMATION: 2'-deoxy-2'-fluoro
<220> FEATURE:
<221> NAME/KEY: misc_feature
<222> LOCATION: (9)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 50
aaauccuuga gcacagacgu u                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(7)
<223> OTHER INFORMATION: 2'-deoxy
<220> FEATURE:
<221> NAME/KEY: misc_feature
<222> LOCATION: (8)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 51
gcaugggccu auauuugaat t                                              21

<210> SEQ ID NO 52
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
```

```
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(12)
<223> OTHER INFORMATION: 2'-O-methyl
<220> FEATURE:
<221> NAME/KEY: misc_feature
<222> LOCATION: (13)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 52
uucaaauaua ggcccaugcu u                                              21

<210> SEQ ID NO 53
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
```

```
<220> FEATURE:
<221> NAME/KEY: misc_feature
<222> LOCATION: (12)..(14)
<223> OTHER INFORMATION: 2'-deoxy
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 53
ucagcaccaa caaguuaaut t                                              21

<210> SEQ ID NO 54
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(21)
<223> OTHER INFORMATION: 2'-O-methyl

<400> SEQUENCE: 54
auuaacuugu uggugcugau u                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(6)
<223> OTHER INFORMATION: 2'-deoxy
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 55
acaggauuau uuaucucaat t                                          21

<210> SEQ ID NO 56
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
```

```
<223> OTHER INFORMATION: 2'-O-methyl
<220> FEATURE:
<221> NAME/KEY: misc_feature
<222> LOCATION: (14)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 56
uugagauaaa uaauccuguu u                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 57
```
ccuccaugga auagaauaut t                                              21

<210> SEQ ID NO 58
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(21)
<223> OTHER INFORMATION: 2'-O-methyl

<400> SEQUENCE: 58
auauucuauu ccauggaggu u                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:

```
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-deoxy
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 59
ccucaacauu acuguaauat t                                              21

<210> SEQ ID NO 60
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(21)
<223> OTHER INFORMATION: 2'-O-methyl
```

-continued

```
<400> SEQUENCE: 60
uauuacagua auguugaggu u                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-deoxy
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 61
cccaaaaaca acugauauat t                                              21

<210> SEQ ID NO 62
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
```

-continued

```
<220> FEATURE:
<221> NAME/KEY: misc_feature
<222> LOCATION: (5)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(16)
<223> OTHER INFORMATION: 2'-deoxy-2'-fluoro
<220> FEATURE:
<221> NAME/KEY: misc_feature
<222> LOCATION: (17)..(21)
<223> OTHER INFORMATION: 2'-O-methyl

<400> SEQUENCE: 62
uauaucaguu guuuugggu u                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-deoxy
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy
<220> FEATURE:
<221> NAME/KEY: misc_feature
<222> LOCATION: (14)..(16)
```

```
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 63
caccgagcau gggccuauau t                                            21

<210> SEQ ID NO 64
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
<222> LOCATION: (7)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 64
uauaggccca ugcucggugu u                                            21

<210> SEQ ID NO 65
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
```

-continued

```
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 65
gguugaauaa augagagaat t                                           21

<210> SEQ ID NO 66
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
```

<222> LOCATION: (20)..(21)
<223> OTHER INFORMATION: 2'-O-methyl

<400> SEQUENCE: 66
uucucucauu uauucaaccu u                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(3)
<223> OTHER INFORMATION: 2'-deoxy
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 67
caguggagaa uacaaaugut t                                              21

<210> SEQ ID NO 68
<211> LENGTH: 21
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 68
acauuuguau ucuccacugu u                                      21

<210> SEQ ID NO 69
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-deoxy
<220> FEATURE:
<221> NAME/KEY: misc_feature
<222> LOCATION: (10)..(16)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy
```

```
<220> FEATURE:
<221> NAME/KEY: misc_feature
<222> LOCATION: (21)..(21)
<223> OTHER INFORMATION: inverted abasic cap

<400> SEQUENCE: 69
ugggaacaau ucuuugaat t                                                    21

<210> SEQ ID NO 70
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 70
uucaaagaaa uuguuccau u                                                    21

<210> SEQ ID NO 71
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(3)
<223> OTHER INFORMATION: 2'-deoxy
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
```

```
<223> OTHER INFORMATION: 2'-deoxy
<220> FEATURE:
<221> NAME/KEY: misc_feature
<222> LOCATION: (10)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 71
ugguggugau ucuguuugct t                                       21

<210> SEQ ID NO 72
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 72
gcaaacagaa ucaccaccau u                                       21

<210> SEQ ID NO 73
```

```
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-deoxy
<220> FEATURE:
<221> NAME/KEY: misc_feature
<222> LOCATION: (11)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 73
uuggugguga uucuguuugt t                                              21

<210> SEQ ID NO 74
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
```

```
<222> LOCATION: (6)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(21)
<223> OTHER INFORMATION: 2'-O-methyl

<400> SEQUENCE: 74
caaacagaau caccaccaau u                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(8)
<223> OTHER INFORMATION: 2'-deoxy
<220> FEATURE:
<221> NAME/KEY: misc_feature
<222> LOCATION: (9)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
```

```
<221> NAME/KEY: misc_feature
<222> LOCATION: (16)..(16)
<223> OTHER INFORMATION: 2'-deoxy
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 75
agagugaacc uguguaccut t                                         21

<210> SEQ ID NO 76
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(11)
<223> OTHER INFORMATION: 2'-O-methyl
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 76
agguacacag guucacucuu u                                         21

<210> SEQ ID NO 77
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
```

```
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(3)
<223> OTHER INFORMATION: 2'-deoxy
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(13)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 77
uggcugcucc uucaggccut t                                              21

<210> SEQ ID NO 78
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-deoxy-2'-fluoro
<220> FEATURE:
<221> NAME/KEY: misc_feature
<222> LOCATION: (7)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: 2'-O-methyl
<220> FEATURE:
<221> NAME/KEY: misc_feature
<222> LOCATION: (17)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 78
aggccugaag gagcagccau u                                              21

<210> SEQ ID NO 79
<211> LENGTH: 21
```

-continued

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-deoxy
<220> FEATURE:
<221> NAME/KEY: misc_feature
<222> LOCATION: (14)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 79
uuguuggugg ugauucugut t                                              21

<210> SEQ ID NO 80
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
<222> LOCATION: (7)..(7)
```

```
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(21)
<223> OTHER INFORMATION: 2'-O-methyl

<400> SEQUENCE: 80
acagaaucac caccaacaau u                                            21

<210> SEQ ID NO 81
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-deoxy
<220> FEATURE:
<221> NAME/KEY: misc_feature
<222> LOCATION: (3)..(5)
<223> OTHER INFORMATION: 2'-deoxy-2'-fluoro
<220> FEATURE:
<221> NAME/KEY: misc_feature
<222> LOCATION: (6)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
```

```
<222> LOCATION: (21)..(21)
<223> OTHER INFORMATION: inverted abasic cap

<400> SEQUENCE: 81
uauuuaaagg agagaaugut t                                              21

<210> SEQ ID NO 82
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(14)
<223> OTHER INFORMATION: 2'-deoxy-2'-fluoro
<220> FEATURE:
<221> NAME/KEY: misc_feature
<222> LOCATION: (15)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 82
acauucucuc cuuuaaauau u                                              21

<210> SEQ ID NO 83
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy
<220> FEATURE:
<221> NAME/KEY: misc_feature
<222> LOCATION: (3)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy
<220> FEATURE:
```

```
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 83
gacccaccau ggauuagaat t                                              21

<210> SEQ ID NO 84
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 84
uucuaaucca uggugggucu u                                              21

<210> SEQ ID NO 85
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
```

```
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 85
ccaccaugga uuagaauaut t                                      21

<210> SEQ ID NO 86
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
```

```
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(21)
<223> OTHER INFORMATION: 2'-O-methyl

<400> SEQUENCE: 86
auauucuaau ccaugguggu u                                              21

<210> SEQ ID NO 87
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (11)..(15)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 87
ggaacaauca ccuucaaaut t                                              21

<210> SEQ ID NO 88
```

```
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 88
auuugaaggu gauuguuccu u                                                21

<210> SEQ ID NO 89
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-deoxy
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
```

```
<222> LOCATION: (12)..(12)
<223> OTHER INFORMATION: 2'-deoxy
<220> FEATURE:
<221> NAME/KEY: misc_feature
<222> LOCATION: (13)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 89
ugggaacaau caccuucaat t                                                  21

<210> SEQ ID NO 90
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 90
uugaagguga uuguuccau u                                                   21

<210> SEQ ID NO 91
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
```

```
<221> NAME/KEY: misc_feature
<222> LOCATION: (2)..(3)
<223> OTHER INFORMATION: 2'-deoxy
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 91
caguggaaaa uacauaugut t                                           21

<210> SEQ ID NO 92
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
```

-continued

```
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 92
acauauguau uuuccacugu u                                              21

<210> SEQ ID NO 93
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
```

```
<220> FEATURE:
<221> NAME/KEY: misc_feature
<222> LOCATION: (21)..(21)
<223> OTHER INFORMATION: inverted abasic cap

<400> SEQUENCE: 93
augggaacaa ucaccuucat t                                              21

<210> SEQ ID NO 94
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 94
ugaaggugau uguucccauu u                                              21

<210> SEQ ID NO 95
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
```

```
<223> OTHER INFORMATION: 2'-deoxy-2'-fluoro
<220> FEATURE:
<221> NAME/KEY: misc_feature
<222> LOCATION: (3)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy
<220> FEATURE:
<221> NAME/KEY: misc_feature
<222> LOCATION: (17)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 95
guggaaaaua cauaugucat t                                         21

<210> SEQ ID NO 96
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
```

```
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 96
ugacauaugu auuuuccacu u                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (4)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
```

```
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 97
gcuggaagaa cuggaaugut t                                              21

<210> SEQ ID NO 98
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 98
acauuccagu ucuuccagcu u                                              21

<210> SEQ ID NO 99
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
```

```
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(11)
<223> OTHER INFORMATION: 2'-deoxy-2'-fluoro
<220> FEATURE:
<221> NAME/KEY: misc_feature
<222> LOCATION: (12)..(14)
<223> OTHER INFORMATION: 2'-deoxy
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 99
ccuguguacu ugaauguaat t                                      21

<210> SEQ ID NO 100
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(8)
<223> OTHER INFORMATION: 2'-deoxy-2'-fluoro
<220> FEATURE:
<221> NAME/KEY: misc_feature
<222> LOCATION: (9)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
```

```
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(21)
<223> OTHER INFORMATION: 2'-O-methyl

<400> SEQUENCE: 100
uuacauucaa guacacaggu u                                              21

<210> SEQ ID NO 101
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy
```

```
<220> FEATURE:
<221> NAME/KEY: misc_feature
<222> LOCATION: (21)..(21)
<223> OTHER INFORMATION: inverted abasic cap

<400> SEQUENCE: 101
guggcaccua ccacugcaat t                                              21

<210> SEQ ID NO 102
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 102
uugcaguggu aggugccacu u                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
```

```
            described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(14)
<223> OTHER INFORMATION: 2'-deoxy
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 103
gauacauaua ggaacuaaut t                                        21

<210> SEQ ID NO 104
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(10)
<223> OTHER INFORMATION: 2'-deoxy-2'-fluoro
<220> FEATURE:
<221> NAME/KEY: misc_feature
<222> LOCATION: (11)..(11)
```

-continued

```
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 104
auuaguuccu auauguaucu u                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-deoxy
<220> FEATURE:
<221> NAME/KEY: misc_feature
```

```
<222> LOCATION: (10)..(14)
<223> OTHER INFORMATION: 2'-deoxy-2'-fluoro
<220> FEATURE:
<221> NAME/KEY: misc_feature
<222> LOCATION: (15)..(19)
<223> OTHER INFORMATION: 2'-deoxy
<220> FEATURE:
<221> NAME/KEY: misc_feature
<222> LOCATION: (21)..(21)
<223> OTHER INFORMATION: inverted abasic cap

<400> SEQUENCE: 105
cacaugugau cccuagaaat t                                              21

<210> SEQ ID NO 106
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-deoxy-2'-fluoro
<220> FEATURE:
<221> NAME/KEY: misc_feature
<222> LOCATION: (6)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(21)
<223> OTHER INFORMATION: 2'-O-methyl

<400> SEQUENCE: 106
uuucuaggga ucacaugagu u                                              21

<210> SEQ ID NO 107
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy
<220> FEATURE:
```

```
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(9)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-deoxy
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 107
aguggaaaau acauauguct t                                      21

<210> SEQ ID NO 108
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
```

```
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 108
gacauaugua uuuuccacuu u                                              21

<210> SEQ ID NO 109
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-deoxy-2'-fluoro
<220> FEATURE:
<221> NAME/KEY: misc_feature
<222> LOCATION: (3)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(13)
<223> OTHER INFORMATION: 2'-deoxy
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 109
ucagaagcaa ggauuguuut t                                              21
```

```
<210> SEQ ID NO 110
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(17)
<223> OTHER INFORMATION: 2'-deoxy-2'-fluoro
<220> FEATURE:
<221> NAME/KEY: misc_feature
<222> LOCATION: (18)..(21)
<223> OTHER INFORMATION: 2'-O-methyl

<400> SEQUENCE: 110
aaacaauccu ugcuucugau u                                          21

<210> SEQ ID NO 111
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(4)
<223> OTHER INFORMATION: 2'-deoxy
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(11)
<223> OTHER INFORMATION: 2'-deoxy
<220> FEATURE:
<221> NAME/KEY: misc_feature
<222> LOCATION: (12)..(12)
```

```
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 111
uaaauagcaa auacucaaut t                                              21

<210> SEQ ID NO 112
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

<400> SEQUENCE: 112
auugaguauu ugcuauuuau u                                              21

<210> SEQ ID NO 113
<211> LENGTH: 21
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy
<220> FEATURE:
<221> NAME/KEY: misc_feature
<222> LOCATION: (2)..(4)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (21)..(21)
<223> OTHER INFORMATION: inverted abasic cap

<400> SEQUENCE: 113
gccuagcacu gcuguucaut t                                              21

<210> SEQ ID NO 114
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
```

```
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 114
augaacagca gugcuaggcu u                                              21

<210> SEQ ID NO 115
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modifed as
      described for this sequence
<220> FEATURE:
<221> NAME/KEY: misc_feature
<222> LOCATION: (1)..(1)
<223> OTHER INFORMATION: optional abasic, inverted abasic, inverted
      nucleotide or other terminal cap
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (21)..(21)
<223> OTHER INFORMATION: optional abasic, inverted abasic, inverted
      nucleotide or other terminal cap

<400> SEQUENCE: 115
nnnnnnnnnn nnnnnnnnnn n                                              21

<210> SEQ ID NO 116
<211> LENGTH: 21
<212> TYPE: DNA
<213> ORGANISM: Artificial Sequence
<220> FEATURE:
```

<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 116
nnnnnnnnnn nnnnnnnnn n                                              21

<210> SEQ ID NO 117
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide wherein any pyrimidine is
      2'-deoxy-2'-fluoro or 2'-O-trifluoromethyl and any purine is
      2'-O-methyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage

<400> SEQUENCE: 117
nnnnnnnnnn nnnnnnnnn n                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide wherein any pyrimidine is
      2'-deoxy-2'-fluoro or 2'-O-trifluoromethyl and any purine is
      2'-O-methyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 118
nnnnnnnnnn nnnnnnnnn n                                          21

<210> SEQ ID NO 119
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide wherein any pyrimidine is
      2'-deoxy-2'-fluoro or 2'-O-trifluoromethyl
<220> FEATURE:
<221> NAME/KEY: misc_feature
<222> LOCATION: (1)..(1)
<223> OTHER INFORMATION: optional abasic, inverted abasic, inverted
      nucleotide or other terminal cap
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (21)..(21)
<223> OTHER INFORMATION: optional abasic, inverted abasic, inverted
      nucleotide or other terminal cap

<400> SEQUENCE: 119
nnnnnnnnnn nnnnnnnnn n                                          21

<210> SEQ ID NO 120
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide wherein any pyrimidine is
      2'-deoxy-2'-fluoro or 2'-O-trifluoromethyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 120
nnnnnnnnnn nnnnnnnnn n                                          21

<210> SEQ ID NO 121
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide wherein any pyrimidine is
      2'-deoxy-2'-fluoro or 2'-O-trifluoromethyl and any purine is
      2'-deoxy
<220> FEATURE:
<221> NAME/KEY: misc_feature

```
<222> LOCATION: (1)..(1)
<223> OTHER INFORMATION: optional abasic, inverted abasic, inverted
      nucleotide or other terminal cap
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (21)..(21)
<223> OTHER INFORMATION: optional abasic, inverted abasic, inverted
      nucleotide or other terminal cap

<400> SEQUENCE: 121
nnnnnnnnnn nnnnnnnnn n                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide wherein any pyrimidine is
      2'-deoxy-2'-fluoro or 2'-O-trifluoromethyl and any purine is
      2'-deoxy
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 122
nnnnnnnnnn nnnnnnnnn n                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: optional abasic, inverted abasic, inverted
      nucleotide or other terminal cap
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (21)..(21)
<223> OTHER INFORMATION: optional abasic, inverted abasic, inverted
      nucleotide or other terminal cap

<400> SEQUENCE: 123
cuugcaauau acauagaaan n                                             21
```

```
<210> SEQ ID NO 124
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modifed as
      described for this sequence
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 124
uuucuaugua uauugcaagn n                                            21

<210> SEQ ID NO 125
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modifed as
      described for this sequence
<220> FEATURE:
<221> NAME/KEY: misc_feature
<222> LOCATION: (1)..(3)
<223> OTHER INFORMATION: 2'-deoxy-2'-fluoro or 2'-O-trifluoromethyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro or 2'-O-trifluoromethyl
<220> FEATURE:
<221> NAME/KEY: misc_feature
<222> LOCATION: (6)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro or 2'-O-trifluoromethyl
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro or 2'-O-trifluoromethyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro or 2'-O-trifluoromethyl
<220> FEATURE:
```

-continued

```
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro or 2'-O-trifluoromethyl
<220> FEATURE:
<221> NAME/KEY: misc_feature
<222> LOCATION: (15)..(19)
<223> OTHER INFORMATION: 2'-O-methyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage

<400> SEQUENCE: 125
cuugcaauau acauagaaan n                                              21

<210> SEQ ID NO 126
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(5)
<223> OTHER INFORMATION: 2'-deoxy-2'-fluoro or 2'-O-trifluoromethyl
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro or 2'-O-trifluoromethyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro or 2'-O-trifluoromethyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro or 2'-O-trifluoromethyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro or 2'-O-trifluoromethyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro or 2'-O-trifluoromethyl
```

```
<220> FEATURE:
<221> NAME/KEY: misc_feature
<222> LOCATION: (17)..(19)
<223> OTHER INFORMATION: 2'-O-methyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 126
uuucuaugua uauugcaagn n                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: optional abasic, inverted abasic, inverted
      nucleotide or other terminal cap
<220> FEATURE:
<221> NAME/KEY: misc_feature
<222> LOCATION: (1)..(3)
<223> OTHER INFORMATION: 2'-deoxy-2'-fluoro or 2'-O-trifluoromethyl
<220> FEATURE:
<221> NAME/KEY: misc_feature
<222> LOCATION: (5)..(5)
<223> OTHER INFORMATION: 2'-deoxy-2'-fluoro or 2'-O-trifluoromethyl
<220> FEATURE:
<221> NAME/KEY: misc_feature
<222> LOCATION: (8)..(8)
<223> OTHER INFORMATION: 2'-deoxy-2'-fluoro or 2'-O-trifluoromethyl
<220> FEATURE:
<221> NAME/KEY: misc_feature
<222> LOCATION: (10)..(10)
<223> OTHER INFORMATION: 2'-deoxy-2'-fluoro or 2'-O-trifluoromethyl
<220> FEATURE:
<221> NAME/KEY: misc_feature
<222> LOCATION: (12)..(12)
<223> OTHER INFORMATION: 2'-deoxy-2'-fluoro or 2'-O-trifluoromethyl
<220> FEATURE:
<221> NAME/KEY: misc_feature
<222> LOCATION: (14)..(14)
<223> OTHER INFORMATION: 2'-deoxy-2'-fluoro or 2'-O-trifluoromethyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (21)..(21)
<223> OTHER INFORMATION: optional abasic, inverted abasic, inverted
      nucleotide or other terminal cap

<400> SEQUENCE: 127
cuugcaauau acauagaaan n                                              21

<210> SEQ ID NO 128
```

```
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(5)
<223> OTHER INFORMATION: 2'-deoxy-2'-fluoro or 2'-O-trifluoromethyl
<220> FEATURE:
<221> NAME/KEY: misc_feature
<222> LOCATION: (7)..(7)
<223> OTHER INFORMATION: 2'-deoxy-2'-fluoro or 2'-O-trifluoromethyl
<220> FEATURE:
<221> NAME/KEY: misc_feature
<222> LOCATION: (9)..(9)
<223> OTHER INFORMATION: 2'-deoxy-2'-fluoro or 2'-O-trifluoromethyl
<220> FEATURE:
<221> NAME/KEY: misc_feature
<222> LOCATION: (11)..(11)
<223> OTHER INFORMATION: 2'-deoxy-2'-fluoro or 2'-O-trifluoromethyl
<220> FEATURE:
<221> NAME/KEY: misc_feature
<222> LOCATION: (13)..(14)
<223> OTHER INFORMATION: 2'-deoxy-2'-fluoro or 2'-O-trifluoromethyl
<220> FEATURE:
<221> NAME/KEY: misc_feature
<222> LOCATION: (16)..(16)
<223> OTHER INFORMATION: 2'-deoxy-2'-fluoro or 2'-O-trifluoromethyl
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 128
uuucuaugua uauugcaagn n                                         21

<210> SEQ ID NO 129
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: optional abasic, inverted abasic, inverted
      nucleotide or other terminal cap
<220> FEATURE:
<221> NAME/KEY: misc_feature
<222> LOCATION: (1)..(3)
<223> OTHER INFORMATION: 2'-deoxy-2'-fluoro or 2'-O-trifluoromethyl
<220> FEATURE:
<221> NAME/KEY: misc_feature
<222> LOCATION: (4)..(4)
<223> OTHER INFORMATION: 2'-deoxy
<220> FEATURE:
<221> NAME/KEY: misc_feature
```

```
<222> LOCATION: (5)..(5)
<223> OTHER INFORMATION: 2'-deoxy-2'-fluoro or 2'-O-trifluoromethyl
<220> FEATURE:
<221> NAME/KEY: misc_feature
<222> LOCATION: (6)..(7)
<223> OTHER INFORMATION: 2'-deoxy
<220> FEATURE:
<221> NAME/KEY: misc_feature
<222> LOCATION: (8)..(8)
<223> OTHER INFORMATION: 2'-deoxy-2'-fluoro or 2'-O-trifluoromethyl
<220> FEATURE:
<221> NAME/KEY: misc_feature
<222> LOCATION: (9)..(9)
<223> OTHER INFORMATION: 2'-deoxy
<220> FEATURE:
<221> NAME/KEY: misc_feature
<222> LOCATION: (10)..(10)
<223> OTHER INFORMATION: 2'-deoxy-2'-fluoro or 2'-O-trifluoromethyl
<220> FEATURE:
<221> NAME/KEY: misc_feature
<222> LOCATION: (11)..(11)
<223> OTHER INFORMATION: 2'-deoxy
<220> FEATURE:
<221> NAME/KEY: misc_feature
<222> LOCATION: (12)..(12)
<223> OTHER INFORMATION: 2'-deoxy-2'-fluoro or 2'-O-trifluoromethyl
<220> FEATURE:
<221> NAME/KEY: misc_feature
<222> LOCATION: (13)..(13)
<223> OTHER INFORMATION: 2'-deoxy
<220> FEATURE:
<221> NAME/KEY: misc_feature
<222> LOCATION: (14)..(14)
<223> OTHER INFORMATION: 2'-deoxy-2'-fluoro or 2'-O-trifluoromethyl
<220> FEATURE:
<221> NAME/KEY: misc_feature
<222> LOCATION: (15)..(19)
<223> OTHER INFORMATION: 2'-deoxy
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (21)..(21)
<223> OTHER INFORMATION: optional abasic, inverted abasic, inverted
      nucleotide or other terminal cap

<400> SEQUENCE: 129
cuugcaauau acauagaaan n                                          21

<210> SEQ ID NO 130
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(5)
<223> OTHER INFORMATION: 2'-deoxy-2'-fluoro or 2'-O-trifluoromethyl
<220> FEATURE:
<221> NAME/KEY: misc_feature
<222> LOCATION: (6)..(6)
<223> OTHER INFORMATION: 2'-deoxy
<220> FEATURE:
<221> NAME/KEY: misc_feature
<222> LOCATION: (7)..(7)
<223> OTHER INFORMATION: 2'-deoxy-2'-fluoro or 2'-O-trifluoromethyl
<220> FEATURE:
<221> NAME/KEY: misc_feature
<222> LOCATION: (8)..(8)
<223> OTHER INFORMATION: 2'-deoxy
```

```
<220> FEATURE:
<221> NAME/KEY: misc_feature
<222> LOCATION: (9)..(9)
<223> OTHER INFORMATION: 2'-deoxy-2'-fluoro or 2'-O-trifluoromethyl
<220> FEATURE:
<221> NAME/KEY: misc_feature
<222> LOCATION: (10)..(10)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro or 2'-O-trifluoromethyl
<220> FEATURE:
<221> NAME/KEY: misc_feature
<222> LOCATION: (12)..(12)
<223> OTHER INFORMATION: 2'-deoxy
<220> FEATURE:
<221> NAME/KEY: misc_feature
<222> LOCATION: (13)..(14)
<223> OTHER INFORMATION: 2'-deoxy-2'-fluoro or 2'-O-trifluoromethyl
<220> FEATURE:
<221> NAME/KEY: misc_feature
<222> LOCATION: (15)..(15)
<223> OTHER INFORMATION: 2'-deoxy
<220> FEATURE:
<221> NAME/KEY: misc_feature
<222> LOCATION: (16)..(16)
<223> OTHER INFORMATION: 2'-deoxy-2'-fluoro or 2'-O-trifluoromethyl
<220> FEATURE:
<221> NAME/KEY: misc_feature
<222> LOCATION: (17)..(19)
<223> OTHER INFORMATION: 2'-deoxy
<220> FEATURE:
<221> NAME/KEY: misc_feature
<222> LOCATION: (20)..(21)
<223> OTHER INFORMATION: n stands for any nucleotide
<220> FEATURE:
<221> NAME/KEY: misc_feature
<222> LOCATION: (20)..(21)
<223> OTHER INFORMATION: optional phosphorothioate linkage
<220> FEATURE:
<221> NAME/KEY: misc_feature
<222> LOCATION: (21)..(21)
<223> OTHER INFORMATION: optional 3'-3 attached terminal glyceryl moiety
      or optional abasic, inverted abasic, inverted nucleotide or other
      terminal cap

<400> SEQUENCE: 130
uuucuaugua uauugcaagn n                                                 21

<210> SEQ ID NO 131
<211> LENGTH: 19
<212> TYPE: RNA
<213> ORGANISM: Artificial Sequence
<220> FEATURE:
<223> OTHER INFORMATION: Synthetic

<400> SEQUENCE: 131
uuucuaugua uauugcaag                                                    19

<210> SEQ ID NO 132
<211> LENGTH: 19
<212> TYPE: RNA
<213> ORGANISM: Artificial Sequence
<220> FEATURE:
<223> OTHER INFORMATION: Synthetic

<400> SEQUENCE: 132
uaaauauucu auccaugg                                                     19

<210> SEQ ID NO 133
<211> LENGTH: 19
<212> TYPE: RNA
<213> ORGANISM: Artificial Sequence
```

```
<220> FEATURE:
<223> OTHER INFORMATION: Synthetic

<400> SEQUENCE: 133
auuacaguaa uguugaggg                                                 19

<210> SEQ ID NO 134
<211> LENGTH: 19
<212> TYPE: RNA
<213> ORGANISM: Artificial Sequence
<220> FEATURE:
<223> OTHER INFORMATION: Synthetic

<400> SEQUENCE: 134
auuaacuugu uggugcuga                                                 19

<210> SEQ ID NO 135
<211> LENGTH: 19
<212> TYPE: RNA
<213> ORGANISM: Artificial Sequence
<220> FEATURE:
<223> OTHER INFORMATION: Synthetic

<400> SEQUENCE: 135
uugagauaaa uaauccugu                                                 19

<210> SEQ ID NO 136
<211> LENGTH: 19
<212> TYPE: RNA
<213> ORGANISM: Artificial Sequence
<220> FEATURE:
<223> OTHER INFORMATION: Synthetic

<400> SEQUENCE: 136
gcaaacagaa ucaccacca                                                 19

<210> SEQ ID NO 137
<211> LENGTH: 31
<212> TYPE: DNA
<213> ORGANISM: Artificial Sequence
<220> FEATURE:
<223> OTHER INFORMATION: Synthetic

<400> SEQUENCE: 137
tactctactg tgtgtagcct tactgttctt c                                   31

<210> SEQ ID NO 138
<211> LENGTH: 24
<212> TYPE: DNA
<213> ORGANISM: Artificial Sequence
<220> FEATURE:
<223> OTHER INFORMATION: Synthetic

<400> SEQUENCE: 138
gagggttcaa ggagacctta ggtt                                           24

<210> SEQ ID NO 139
<211> LENGTH: 27
<212> TYPE: DNA
<213> ORGANISM: Artificial Sequence
<220> FEATURE:
<223> OTHER INFORMATION: Synthetic

<400> SEQUENCE: 139
ctccagatgg cgtgttagca gtccctc                                        27
```

```
<210> SEQ ID NO 140
<211> LENGTH: 1191
<212> TYPE: RNA
<213> ORGANISM: Homo sapiens

<400> SEQUENCE: 140
agucuccagc auccuccacc ugucuaccac cgagcauggg ccuauauuug aagccuuaga      60
ucucuccagc acaguaagca ccaggagucc augaagaaga uggcuccugc cauggaaucc     120
ccuacucuac ugaguguagc cuuacuguuc uucgcuccag auggcguguu agcaguccu     180 cagaaaccua aggucuccuu gaacccucca uggaauagaa uauuuaaagg agagaaugug     240
acucuuacau guaaugggaa caauuucuuu gaagucaguu ccaccaaaug guuccacaau     300
ggcagccuuu cagaagagac aaauucaagu uugaauauug ugaaugccaa auuugaagac     360
aguggagaau acaaauguca gcaccaacaa guuaaugaga gugaaccugu guaccuggaa     420
gucuucagug acuggcugcu ccuucaggcc ucugcugagg uggugaugga gggccagccc     480
cucuuccuca ggugccaugg uuggaggaac ugggaugugu acaaggugau cuauuauaag     540
gauggugaag cucucaagua cugguaugag aaccacaaca ucuccauuac aaaugccaca     600
guugaagaca guggaaccua cuacuguacg ggcaaagugu ggcagcugga cuaugagucu     660
gagcccucca acauuacugu aauaaaagcu ccgcgugaga aguacuggcu acaauuuuuu     720
aucccauugu uggugguagau ucuguuugcu guggacacag gauuauuuau cucaacucag     780
cagcagguca cauuucucuu gaagauuaag agaaccagga aaggcuucag acuucugaac     840
ccacauccua agccaaaccc caaaaacaac ugauauaauu acucaagaaa uauuugcaac     900
auuaguuuuu uuccagcauc agcaauugcu acucaauugu caaacacagc uugcaauaua     960
cauagaaacg ucugugcuca aggauuuaua gaaaugcuuc auuaaacuga gugaaacugg    1020
uuaaguggca uguaauagua agugcucaau uaacauuggu ugaauaaaug agagaaugaa    1080
uagauucauu uauuagcauu uguaaagag auguucaauu ucaauaaaau aaauauaaaa    1140
ccauguaaca gaaugcuucu gaguaaaaaa aaaaaaaaaa aaaaaaaaa a             1191
```